(12) United States Patent
Paramithiotis et al.

(10) Patent No.: US 10,935,549 B2
(45) Date of Patent: *Mar. 2, 2021

(54) BIOMARKERS OF LATENT TUBERCULOSIS INFECTION

(71) Applicants: Caprion Biosciences Inc., Montreal (CA); Case Western Reserve University, Cleveland, OH (US)

(72) Inventors: Eustache Paramithiotis, Boucherville (CA); W. Henry Boom, Shaker Heights, OH (US); Charles Bark, Lakewood, OH (US)

(73) Assignees: Caption Biosciences Inc., Montreal (CA); Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/246,592

(22) Filed: Jan. 14, 2019

(65) Prior Publication Data

US 2019/0277846 A1 Sep. 12, 2019

Related U.S. Application Data

(63) Continuation of application No. PCT/US2017/042039, filed on Jul. 14, 2017.

(60) Provisional application No. 62/362,225, filed on Jul. 14, 2016.

(51) Int. Cl.
*G01N 33/569* (2006.01)

(52) U.S. Cl.
CPC ..... *G01N 33/5695* (2013.01); *G01N 2800/26* (2013.01); *G01N 2800/50* (2013.01); *G01N 2800/52* (2013.01); *G01N 2800/56* (2013.01); *G01N 2800/60* (2013.01); *G01N 2800/70* (2013.01)

(58) Field of Classification Search
None
See application file for complete search history.

(56) References Cited

U.S. PATENT DOCUMENTS

| 9,857,378 B2 * | 1/2018 | Paramithiotis ..... G01N 33/5695 |
| 2007/0054407 A1 | 3/2007 | Chen et al. |
| 2018/0172699 A1 | 6/2018 | Paramithiotis et al. |

FOREIGN PATENT DOCUMENTS

| CN | 104792894 A | 7/2015 | |
| CN | 105588944 A | 5/2016 | |
| KR | 20110137766 A | 12/2011 | |
| WO | WO-2009/143519 A2 | 11/2009 | |
| WO | WO-2010/045714 A1 | 4/2010 | |
| WO | WO-2011/086161 A2 | 7/2011 | |
| WO | WO-2014133855 A1 * | 9/2014 | ......... G01N 33/6848 |
| WO | WO-2015/006515 A1 | 1/2015 | |
| WO | WO-2015/025281 A1 | 2/2015 | |

OTHER PUBLICATIONS

Bark et al., "Identification of Host Proteins Predictive of Early Stage *Mycobacterium tuberculosis* Infection", EBioMedicine 21(2017) 150-157.
Achkar et al., "Host Protein Biomarkers Identify Active Tuberculosis in HIV Uninfected and Co-infected Individuals", EBioMedicine 2 (2015) 1160-1168.
Doyle et al., "Enzyme-linked immunoadsorbent assay with electrochemical detection of .alpha.1-acid glycoprotein", Anal. Chem. 1984, 56, 13, 2355-2360.
Serrano et al., "Transcriptional profiles discriminate patients with pulmonary tuberculosis from non-tuberculous individuals depending on the presence of non-insulin diabetes mellitus", Clinical Immunology (2016) 162 pp. 107-117.
Wu et al., "Screening toll-like receptor markers to predict latent tuberculosis infection and subsequent tuberculosis disease in a Chinese population", BMC Medical Genetics (2015) 16:19.
Wanchu et al., "Biomarkers for Clinical and Incipient Tuberculosis: Performance in a TB-Endemic Country", PLOS One (2018) 3(4):e2071.
International Search Report and Written Opinion from PCT/US2017/042039, dated Dec. 22, 2017.
U.S. Appl. No. 14/835,939, U.S. Pat. No. 9,857,378, Aug. 26, 2015 Jan. 2, 2018, US 20160154005, Granted.
U.S. Appl. No. 15/814,554, filed Nov. 16, 2017, US 20180172699, Abandoned.

* cited by examiner

*Primary Examiner* — Mary Maille Lyons
(74) *Attorney, Agent, or Firm* — McCarter & English, LLP; Jonathan M. Sparks; Deborah L. Nagle

(57) ABSTRACT

The present invention provides biomarkers, methods and kits for diagnosing latent tuberculosis (TB) in a subject exposed to TB, and methods and kits for monitoring the effectiveness of treatment for latent TB.

9 Claims, 7 Drawing Sheets

|  | Discovery (N=104) | | | | Verification 1 (N=52) | | Verification 2 (N=16) | |
| --- | --- | --- | --- | --- | --- | --- | --- | --- |
|  | Non-Infected | Converter | LTBI | Active TB | Non-Infected (longitudinal) | Converter (longitudinal) | Non-Infected (longitudinal) | Converter (longitudinal) |
| n | 8 | 21 | 38 | 37 | 15 | 37 | 3 | 13 |
| Age (median) | 20 | 25 | 25 | 25 | 20 | 16 | 25 | 21 |
| Sex (% male) | 63 | 24 | 40 | 43 | 40 | 27 | 0 | 31 |
| BMI (median) | 21 | 22 | 22 | 19 | 21 | 21 | 21 | 22 |

| | Protein | CO v NI | LTBI v NI | ATB v NI | ATB v LTBI |
|---|---|---|---|---|---|
| Acute phase response | HP | 1.26 | 1.34 | 6.26 | 4.67 |
| | ORM1 | 1.25 | 1.37 | 3.83 | 2.80 |
| | SAA4 | 1.28 | 1.46 | 1.29 | 0.88 |
| | C1S | 1.14 | 1.20 | 1.18 | 0.98 |
| | C1R | 1.16 | 1.23 | 1.13 | 0.92 |
| | F5 | 1.15 | 1.14 | 1.01 | 0.89 |
| | SAA1 | 1.39 | 1.93 | 13.16 | 6.83 |
| | SERPINF1 | 1.03 | 1.12 | 0.88 | 0.78 |
| | SAA2 | 0.93 | 1.09 | 3.15 | 2.89 |
| | APCS | 1.07 | 1.20 | 2.33 | 1.93 |
| | ORM2 | 1.19 | 1.28 | 1.95 | 1.52 |
| | AMBP | 1.05 | 1.05 | 1.52 | 1.45 |
| | F9 | 0.91 | 1.10 | 1.24 | 1.13 |
| | AHSG | 0.94 | 1.03 | 0.54 | 0.53 |
| | TF | 1.04 | 1.00 | 0.49 | 0.94 |
| | IL1RAP | 1.01 | 0.98 | 0.44 | 0.44 |
| | CD163 | 1.13 | 1.08 | 0.97 | 0.90 |
| Inflammatory response | S100A8 | 1.26 | 1.29 | 2.64 | 2.04 |
| | S100A9 | 1.22 | 1.28 | 3.51 | 2.74 |
| | CD5L | 0.89 | 0.83 | 0.84 | 1.01 |
| | SOD3 | 0.85 | 0.73 | 0.59 | 0.81 |
| | CAT | 0.79 | 0.60 | 0.40 | 0.67 |
| | CPN1 | 1.15 | 1.15 | 1.07 | 0.93 |
| | ANPEP | 0.88 | 0.82 | 0.68 | 0.83 |
| | ATRN | 0.92 | 0.94 | 0.63 | 0.68 |
| | ALCAM | 1.00 | 0.74 | 0.41 | 0.55 |
| | KRT14 | 0.66 | 0.53 | 1.08 | 2.03 |
| Complement | CRP | 1.39 | 1.73 | 8.73 | 5.05 |
| | C2 | 1.12 | 1.16 | 1.21 | 1.04 |
| | C3 | 1.26 | 1.34 | 1.20 | 0.89 |
| | CLU | 1.13 | 1.19 | 0.92 | 0.77 |
| | C7 | 0.85 | 0.84 | 0.78 | 0.92 |
| | MBL2 | 0.70 | 0.85 | 0.64 | 0.75 |
| | C9 | 1.18 | 1.44 | 2.79 | 1.93 |
| | FCN3 | 1.09 | 1.38 | 1.49 | 1.08 |
| | KNG1 | 1.28 | 1.32 | 0.72 | 0.54 |
| | MASP1 | 0.96 | 1.00 | 0.79 | 0.79 |
| | CFD | 0.89 | 0.92 | 0.51 | 0.55 |
| | CR2 | 1.04 | 0.73 | 0.48 | 0.66 |
| | C4BPA | 1.10 | 1.15 | 2.05 | 1.78 |
| | MASP2 | 1.10 | 1.28 | 0.98 | 0.77 |
| Coagulation | SERPIND1 | 1.19 | 1.20 | 1.88 | 1.57 |
| | VWF | 1.34 | 1.08 | 1.06 | 0.98 |
| | PLEK | 1.46 | 1.23 | 0.92 | 0.75 |
| | FLNA | 1.29 | 1.18 | 0.68 | 0.58 |
| | PF4 | 0.72 | 0.74 | 0.62 | 0.84 |
| | F11 | 1.09 | 1.22 | 1.09 | 0.89 |
| | F12 | 0.93 | 0.82 | 0.84 | 1.02 |
| | PTGDS | 0.89 | 0.92 | 0.80 | 0.87 |
| | GP1BA | 1.02 | 1.01 | 0.77 | 0.76 |
| | MMRN1 | 0.80 | 0.79 | 0.74 | 0.93 |
| | F7 | 1.17 | 1.12 | 0.68 | 0.60 |
| | ADAMTS13 | 0.85 | 0.81 | 0.55 | 0.68 |
| | GP5 | 0.91 | 0.94 | 0.54 | 0.58 |
| | LRP1 | 1.12 | 0.94 | 0.43 | 0.46 |
| | SERPINA5 | 1.02 | 0.83 | 0.41 | 0.50 |
| | FGL2 | 0.50 | 0.52 | 0.40 | 0.77 |
| | PROCR | 0.87 | 0.84 | 0.31 | 0.37 |
| | FGA | 1.14 | 1.04 | 1.23 | 1.18 |

Figure 2B

| | Protein | CO v NI | LTBI v NI | ATB v NI | ATB v LTBI |
|---|---|---|---|---|---|
| Coagulation | SERPIND1 | 1.19 | 1.20 | 1.88 | 1.57 |
| | VWF | 1.34 | 1.08 | 1.06 | 0.98 |
| | PLEK | 1.46 | 1.23 | 0.92 | 0.75 |
| | FLNA | 1.29 | 1.18 | 0.68 | 0.58 |
| | PF4 | 0.72 | 0.74 | 0.62 | 0.84 |
| | F11 | 1.09 | 1.22 | 1.09 | 0.89 |
| | F12 | 0.93 | 0.82 | 0.84 | 1.02 |
| | PTGDS | 0.89 | 0.92 | 0.80 | 0.87 |
| | GP1BA | 1.02 | 1.01 | 0.77 | 0.76 |
| | MMRN1 | 0.80 | 0.79 | 0.74 | 0.93 |
| | F7 | 1.17 | 1.12 | 0.68 | 0.60 |
| | ADAMTS13 | 0.85 | 0.81 | 0.55 | 0.68 |
| | GP5 | 0.91 | 0.94 | 0.54 | 0.58 |
| | LRP1 | 1.12 | 0.94 | 0.43 | 0.46 |
| | SERPINA5 | 1.02 | 0.83 | 0.41 | 0.50 |
| | FGL2 | 0.50 | 0.52 | 0.40 | 0.77 |
| | PROCR | 0.87 | 0.84 | 0.31 | 0.37 |
| | FGA | 1.14 | 1.04 | 1.23 | 1.18 |
| Oxidative stress | S100A12 | 1.85 | 1.98 | 6.31 | 3.18 |
| | PRDX2 | 0.73 | 0.55 | 0.40 | 0.72 |
| | PON1 | 1.20 | 1.43 | 0.73 | 0.51 |
| | AGT | 0.97 | 1.07 | 0.83 | 0.78 |
| | SH3BGRL3 | 1.02 | 0.97 | 0.73 | 0.76 |
| | SEPP1 | 0.83 | 0.90 | 0.71 | 0.78 |
| | SOD1 | 0.96 | 0.69 | 0.57 | 0.83 |
| | MMP2 | 0.94 | 0.74 | 0.29 | 0.39 |
| Innate immunity | LGALS3BP | 1.31 | 1.33 | 1.65 | 1.23 |
| | LILRA3 | 1.62 | 1.47 | 1.25 | 0.85 |
| | VNN1 | 1.25 | 1.49 | 1.18 | 0.79 |
| | LBP | 1.12 | 1.40 | 2.44 | 1.75 |
| | PGLYRP2 | 1.23 | 1.24 | 0.68 | 0.55 |
| | HPR | 1.01 | 1.06 | 1.78 | 1.69 |
| | CSF1R | 1.07 | 1.00 | 0.57 | 0.57 |
| | SELENBP1 | 0.94 | 0.58 | 0.32 | 0.55 |
| Adaptive vs immune response | SERPINA1 | 1.19 | 1.27 | 3.32 | 2.62 |
| | LCP1 | 1.30 | 1.30 | 1.61 | 1.24 |
| | IGLL5 | 0.88 | 0.91 | 1.29 | 1.41 |
| | DBH | 1.52 | 1.12 | 0.92 | 0.82 |
| | A2M | 0.91 | 1.04 | 0.81 | 0.79 |
| | SERPINC1 | 1.70 | 1.93 | 1.21 | 0.62 |
| | LPA | 1.28 | 1.77 | 1.14 | 0.65 |
| | PIGR | 0.92 | 0.77 | 1.08 | 1.40 |
| | FCGR3A | 1.12 | 1.20 | 1.45 | 1.21 |
| | CD14 | 1.03 | 1.09 | 1.42 | 1.31 |
| | MMP9 | 1.11 | 1.05 | 1.37 | 1.31 |
| | ICAM1 | 1.06 | 1.17 | 1.37 | 1.17 |
| | CPB2 | 0.98 | 1.09 | 1.19 | 1.09 |
| | PROS1 | 0.90 | 1.02 | 0.90 | 0.88 |
| | THBS1 | 0.98 | 1.00 | 0.85 | 0.85 |
| | ICOSLG | 0.91 | 1.00 | 0.75 | 0.75 |
| | VCAM1 | 1.02 | 1.01 | 0.68 | 0.67 |
| | PTPRJ | 0.98 | 0.90 | 0.58 | 0.64 |
| | PNP | 0.73 | 0.53 | 0.46 | 0.87 |
| | BLVRB | 0.98 | 0.66 | 0.44 | 0.67 |
| | THBS4 | 1.03 | 0.79 | 0.31 | 0.40 |
| | DPP4 | 0.76 | 0.68 | 0.27 | 0.40 |
| | SECTM1 | 1.26 | 1.38 | 0.22 | 0.16 |
| | TAGLN2 | 1.34 | 1.33 | 1.04 | 0.78 |
| Lipid metabolism | APOA4 | 0.72 | 0.80 | 0.57 | 0.71 |
| | APOB | 1.38 | 1.41 | 0.96 | 0.68 |
| | APOE | 1.15 | 1.29 | 1.00 | 0.77 |
| | LCAT | 1.17 | 1.20 | 0.91 | 0.76 |
| | APOF | 1.30 | 1.31 | 0.99 | 0.76 |
| | APOD | 1.13 | 1.31 | 0.81 | 0.62 |
| | APOA1 | 1.03 | 1.11 | 0.71 | 0.64 |
| | APOC1 | 0.97 | 1.09 | 0.72 | 0.66 |
| | PCSK9 | 0.99 | 0.77 | 0.65 | 0.85 |
| | APOC2 | 0.94 | 1.04 | 0.63 | 0.61 |
| | APOC4 | 0.85 | 0.80 | 0.55 | 0.69 |
| | APOA2 | 0.97 | 1.04 | 0.51 | 0.49 |
| | CETP | 1.03 | 1.10 | 1.43 | 1.31 |
| | PRG4 | 1.22 | 1.12 | 2.09 | 1.87 |
| Glycolysis | TPI1 | 0.97 | 0.79 | 0.71 | 0.90 |
| | ALDOA | 0.81 | 0.83 | 0.65 | 0.78 |
| | LDHB | 0.91 | 0.79 | 0.53 | 0.67 |
| | LDHA | 0.90 | 0.62 | 0.49 | 0.79 |
| Carb Metab | CTBS | 1.06 | 1.03 | 0.63 | 0.61 |
| | NAGLU | 0.90 | 0.92 | 0.56 | 0.61 |

Figure 2C

| | Protein | CO v NI | LTBI v NI | ATB v NI | ATB v LTBI |
|---|---|---|---|---|---|
| Tissue development & remodeling | HRNR | 0.30 | 0.24 | 0.24 | 0.99 |
| | KRT9 | 0.72 | 0.65 | 0.62 | 0.96 |
| | FCGBP | 0.80 | 0.87 | 0.85 | 0.97 |
| | ECM1 | 0.84 | 0.81 | 0.92 | 1.13 |
| | LUM | 0.88 | 0.90 | 0.57 | 0.63 |
| | LRG1 | 1.18 | 1.34 | 2.90 | 2.16 |
| | KRT5 | 0.72 | 0.68 | 0.78 | 1.16 |
| | CA2 | 0.83 | 0.61 | 0.30 | 0.63 |
| | S100A4 | 1.20 | 0.77 | 0.16 | 0.21 |
| | COL1A1 | 0.66 | 0.49 | 0.17 | 0.34 |
| | CD248 | 0.90 | 0.74 | 0.19 | 0.26 |
| | RTN4RL2 | 0.77 | 0.76 | 0.35 | 0.46 |
| | CDL6A1 | 0.76 | 0.77 | 0.36 | 0.47 |
| | PTPRG | 1.01 | 1.05 | 0.40 | 0.38 |
| | KRT2 | 0.61 | 0.66 | 0.41 | 0.62 |
| | MEGF8 | 0.85 | 0.78 | 0.41 | 0.52 |
| | CDLEC11 | 1.25 | 0.97 | 0.42 | 0.44 |
| | EFEMP1 | 1.13 | 1.12 | 0.45 | 0.40 |
| | NCAM2 | 0.80 | 0.86 | 0.48 | 0.56 |
| | SEMA4B | 0.96 | 1.03 | 0.50 | 0.48 |
| | OGN | 1.06 | 0.95 | 0.51 | 0.53 |
| | COL6A3 | 1.01 | 0.90 | 0.52 | 0.57 |
| | AB13BP | 0.79 | 0.75 | 0.53 | 0.71 |
| | SPP2 | 1.05 | 1.05 | 0.53 | 0.50 |
| | DAG1 | 0.81 | 0.87 | 0.54 | 0.62 |
| | COMP | 1.11 | 1.00 | 0.55 | 0.56 |
| | SPARCL1 | 1.10 | 1.05 | 0.56 | 0.53 |
| | CRTAC1 | 1.04 | 1.01 | 0.62 | 0.61 |
| | CD109 | 1.27 | 1.08 | 0.65 | 0.60 |
| | BTD | 0.99 | 1.07 | 0.65 | 0.61 |
| | VASN | 0.87 | 0.87 | 0.73 | 0.84 |
| | Q5OX1 | 1.06 | 1.13 | 0.82 | 0.72 |
| | NRP1 | 0.97 | 1.09 | 1.22 | 1.12 |
| | PLS1 | 1.11 | 1.08 | 1.45 | 1.35 |
| | FAM20C | 1.22 | 1.41 | 1.81 | 1.29 |
| | PFN1 | 1.33 | 1.09 | 0.74 | 0.68 |

| | Protein | CO v NI | LTBI v NI | ATB v NI | ATB v LTBI |
|---|---|---|---|---|---|
| Cell proliferation | IGFBP3 | 0.81 | 0.84 | 0.41 | 0.49 |
| | IGFBP5 | 0.43 | 0.46 | 0.27 | 0.60 |
| | IGF1 | 0.70 | 0.67 | 0.42 | 0.62 |
| | IGFBP6 | 0.95 | 1.01 | 0.74 | 0.73 |
| | SPARC | 0.97 | 0.98 | 0.73 | 0.75 |
| | BCHE | 1.04 | 1.03 | 0.72 | 0.71 |
| | CHL1 | 1.05 | 1.01 | 0.64 | 0.63 |
| | FSTL1 | 0.86 | 0.99 | 0.55 | 0.56 |
| | IGF2 | 1.05 | 1.01 | 0.53 | 0.52 |
| | ENO1 | 1.07 | 0.98 | 0.41 | 0.42 |
| | PDGFRB | 0.61 | 0.69 | 0.39 | 0.56 |
| | AIFMI | 1.17 | 1.13 | 0.26 | 0.23 |
| | LTBP1 | 0.79 | 0.64 | 0.20 | 0.32 |
| | AK1 | 0.79 | 0.47 | 0.10 | 0.21 |
| | IGFBP2 | 0.90 | 1.13 | 1.55 | 1.38 |
| Cell migration & adhesion | TNXB | 0.85 | 0.83 | 0.40 | 0.49 |
| | GPLD1 | 0.79 | 0.98 | 0.58 | 0.50 |
| | FBLN1 | 0.85 | 0.81 | 0.53 | 0.65 |
| | IGFALS | 1.00 | 0.99 | 0.77 | 0.78 |
| | VCL | 1.12 | 1.05 | 0.73 | 0.69 |
| | PVR | 0.72 | 0.84 | 0.71 | 0.85 |
| | AOC3 | 0.92 | 0.91 | 0.65 | 0.72 |
| | NED1 | 0.99 | 1.05 | 0.63 | 0.59 |
| | ANGPTL3 | 1.44 | 1.26 | 0.55 | 0.44 |
| | TLN1 | 1.22 | 1.08 | 0.55 | 0.51 |
| | GSN | 0.97 | 0.98 | 0.54 | 0.55 |
| | NCAM1 | 0.99 | 0.95 | 0.53 | 0.56 |
| | CDH5 | 1.13 | 1.08 | 0.52 | 0.48 |
| | HSPG2 | 1.05 | 0.85 | 0.51 | 0.60 |
| | TPM3 | 1.20 | 1.12 | 0.50 | 0.45 |
| | CDH13 | 1.15 | 0.99 | 0.49 | 0.49 |
| | DSG2 | 1.17 | 1.19 | 0.48 | 0.40 |
| | TPM4 | 1.26 | 1.15 | 0.47 | 0.41 |
| | MCAM | 1.14 | 1.13 | 0.43 | 0.38 |
| | POSTN | 0.98 | 0.81 | 0.38 | 0.48 |
| | CNTN1 | 0.94 | 0.84 | 0.38 | 0.45 |
| | OMD | 0.79 | 0.67 | 0.30 | 0.45 |
| | ADAMDEC1 | 0.87 | 0.80 | 0.29 | 0.36 |
| | ACAN | 0.56 | 0.52 | 0.24 | 0.45 |
| | CLSTN1 | 0.92 | 0.69 | 0.15 | 0.22 |
| | MYOC | 0.74 | 0.50 | 0.13 | 0.26 |
| | PSG2 | 1.21 | 1.21 | 1.98 | 1.64 |
| | VTN | 1.10 | 1.16 | 0.75 | 0.65 |
| Glycosylation | MAN1A1 | 1.37 | 1.40 | 1.85 | 1.33 |
| | FUCA1 | 0.91 | 0.91 | 0.63 | 0.69 |
| | MAN2A1 | 1.01 | 0.95 | 0.54 | 0.57 |
| | FUCA2 | 0.73 | 0.84 | 0.50 | 0.59 |
| | B3GNT2 | 1.10 | 0.92 | 0.31 | 0.34 |

Figure 2D

| | Protein | CO v NI | LTBI v NI | ATB v NI | ATB v LTBI |
|---|---|---|---|---|---|
| Cell migration & adhesion | TNXB | 0.85 | 0.83 | 0.40 | 0.40 |
| | GPLD1 | 0.79 | 0.98 | 0.58 | 0.59 |
| | FBLN1 | 0.85 | 0.81 | 0.53 | 0.65 |
| | IGFALS | 1.00 | 0.99 | 0.77 | 0.78 |
| | VCL | 1.12 | 1.06 | 0.73 | 0.69 |
| | PVR | 0.72 | 0.84 | 0.71 | 0.85 |
| | AOC3 | 0.92 | 0.91 | 0.65 | 0.72 |
| | NED1 | 0.99 | 1.06 | 0.63 | 0.59 |
| | ANGPTL3 | 1.44 | 1.26 | 0.55 | 0.44 |
| | TUN1 | 1.22 | 1.08 | 0.55 | 0.51 |
| | GSN | 0.97 | 0.98 | 0.54 | 0.55 |
| | NCAM1 | 0.99 | 0.95 | 0.53 | 0.56 |
| | CDH5 | 1.13 | 1.08 | 0.52 | 0.48 |
| | HSPG2 | 1.06 | 0.85 | 0.51 | 0.60 |
| | TPM3 | 1.20 | 1.12 | 0.50 | 0.45 |
| | CDH13 | 1.15 | 0.99 | 0.49 | 0.49 |
| | DSG2 | 1.17 | 1.19 | 0.48 | 0.40 |
| | TPM4 | 1.26 | 1.16 | 0.47 | 0.41 |
| | MCAM | 1.14 | 1.13 | 0.43 | 0.38 |
| | POSTN | 0.98 | 0.81 | 0.38 | 0.48 |
| | CNTN1 | 0.94 | 0.84 | 0.38 | 0.45 |
| | OMD | 0.79 | 0.67 | 0.30 | 0.45 |
| | ADAMDEC1 | 0.87 | 0.80 | 0.29 | 0.36 |
| | ACAN | 0.56 | 0.52 | 0.24 | 0.45 |
| | CLSTN1 | 0.92 | 0.69 | 0.15 | 0.22 |
| | MYOC | 0.74 | 0.50 | 0.13 | 0.26 |
| | PSG2 | 1.21 | 1.21 | 1.98 | 1.64 |
| | VTN | 1.10 | 1.16 | 0.75 | 0.65 |
| Glycosylation | MAN1A1 | 1.37 | 1.40 | 1.85 | 1.33 |
| | FUCA1 | 0.91 | 0.91 | 0.63 | 0.69 |
| | MAN2A1 | 1.01 | 0.96 | 0.54 | 0.57 |
| | FUCA2 | 0.73 | 0.84 | 0.50 | 0.59 |
| | B3GNT2 | 1.10 | 0.92 | 0.31 | 0.34 |
| Proteolysis | PZP | 1.40 | 1.28 | 1.83 | 1.43 |
| | CNDP1 | 1.24 | 1.21 | 0.87 | 0.72 |
| | ITIH3 | 1.22 | 1.30 | 1.77 | 1.36 |
| | SERPINA6 | 1.02 | 1.13 | 1.07 | 0.94 |
| | PI16 | 0.83 | 0.73 | 0.30 | 0.42 |
| | CPQ | 0.98 | 0.63 | 0.18 | 0.28 |
| | UBE3B | 0.80 | 0.83 | 0.33 | 0.40 |
| | PCOLCE | 0.97 | 0.89 | 0.42 | 0.47 |
| | XPNPEP2 | 0.76 | 0.67 | 0.42 | 0.63 |
| | CST6 | 0.84 | 0.86 | 0.45 | 0.52 |
| | TMP2 | 0.66 | 0.62 | 0.50 | 0.80 |
| | SERPINA4 | 0.95 | 1.00 | 0.54 | 0.54 |
| | HGFAC | 0.98 | 0.93 | 0.58 | 0.63 |
| | PEPD | 1.08 | 1.07 | 0.67 | 0.62 |
| | CST3 | 0.96 | 1.07 | 0.78 | 0.73 |
| | FETUB | 1.04 | 1.09 | 1.32 | 1.21 |
| | GGH | 1.15 | 1.14 | 1.44 | 1.26 |
| | CPN2 | 1.00 | 1.02 | 0.92 | 0.90 |
| Transport | TTR | 2.86 | 2.51 | 1.67 | 0.67 |
| | SHBG | 1.54 | 1.49 | 1.13 | 0.76 |
| | ALB | 0.78 | 0.89 | 0.38 | 0.43 |
| | AFM | 0.87 | 0.85 | 0.45 | 0.53 |
| | HBB | 0.98 | 0.66 | 1.21 | 1.83 |
| | HBA1 | 0.87 | 0.55 | 0.97 | 1.76 |
| | SNCA | 0.89 | 0.58 | 0.21 | 0.36 |
| | ZC3H3 | 0.44 | 0.42 | 0.30 | 0.71 |
| | LAMP1 | 0.92 | 0.96 | 0.47 | 0.49 |
| | LYVE1 | 0.93 | 0.99 | 0.52 | 0.53 |
| | CLEC3B | 1.00 | 1.06 | 0.55 | 0.52 |
| | CACNA2D1 | 1.15 | 0.96 | 0.58 | 0.60 |
| | HSPA5 | 0.97 | 0.99 | 0.72 | 0.72 |
| | TFRC | 1.02 | 0.95 | 0.76 | 0.79 |
| | FTL | 0.94 | 1.04 | 2.39 | 2.31 |
| | POLIM1 | 1.24 | 1.14 | 0.75 | 0.66 |
| Other | CA1 | 0.92 | 0.60 | 0.35 | 0.58 |
| | RNASE1 | 1.05 | 0.97 | 0.48 | 0.49 |
| | MST1 | 1.07 | 1.04 | 0.91 | 0.87 |

Figure 3A

| | Gene | Becomes TST+ | Remains TST- |
|---|---|---|---|
| Acute phase | ORM1 | 1.63 | 1.95 |
| | CD163 | 1.19 | 1.34 |
| Inflammatory Response | SOD3 | 1.29 | 1.78 |
| | CPN1 | 1.23 | 1.16 |
| | ATRN | 1.20 | 1.17 |
| | S100A8 | 1.13 | 1.75 |
| | S100A9 | 1.12 | 1.78 |
| Comp. | C7 | 1.37 | 1.40 |
| | CR2 | 0.93 | 2.41 |
| | FCN3 | 1.00 | 1.64 |
| | MBL2 | 1.17 | 1.22 |
| Coagulation | VWF | 1.42 | 1.35 |
| | HABP2 | 1.31 | 1.23 |
| | FLNA | 1.33 | 1.01 |
| | SERPINA5 | 1.26 | 1.12 |
| | PROCR | 1.23 | 1.14 |
| | PLEK | 1.13 | 0.86 |
| Oxidative stress | GPX3 | 1.31 | 1.29 |
| | HYOU1 | 1.23 | 1.20 |
| | PON1 | 1.28 | 1.00 |
| | SEPP1 | 1.25 | 1.19 |
| | S100A12 | 1.03 | 1.74 |
| Innate immune | LBP | 1.46 | 1.25 |
| | PGLYRP2 | 1.38 | 1.21 |
| | VNN1 | 1.25 | 1.20 |
| Adaptive immune | THBS4 | 1.39 | 1.20 |
| | CD14 | 1.28 | 1.27 |
| | PROS1 | 1.27 | 1.22 |
| | LCP1 | 1.23 | 1.31 |
| | VCAM1 | 1.23 | 1.29 |
| | SECTM1 | 1.30 | 1.19 |
| | LPA | 1.21 | 1.08 |
| | CPB2 | 1.20 | 1.18 |
| | DBH | 1.02 | 2.00 |
| Lipid metabolism | APOA4 | 1.76 | 1.37 |
| | APOE | 1.76 | 1.32 |
| | APOA1 | 1.70 | 1.40 |
| | PCSK9 | 1.42 | 2.59 |
| | PRG4 | 1.29 | 1.24 |
| | APOD | 1.27 | 1.04 |
| | APOC3 | 1.22 | 0.97 |
| | LCAT | 1.21 | 1.16 |
| Glycolysis | LDHA | 1.31 | 1.12 |
| Transport | CLEC3B | 1.29 | 1.22 |
| | PTGDS | 1.24 | 1.22 |
| | CACNA2D1 | 1.21 | 1.00 |
| | LAMP1 | 1.19 | 1.20 |
| | HBA1 | 0.79 | 1.01 |

Figure 3B

| | Gene | Becomes TST+ | Remains TST- |
|---|---|---|---|
| Tissue development & remodeling | MMP2 | 1.47 | 1.20 |
| | ECM1 | 1.43 | 1.34 |
| | LRG1 | 1.28 | 1.34 |
| | LUM | 1.25 | 1.22 |
| | BTD | 1.23 | 1.26 |
| | COLEC11 | 1.23 | 1.20 |
| | COMP | 1.35 | 1.19 |
| | FCGBP | 1.35 | 1.01 |
| | CD248 | 1.34 | 1.18 |
| | CNTN1 | 1.32 | 1.01 |
| | COL1A1 | 1.25 | 1.17 |
| | MINPP1 | 1.24 | 1.19 |
| | PTPRG | 1.22 | 1.15 |
| | MEGF8 | 1.21 | 1.08 |
| | VASN | 1.21 | 1.19 |
| Cell proliferation | IGF2 | 1.58 | 1.70 |
| | ENO1 | 1.32 | 1.03 |
| | IGFBP3 | 1.24 | 1.16 |
| | BCHE | 1.21 | 1.14 |
| | AK1 | 1.08 | 2.42 |
| cell migration & adhesion | ZYX | 1.64 | 1.72 |
| | POSTN | 1.40 | 1.32 |
| | MYOC | 1.30 | 1.26 |
| | TNXB | 1.30 | 1.23 |
| | TGFBI | 1.25 | 1.23 |
| | ADAMDEC1 | 1.32 | 1.15 |
| | CDH13 | 1.24 | 1.19 |
| | IGFALS | 1.24 | 1.16 |
| | OMD | 1.23 | 1.10 |
| | DSG2 | 1.22 | 1.16 |
| | NID1 | 1.21 | 1.19 |
| | GPLD1 | 1.20 | 1.13 |
| | MCAM | 1.20 | 1.14 |
| | CLSTN1 | 1.15 | 1.48 |
| | SELL | 1.15 | 1.25 |
| | CDH5 | 1.18 | 1.23 |
| Glycosylat. | FUCA2 | 1.29 | 1.19 |
| | MAN1A1 | 1.19 | 1.23 |
| Proteolysis | PCOLCE | 1.30 | 1.26 |
| | CPN2 | 1.30 | 1.20 |
| | CST6 | 1.25 | 1.19 |
| | CNDP1 | 1.22 | 1.19 |
| | CPQ | 1.22 | 1.05 |
| | PEPD | 1.22 | 1.17 |
| Other | MST1 | 1.20 | 1.23 |
| | CKM | 1.65 | 1.19 |
| | YWHAE | 0.34 | 4.07 |

Figure 4A

| | Protein | TST+CONVERSION AT M3 | |
|---|---|---|---|
| | | M3 vs D1 | M6 vs D1 |
| Acute phase | ORM1 | 1.66 | 1.23 |
| | CD163 | 1.35 | 1.22 |
| Inflammatory Response | SOD3 | - | - |
| | CPN1 | 1.26 | 1.10 |
| | ATRN | 1.26 | 1.13 |
| | S100A8 | 1.11 | 1.04 |
| | S100A9 | 1.17 | 1.07 |
| Comp. | C7 | 1.43 | 1.34 |
| | CR2 | 1.19 | 1.09 |
| | FCN3 | 1.16 | 0.93 |
| | MBL2 | 1.30 | 1.10 |
| Coagulation | VWF | 1.58 | 1.38 |
| | HABP2 | 1.42 | 1.19 |
| | FLNA | 1.05 | 0.96 |
| | SERPINA5 | 1.28 | 1.18 |
| | PROCR | 1.30 | 1.18 |
| | PLEK | 1.02 | 1.00 |
| Oxidative stress | GPX3 | 1.30 | 1.22 |
| | HYOU1 | 1.32 | 1.20 |
| | PON1 | 1.18 | 1.03 |
| | SEPP1 | 1.25 | 1.19 |
| | S100A12 | 1.05 | 0.94 |
| Innate immune | LBP | 1.48 | 1.17 |
| | PGLYRP2 | 1.34 | 1.31 |
| | VNN1 | 1.32 | 1.13 |
| Adaptive immune | THBS4 | 1.45 | 1.47 |
| | CD14 | 1.28 | 1.21 |
| | PROS1 | 1.24 | 1.18 |
| | LCP1 | 1.26 | 1.17 |
| | VCAM1 | 1.30 | 1.27 |
| | SECTM1 | 1.31 | 1.32 |
| | LPA | 1.18 | 1.22 |
| | CPB2 | 1.23 | 1.10 |
| | DBH | 1.28 | 1.11 |
| Lipid metabolism | APOA4 | 1.79 | 1.86 |
| | APOE | 1.69 | 1.52 |
| | APOA1 | 1.60 | 1.41 |
| | PCSK9 | 0.98 | 1.11 |
| | PRG4 | 1.23 | 1.07 |
| | APOD | 1.29 | 1.04 |
| | APOC3 | 1.11 | 1.07 |
| | LCAT | 1.25 | 1.10 |
| Glycolysis | LDHA | 1.33 | 1.27 |
| Transport | CLEC3B | 1.30 | 1.28 |
| | PTGDS | 1.24 | 1.25 |
| | CACNA2D1 | 1.23 | 1.13 |
| | LAMP1 | 1.21 | 1.18 |
| | HBA1 | 1.68 | 1.11 |

Figure 4B

| | Protein | TST+CONVERSION AT M3 | |
|---|---|---|---|
| | | M3 vs D1 | M6 vs D1 |
| Tissue development & remodeling | MMP2 | 1.37 | 1.37 |
| | ECM1 | 1.43 | 1.35 |
| | LRG1 | 1.31 | 1.20 |
| | LUM | 1.33 | 1.29 |
| | BTD | 1.24 | 1.17 |
| | COLEC11 | 1.26 | 1.22 |
| | COMP | 1.35 | 1.31 |
| | FCGBP | 1.36 | 1.04 |
| | CD248 | 1.39 | 1.43 |
| | CNTN1 | 1.18 | 1.27 |
| | COL1A1 | 1.27 | 1.30 |
| | MINPP1 | 1.27 | 1.20 |
| | PTPRG | 1.24 | 1.17 |
| | MEGF8 | 1.26 | 1.14 |
| | VASN | 1.21 | 1.20 |
| Cell proliferation | IGF2 | - | - |
| | ENO1 | 1.15 | 1.17 |
| | IGFBP3 | 1.26 | 1.17 |
| | BCHE | 1.23 | 1.12 |
| | AK1 | 1.18 | 1.15 |
| cell migration & adhesion | ZYX | - | - |
| | POSTN | 1.49 | 1.54 |
| | MYOC | 1.37 | 1.33 |
| | TNXB | 1.25 | 1.27 |
| | TGFBI | 1.31 | 1.19 |
| | ADAMDEC1 | 1.31 | 1.21 |
| | CDH13 | 1.31 | 1.27 |
| | IGFALS | 1.35 | 1.29 |
| | OMD | 1.31 | 1.33 |
| | DSG2 | 1.23 | 1.22 |
| | NID1 | 1.24 | 1.18 |
| | GPLD1 | 1.28 | 1.11 |
| | MCAM | 1.23 | 1.12 |
| | CLSTN1 | 1.30 | 1.26 |
| | SELL | 1.19 | 1.15 |
| | CDH5 | 1.30 | 1.26 |
| Glycosylat. | FUCA2 | 1.30 | 1.27 |
| | MAN1A1 | 1.27 | 1.16 |
| Proteolysis | PCOLCE | 1.32 | 1.26 |
| | CPN2 | 1.33 | 1.22 |
| | CST6 | 1.25 | 1.21 |
| | CNDP1 | 1.26 | 0.96 |
| | CPQ | 1.23 | 1.33 |
| | PEPD | 1.24 | 1.18 |
| Other | MST1 | 1.25 | 1.15 |
| | CKM | 1.42 | 1.64 |
| | YWHAE | 1.15 | 1.18 | ns
BIOMARKERS OF LATENT TUBERCULOSIS INFECTION

RELATED APPLICATIONS

This application is a 35 § U.S.C. 111(a) continuation application which claims the benefit of priority to PCT/US2017/042039, filed on Jul. 14, 2017, which claims priority to U.S. Provisional Patent Application No. 62/362,225, filed on Jul. 14, 2016, the entire contents of which are hereby incorporated herein by reference.

GOVERNMENT SUPPORT

This invention was made with government support under grant number HHSN272200800047C, awarded by National Institute of Health (NIH)/National Institute of Allergy and Infectious Diseases (NIAID), grant numbers N01-AI95383 and HHSN266200700022C/N01-AI70022 awarded by National Institutes of Health National Institute of Allergy and Infectious Diseases, and grant number CTSA KL2TR000440 awarded by the National Institutes of Health/National Center for Research Resources (NIH/NCRR). The government has certain rights in the invention.

BACKGROUND OF THE INVENTION

Tuberculosis (TB) remains a major global public health problem. About a third of the world's population is latently infected with *Mycobacterium tuberculosis*, and an estimated 8.7 million new TB cases were diagnosed in 2011 (World Health Organization, Global tuberculosis control: WHO report 2011, 2011: Geneva, Switzerland). In addition, in 2011 almost one million TB-associated deaths occurred among HIV uninfected (HIV−) individuals and about 0.43 million deaths among HIV-infected (HIV+) individuals.

In addition to prevention, the cornerstones of TB control are reduction of transmission, morbidity, and mortality all of which require early treatment initiation. This in turn necessitates timely TB diagnosis, underlining the need for new rapid diagnostic tests. Rapid identification of active TB is the key unmet need in TB disease management.

Currently, TB diagnostic tests depend on the detection of *M. tuberculosis* which, thus, require a specimen from the site of disease which is not always easy to obtain. Furthermore, the current tests for TB are limited by lack of sensitivity (microscopy of sputum smears) or require amplification of *M. tuberculosis* which takes weeks (culture) and/or is expensive (molecular detection). Moreover, these gold standard tests (culture and molecular detection) require laboratory infrastructure which is not accessible in many endemic regions.

In addition, diagnosis of latent TB infection (LTBI) is based on host immunological activity measured by either the tuberculin skin test (TST) or the interferon gamma release assay (IGRA). Risk of developing active TB is highest after recent infection, but neither TST not IGRA tests can distinguish between a recent infection and a cleared infection.

Accordingly, there is a need in the art for novel TB biomarkers that are easily detectable, and neither require a specimen from the site of infection, nor laboratory infrastructure to provide rapid TB diagnosis and limit the spread of the disease. Furthermore, developing new tests that identify recent infection would allow for targeted treatment for those most likely to progress to active TB, and is a priority among international TB agencies.

SUMMARY OF THE INVENTION

The present invention is based, at least in part, on the discovery of markers that are associated with the presence of latent tuberculosis (TB) in a subject exposed to TB, e.g., in order to target treatment to those likely to develop active TB and/or spread the disease.

Accordingly, the present invention provides sensitive and facile methods and kits for determining whether a subject exposed to TB has latent TB, as well as methods for monitoring the effectiveness of a therapy for treating TB in a subject by measuring and identifying particular markers, or particular combinations of markers.

Accordingly, in one aspect the present invention provides methods for determining whether a subject exposed to tuberculosis (TB) will develop latent TB. The methods include determining the level of one or more markers listed in Table 1 in a sample(s) from the subject; comparing the level of the one or more markers in the subject sample(s) with a level of the one or more markers in a control sample(s), wherein a difference in the level of the one or more markers in the subject sample(s) as compared to the level of the one or more markers in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of one or more markers listed in Table 1 in a first sample(s) from the subject prior to the initiation of the treatment; determining the level of one or more markers listed in Table 1 in a second sample(s) from the subject after at least a portion of the treatment has been administered; comparing the level of the one or more markers in the first sample(s) with a level of the one or more markers in the second sample(s), wherein a difference in the level of the one or more markers in the first sample(s) as compared to the level of the one or more markers in the second sample(s) indicates that the treatment is effective, thereby monitoring the effectiveness of a treatment in the subject having latent TB.

In one embodiment, the methods further comprise determining the level of one or more markers selected from the group consisting of CLEC3B, ECM1, PON1, VTN, IGFALS, IGFBP3, CLU, VWF, SPP2, SELL, LUM, NCAM1, and TLN1.

In one embodiment, the level of the marker is an expression level and/or activity of the marker.

In one embodiment, the level in the subject sample(s) is determined by mass spectrometry. In one embodiment, the mass spectrometry is matrix assisted laser desorption/time of flight (MALDI/TOF) mass spectrometry, liquid chromatography quadruple ion trap electrospray (LCQ-MS), or surface enhanced laser desorption ionization/time of flight (SELDI/TOF) mass spectrometry. In another embodiment, the level in the subject sample(s) is determined by immunoassay.

In one embodiment, the sample(s) from the subject is a fluid sample(s). In another embodiment, the sample(s) from the subject is a tissue sample(s).

In one embodiment, the one or more markers is selected from the group consisting of CLEC3B, ECM1, PON1, VTN, IGFALS, IGFBP3, CLU, VWF, SPP2, SELL, LUM, NCAM1, and TLN1.

In another embodiment, the methods further comprise determining the level of one or more of PRG4, CA1, SHBG, CPN1, CPN2, QSOX1, PRDX2, APOA1, CA2, LPA, TAGLN2, GPX3, MST1, CNDP1, ATRN, PFN1, PEPD, VASN, BTD, CPB2, GPLD1, DBH, HGFAC, CDH5, LRG1, MASP1, PGLYRP2, TNXB, CD14, CKM, APOE, MAN1A1, PROS1, S100A8, S100A9, HABP2, BCHE, LCAT, PDLIM1, FCN3, ORM1, TGFBI, THBS1, GPS, CD163, VCAM1, LGALS3BP, PTGDS, APOC3, MINPP1, SEPP1, APOA4, MASP2, HYOU1, IGF2, GP1BA, CACNA2D1, CNTN1, NID1, COMP, PCSK9, LCP1 and APOC1.

In one aspect the present invention provides methods for determining whether a subject exposed to TB will develop latent tuberculosis (TB). The methods include determining the level of CLEC3B and the level of ECM1 in a sample(s) from the subject; comparing the level of CLEC3B and the level of ECM1 in the subject sample(s) with a level of CLEC3B and a level of ECM1 in a control sample(s), wherein a difference in the level of CLEC3B and a difference in the level of ECM1 in the subject sample(s) as compared to the level of CLEC3B and the level of ECM1 in the control sample(s) indicates that the subject will develop latent tuberculosis (TB). In one embodiment, the methods further comprise determining the level of one or more markers selected from the group consisting of PON1, VTN, IGFALS, IGFBP3, CLU, VWF, SPP2, SELL, LUM, NCAM1, and TLN1 in a sample(s) from the subject, thereby determining whether the subject exposed to TB will develop latent TB.

In one aspect the present invention provides methods for monitoring the effectiveness of a treatment in a subject having latent tuberculosis (TB). The methods include determining the level of CLEC3B and the level of ECM1 in a first sample(s) from the subject prior to the initiation of the treatment; determining the level of CLEC3B and the level of ECM1 in a second sample(s) from the subject after at least a portion of the treatment has been administered; comparing the level of CLEC3B and the level of ECM1 in the first sample(s) with a level of CLEC3B and the level of ECM1 in the second sample(s), wherein a difference in the level of CLEC3B and a difference in the level of ECM1 in the first sample(s) as compared to the level of the CLEC3B and the level of ECM1 in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, and the level of PON1 in a sample(s) from the subject; comparing the level of CLEC3B, the level of ECM1, and the level of PON1 in the subject sample(s) with a level of CLEC3B, the level of ECM1, and the level of PON1 in a control sample(s), wherein a difference in the level of CLEC3B, a difference in the level of ECM1, and a difference in the level of PON1 in the subject sample(s) as compared to the level of CLEC3B, the level of ECM1, and the level of PON1 in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, and the level of PON1 in a first sample(s) from the subject prior to the initiation of the treatment; determining the level of CLEC3B, the level of ECM1, and the level of PON1 in a second sample(s) from the subject after at least a portion of the treatment has been administered; comparing the level of CLEC3B, the level of ECM1, and the level of PON1 in the first sample(s) with a level of CLEC3B, the level of ECM1, and the level of PON1 in the second sample(s), wherein a difference in the level of CLEC3B, the level of ECM1, and the level of PON1 in the first sample(s) as compared to the level of CLEC3B, the level of ECM1, and the level of PON1 in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, and the level of VTN in a sample(s) from the subject; comparing the level of CLEC3B, the level of ECM1, and the level of VTN in the subject sample(s) with a level of CLEC3B, the level of ECM1, and the level of VTN in a control sample(s), wherein a difference in the level of CLEC3B, a difference in the level of ECM1, and a difference in the level of VTN in the subject sample(s) as compared to the level of CLEC3B, the level of ECM1, and the level of VTN in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, and the level of VTN in a first sample(s) from the subject prior to the initiation of the treatment; determining the level of CLEC3B, the level of ECM1, and the level of VTN in a second sample(s) from the subject after at least a portion of the treatment has been administered; comparing the level of CLEC3B, the level of ECM1, and the level of VTN in the first sample(s) with a level of CLEC3B, the level of ECM1, and the level of VTN in the second sample(s), wherein a difference in the level of CLEC3B, the level of ECM1, and the level of VTN in the first sample(s) as compared to the level of CLEC3B, the level of ECM1, and the level of VTN in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of PON1, and the level of VTN in a sample(s) from the subject; comparing the level of CLEC3B, the level of ECM1, the level of PON1, and the level of VTN in the subject sample(s) with a level of CLEC3B, the level of ECM1, the level of PON1, and the level of VTN in a control sample(s), wherein a difference in the level of CLEC3B, a difference in the level of ECM1, a difference in the level of PON1, and a difference in the level of VTN in the subject sample(s) as compared to the level of CLEC3B, the level of ECM1, the level of PON1, and the level of VTN in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of PON1, and the level of VTN in a first sample(s) from the subject prior to the initiation of the treatment; determining the level of CLEC3B, the level of ECM1, the level of PON1, and the level of VTN in a second sample(s) from the subject after at least a portion of the treatment has been administered; comparing the level of CLEC3B, the level of ECM1, the level of PON1, and the level of VTN in the first sample(s) with a level of CLEC3B, the level of ECM1, the level of PON1, and the level of VTN in the second sample(s), wherein a difference in the level of CLEC3B, the level of ECM1, the level of PON1, and the level of VTN in the first sample(s) as compared to the level of CLEC3B, the level of ECM1, the level of PON1, and the level of VTN in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of PON1, and the level of IGFALS in a sample(s) from the subject; comparing the level of CLEC3B, the level of ECM1, the level of PON1, and the level of IGFALS in the subject sample(s) with a level of CLEC3B, the level of ECM1, the level of PON1, and the level of IGFALS in a control sample(s), wherein a difference in the level of CLEC3B, a difference in the level of ECM1, a difference in the level of PON1, and a difference in the level of IGFALS in the subject sample(s) as compared to the level of CLEC3B, the level of ECM1, the level of PON1, and the level of IGFALS in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of PON1, and the level of IGFALS in a first sample(s) from the subject prior to the initiation of the treatment; determining the level of CLEC3B, the level of ECM1, the level of PON1, and the level of IGFALS in a second sample(s) from the subject after at least a portion of the treatment has been administered; comparing the level of CLEC3B, the level of ECM1, the level of PON1, and the level of IGFALS in the first sample(s) with a level of CLEC3B, the level of ECM1, the level of PON1, and the level of IGFALS in the second sample(s), wherein a difference in the level of CLEC3B, the level of ECM1, the level of PON1, and the level of IGFALS in the first sample(s) as compared to the level of CLEC3B, the level of ECM1, the level of PON1, and the level of IGFALS in the second sample(s) indicates that the treatment is effective, thereby monitoring the effectiveness of a treatment in the subject having latent TB In one aspect the present invention provides methods for determining whether a subject exposed to TB will develop latent tuberculosis (TB). The methods include determining the level of CLEC3B, the level of ECM1, the level of PON1, and the level of IGFBP3 in a sample(s) from the subject; comparing the level of CLEC3B, the level of ECM1, the level of PON1, and the level of IGFBP3 in the subject sample(s) with a level of CLEC3B, the level of ECM1, the level of PON1, and the level of IGFBP3 in a control sample(s), wherein a difference in the level of CLEC3B, a difference in the level of ECM1, a difference in the level of PON1, and a difference in the level of IGFBP3 in the subject sample(s) as compared to the level of CLEC3B, the level of ECM1, the level of PON1, and the level of IGFBP3 in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of PON1, and the level of IGFBP3 in a first sample(s) from the subject prior to the initiation of the treatment; determining the level of CLEC3B, the level of ECM1, the level of PON1, and the level of IGFBP3 in a second sample(s) from the subject after at least a portion of the treatment has been administered; comparing the level of CLEC3B, the level of ECM1, the level of PON1, and the level of IGFBP3 in the first sample(s) with a level of CLEC3B, the level of ECM1, the level of PON1, and the level of IGFBP3 in the second sample(s), wherein a difference in the level of CLEC3B, the level of ECM1, the level of PON1, and the level of IGFBP3 in the first sample(s) as compared to the level of CLEC3B, the level of ECM1, the level of PON1, and the level of IGFBP3 in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of PON1, and the level of CLU in a sample(s) from the subject; comparing the level of CLEC3B, the level of ECM1, the level of PON1, and the level of CLU in the subject sample(s) with a level of CLEC3B, the level of ECM1, the level of PON1, and the level of CLU in a control sample(s), wherein a difference in the level of CLEC3B, a difference in the level of ECM1, a difference in the level of PON1, and a difference in the level of CLU in the subject sample(s) as compared to the level of CLEC3B, the level of ECM1, the level of PON1, and the level of CLU in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of PON1, and the level of CLU in a first sample(s) from the subject prior to the initiation of the treatment; determining the level of CLEC3B, the level of ECM1, the level of PON1, and the level of CLU in a second sample(s) from the subject after at least a portion of the treatment has been administered; comparing the level of CLEC3B, the level of ECM1, the level of PON1, and the level of CLU in the first sample(s) with a level of CLEC3B, the level of ECM1, the level of PON1, and the level of CLU in the second sample(s), wherein a difference in the level of CLEC3B, the level of ECM1, the level of PON1, and the level of CLU in the first sample(s) as compared to the level of CLEC3B, the level of ECM1, the level of PON1, and the level of CLU in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of PON1, and the level of VWF in a sample(s) from the subject; comparing the level of CLEC3B, the level of ECM1, the level of PON1, and the level of VWF in the subject sample(s) with a level of CLEC3B, the level of ECM1, the level of PON1, and the level of VWF in a control sample(s), wherein a difference in the level of CLEC3B, a difference in the level of ECM1, a difference in the level of PON1, and a difference in the level of VWF in the subject sample(s) as compared to the level of CLEC3B, the level of ECM1, the level of PON1, and the level of VWF in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of PON1, and the level of VWF in a first sample(s) from the subject prior to the initiation of the treatment; determining the level of CLEC3B, the level of ECM1, the level of PON1, and the level of VWF in a second sample(s) from the subject after at least a portion of the treatment has been administered; comparing the level of CLEC3B, the level of ECM1, the level of PON1, and the level of VWF in the first sample(s) with a level of CLEC3B, the level of ECM1, the level of PON1, and the level of VWF in the second sample(s), wherein a difference in the level of CLEC3B, the level of ECM1, the level of PON1, and the level of VWF in the first sample(s) as compared to the level of CLEC3B, the level of ECM1, the level of PON1, and the level of VWF in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of PON1, and the level of SPP2 in a sample(s) from the subject; comparing the level of CLEC3B, the level of ECM1, the level of PON1, and the level of SPP2 in the subject sample(s) with a level of CLEC3B, the level of ECM1, the level of PON1, and the level of SPP2 in a control sample(s), wherein a difference in the level of CLEC3B, a difference in the level of ECM1, a difference in the level of PON1, and a difference in the level of SPP2 in the subject sample(s) as compared to the level of CLEC3B, the level of ECM1, the level of PON1, and the level of SPP2 in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of PON1, and the level of SPP2 in a first sample(s) from the subject prior to the initiation of the treatment; determining the level of CLEC3B, the level of ECM1, the level of PON1, and the level of SPP2 in a second sample(s) from the subject after at least a portion of the treatment has been administered; comparing the level of CLEC3B, the level of ECM1, the level of PON1, and the level of SPP2 in the first sample(s) with a level of CLEC3B, the level of ECM1, the level of PON1, and the level of SPP2 in the second sample(s), wherein a difference in the level of CLEC3B, the level of ECM1, the level of PON1, and the level of SPP2 in the first sample(s) as compared to the level of CLEC3B, the level of ECM1, the level of PON1, and the level of SPP2 in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of PON1, and the level of SELL in a sample(s) from the subject; comparing the level of CLEC3B, the level of ECM1, the level of PON1, and the level of SELL in the subject sample(s) with a level of CLEC3B, the level of ECM1, the level of PON1, and the level of SELL in a control sample(s), wherein a difference in the level of CLEC3B, a difference in the level of ECM1, a difference in the level of PON1, and a difference in the level of SELL in the subject sample(s) as compared to the level of CLEC3B, the level of ECM1, the level of PON1, and the level of SELL in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of PON1, and the level of SELL in a first sample(s) from the subject prior to the initiation of the treatment; determining the level of CLEC3B, the level of ECM1, the level of PON1, and the level of SELL in a second sample(s) from the subject after at least a portion of the treatment has been administered; comparing the level of CLEC3B, the level of ECM1, the level of PON1, and the level of SELL in the first sample(s) with a level of CLEC3B, the level of ECM1, the level of PON1, and the level of SELL in the second sample(s), wherein a difference in the level of CLEC3B, the level of ECM1, the level of PON1, and the level of SELL in the first sample(s) as compared to the level of CLEC3B, the level of ECM1, the level of PON1, and the level of SELL in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of PON1, and the level of LUM in a sample(s) from the subject; comparing the level of CLEC3B, the level of ECM1, the level of PON1, and the level of LUM in the subject sample(s) with a level of CLEC3B, the level of ECM1, the level of PON1, and the level of LUM in a control sample(s), wherein a difference in the level of CLEC3B, a difference in the level of ECM1, a difference in the level of PON1, and a difference in the level of LUM in the subject sample(s) as compared to the level of CLEC3B, the level of ECM1, the level of PON1, and the level of LUM in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of PON1, and the level of LUM in a first sample(s) from the subject prior to the initiation of the treatment; determining the level of CLEC3B, the level of ECM1, the level of PON1, and the level of LUM in a second sample(s) from the subject after at least a portion of the treatment has been administered; comparing the level of CLEC3B, the level of ECM1, the level of PON1, and the level of LUM in the first sample(s) with a level of CLEC3B, the level of ECM1, the level of PON1, and the level of LUM in the second sample(s), wherein a difference in the level of CLEC3B, the level of ECM1, the level of PON1, and the level of LUM in the first sample(s) as compared to the level of CLEC3B, the level of ECM1, the level of PON1, and the level of LUM in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of PON1, and the level of NCAM1 in a sample(s) from the subject; comparing the level of CLEC3B, the level of ECM1, the level of PON1, and the level of NCAM1 in the subject sample(s) with a level of CLEC3B, the level of ECM1, the level of PON1, and the level of NCAM1 in a control sample(s), wherein a difference in the level of CLEC3B, a difference in the level of ECM1, a difference in the level of PON1, and a difference in the level of NCAM1 in the subject sample(s) as compared to the level of CLEC3B, the level of ECM1, the level of PON1, and the level of NCAM1 in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of PON1, and the level of NCAM1 in a first sample(s) from the subject prior to the initiation of the treatment; determining the level of CLEC3B, the level of ECM1, the level of PON1, and the level of NCAM1 in a second sample(s) from the subject after at least a portion of the treatment has been administered; comparing the level of CLEC3B, the level of ECM1, the level of PON1, and the level of NCAM1 in the first sample(s) with a level of CLEC3B, the level of ECM1, the level of PON1, and the level of NCAM1 in the second sample(s), wherein a difference in the level of CLEC3B, the level of ECM1, the level of PON1, and the level of NCAM1 in the first sample(s) as compared to the level of CLEC3B, the level of ECM1, the level of PON1, and the level of NCAM1 in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of PON1, and the level of TLN1 in a sample(s) from the subject; comparing the level of CLEC3B, the level of ECM1, the level of PON1, and the level of TLN1 in the subject sample(s) with a level of CLEC3B, the level of ECM1, the level of PON1, and the level of TLN1 in a control sample(s), wherein a difference in the level of CLEC3B, a difference in the level of ECM1, a difference in the level of PON1, and a difference in the level of TLN1 in the subject sample(s) as compared to the level of CLEC3B, the level of ECM1, the level of PON1, and the level of TLN1 in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of PON1, and the level of TLN1 in a first sample(s) from the subject prior to the initiation of the treatment; determining the level of CLEC3B, the level of ECM1, the level of PON1, and the level of TLN1 in a second sample(s) from the subject after at least a portion of the treatment has been administered; comparing the level of CLEC3B, the level of ECM1, the level of PON1, and the level of TLN1 in the first sample(s) with a level of CLEC3B, the level of ECM1, the level of PON1, and the level of TLN1 in the second sample(s), wherein a difference in the level of CLEC3B, the level of ECM1, the level of PON1, and the level of TLN1 in the first sample(s) as compared to the level of CLEC3B, the level of ECM1, the level of PON1, and the level of TLN1 in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of VTN, and the level of IGFALS in a sample(s) from the subject; comparing the level of CLEC3B, the level of ECM1, the level of VTN, and the level of IGFALS in the subject sample(s) with a level of CLEC3B, the level of ECM1, the level of VTN, and the level of IGFALS in a control sample(s), wherein a difference in the level of CLEC3B, a difference in the level of ECM1, a difference in the level of VTN, and a difference in the level of IGFALS in the subject sample(s) as compared to the level of CLEC3B, the level of ECM1, the level of VTN, and the level of IGFALS in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of VTN, and the level of IGFALS in a first sample(s) from the subject prior to the initiation of the treatment; determining the level of CLEC3B, the level of ECM1, the level of VTN, and the level of IGFALS in a second sample(s) from the subject after at least a portion of the treatment has been administered; comparing the level of CLEC3B, the level of ECM1, the level of VTN, and the level of IGFALS in the first sample(s) with a level of CLEC3B, the level of ECM1, the level of VTN, and the level of IGFALS in the second sample(s), wherein a difference in the level of CLEC3B, the level of ECM1, the level of VTN, and the level of IGFALS in the first sample(s) as compared to the level of CLEC3B, the level of ECM1, the level of VTN, and the level of IGFALS in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of VTN, and the level of IGFBP3 in a sample(s) from the subject; comparing the level of CLEC3B, the level of ECM1, the level of VTN, and the level of IGFBP3 in the subject sample(s) with a level of CLEC3B, the level of ECM1, the level of VTN, and the level of IGFBP3 in a control sample(s), wherein a difference in the level of CLEC3B, a difference in the level of ECM1, a difference in the level of VTN, and a difference in the level of IGFBP3 in the subject sample(s) as compared to the level of CLEC3B, the level of ECM1, the level of VTN, and the level of IGFBP3 in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of VTN, and the level of IGFBP3 in a first sample(s) from the subject prior to the initiation of the treatment; determining the level of CLEC3B, the level of ECM1, the level of VTN, and the level of IGFBP3 in a second sample(s) from the subject after at least a portion of the treatment has been administered; comparing the level of CLEC3B, the level of ECM1, the level of VTN, and the level of IGFBP3 in the first sample(s) with a level of CLEC3B, the level of ECM1, the level of VTN, and the level of IGFBP3 in the second sample(s), wherein a difference in the level of CLEC3B, the level of ECM1, the level of VTN, and the level of IGFBP3 in the first sample(s) as compared to the level of CLEC3B, the level of ECM1, the level of VTN, and the level of IGFBP3 in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of VTN, and the level of CLU in a sample(s) from the subject; comparing the level of CLEC3B, the level of ECM1, the level of VTN, and the level of CLU in the subject sample(s) with a level of CLEC3B, the level of ECM1, the level of VTN, and the level of CLU in a control sample(s), wherein a difference in the level of CLEC3B, a difference in the level of ECM1, a difference in the level of VTN, and a difference in the level of CLU in the subject sample(s) as compared to the level of CLEC3B, the level of ECM1, the level of VTN, and the level of CLU in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of VTN, and the level of CLU in a first sample(s) from the subject prior to the initiation of the treatment; determining the level of CLEC3B, the level of ECM1, the level of VTN, and the level of CLU in a second sample(s) from the subject after at least a portion of the treatment has been administered; comparing the level of CLEC3B, the level of ECM1, the level of VTN, and the level of CLU in the first sample(s) with a level of CLEC3B, the level of ECM1, the level of VTN, and the level of CLU in the second sample(s), wherein a difference in the level of CLEC3B, the level of ECM1, the level of VTN, and the level of CLU in the first sample(s) as compared to the level of CLEC3B, the level of ECM1, the level of VTN, and the level of CLU in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of VTN, and the level of VWF in a sample(s) from the subject; comparing the level of CLEC3B, the level of ECM1, the level of VTN, and the level of VWF in the subject sample(s) with a level of CLEC3B, the level of ECM1, the level of VTN, and the level of VWF in a control sample(s), wherein a difference in the level of CLEC3B, a difference in the level of ECM1, a difference in the level of VTN, and a difference in the level of VWF in the subject sample(s) as compared to the level of CLEC3B, the level of ECM1, the level of VTN, and the level of VWF in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of VTN, and the level of VWF in a first sample(s) from the subject prior to the initiation of the treatment; determining the level of CLEC3B, the level of ECM1, the level of VTN, and the level of VWF in a second sample(s) from the subject after at least a portion of the treatment has been administered; comparing the level of CLEC3B, the level of ECM1, the level of VTN, and the level of VWF in the first sample(s) with a level of CLEC3B, the level of ECM1, the level of VTN, and the level of VWF in the second sample(s), wherein a difference in the level of CLEC3B, the level of ECM1, the level of VTN, and the level of VWF in the first sample(s) as compared to the level of CLEC3B, the level of ECM1, the level of VTN, and the level of VWF in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of VTN, and the level of SPP2 in a sample(s) from the subject; comparing the level of CLEC3B, the level of ECM1, the level of VTN, and the level of SPP2 in the subject sample(s) with a level of CLEC3B, the level of ECM1, the level of VTN, and the level of SPP2 in a control sample(s), wherein a difference in the level of CLEC3B, a difference in the level of ECM1, a difference in the level of VTN, and a difference in the level of SPP2 in the subject sample(s) as compared to the level of CLEC3B, the level of ECM1, the level of VTN, and the level of SPP2 in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of VTN, and the level of SPP2 in a first sample(s) from the subject prior to the initiation of the treatment; determining the level of CLEC3B, the level of ECM1, the level of VTN, and the level of SPP2 in a second sample(s) from the subject after at least a portion of the treatment has been administered; comparing the level of CLEC3B, the level of ECM1, the level of VTN, and the level of SPP2 in the first sample(s) with a level of CLEC3B, the level of ECM1, the level of VTN, and the level of SPP2 in the second sample(s), wherein a difference in the level of CLEC3B, the level of ECM1, the level of VTN, and the level of SPP2 in the first sample(s) as compared to the level of CLEC3B, the level of ECM1, the level of VTN, and the level of SPP2 in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of VTN, and the level of SELL in a sample(s) from the subject; comparing the level of CLEC3B, the level of ECM1, the level of VTN, and the level of SELL in the subject sample(s) with a level of CLEC3B, the level of ECM1, the level of VTN, and the level of SELL in a control sample(s), wherein a difference in the level of CLEC3B, a difference in the level of ECM1, a difference in the level of VTN, and a difference in the level of SELL in the subject sample(s) as compared to the level of CLEC3B, the level of ECM1, the level of VTN, and the level of SELL in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of VTN, and the level of SELL in a first sample(s) from the subject prior to the initiation of the treatment; determining the level of CLEC3B, the level of ECM1, the level of VTN, and the level of SELL in a second sample(s) from the subject after at least a portion of the treatment has been administered; comparing the level of CLEC3B, the level of ECM1, the level of VTN, and the level of SELL in the first sample(s) with a level of CLEC3B, the level of ECM1, the level of VTN, and the level of SELL in the second sample(s), wherein a difference in the level of CLEC3B, the level of ECM1, the level of VTN, and the level of SELL in the first sample(s) as compared to the level of CLEC3B, the level of ECM1, the level of VTN, and the level of SELL in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of VTN, and the level of LUM in a sample(s) from the subject; comparing the level of CLEC3B, the level of ECM1, the level of VTN, and the level of LUM in the subject sample(s) with a level of CLEC3B, the level of ECM1, the level of VTN, and the level of LUM in a control sample(s), wherein a difference in the level of CLEC3B, a difference in the level of ECM1, a difference in the level of VTN, and a difference in the level of LUM in the subject sample(s) as compared to the level of CLEC3B, the level of ECM1, the level of VTN, and the level of LUM in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of VTN, and the level of LUM in a first sample(s) from the subject prior to the initiation of the treatment; determining the level of CLEC3B, the level of ECM1, the level of VTN, and the level of LUM in a second sample(s) from the subject after at least a portion of the treatment has been administered; comparing the level of CLEC3B, the level of ECM1, the level of VTN, and the level of LUM in the first sample(s) with a level of CLEC3B, the level of ECM1, the level of VTN, and the level of LUM in the second sample(s), wherein a difference in the level of CLEC3B, the level of ECM1, the level of VTN, and the level of LUM in the first sample(s) as compared to the level of CLEC3B, the level of ECM1, the level of VTN, and the level of LUM in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of VTN, and the level of NCAM1 in a sample(s) from the subject; comparing the level of CLEC3B, the level of ECM1, the level of VTN, and the level of NCAM1 in the subject sample(s) with a level of CLEC3B, the level of ECM1, the level of VTN, and the level of NCAM1 in a control sample(s), wherein a difference in the level of CLEC3B, a difference in the level of ECM1, a difference in the level of VTN, and a difference in the level of NCAM1 in the subject sample(s) as compared to the level of CLEC3B, the level of ECM1, the level of VTN, and the level of NCAM1 in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of VTN, and the level of NCAM1 in a first sample(s) from the subject prior to the initiation of the treatment; determining the level of CLEC3B, the level of ECM1, the level of VTN, and the level of NCAM1 in a second sample(s) from the subject after at least a portion of the treatment has been administered; comparing the level of CLEC3B, the level of ECM1, the level of VTN, and the level of NCAM1 in the first sample(s) with a level of CLEC3B, the level of ECM1, the level of VTN, and the level of NCAM1 in the second sample(s), wherein a difference in the level of CLEC3B, the level of ECM1, the level of VTN, and the level of NCAM1 in the first sample(s) as compared to the level of CLEC3B, the level of ECM1, the level of VTN, and the level of NCAM1 in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of VTN, and the level of TLN1 in a sample(s) from the subject; comparing the level of CLEC3B, the level of ECM1, the level of VTN, and the level of TLN1 in the subject sample(s) with a level of CLEC3B, the level of ECM1, the level of VTN, and the level of TLN1 in a control sample(s), wherein a difference in the level of CLEC3B, a difference in the level of ECM1, a difference in the level of VTN, and a difference in the level of TLN1 in the subject sample(s) as compared to the level of CLEC3B, the level of ECM1, the level of VTN, and the level of TLN1 in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of VTN, and the level of TLN1 in a first sample(s) from the subject prior to the initiation of the treatment; determining the level of CLEC3B, the level of ECM1, the level of VTN, and the level of TLN1 in a second sample(s) from the subject after at least a portion of the treatment has been administered; comparing the level of CLEC3B, the level of ECM1, the level of VTN, and the level of TLN1 in the first sample(s) with a level of CLEC3B, the level of ECM1, the level of VTN, and the level of TLN1 in the second sample(s), wherein a difference in the level of CLEC3B, the level of ECM1, the level of VTN, and the level of TLN1 in the first sample(s) as compared to the level of CLEC3B, the level of ECM1, the level of VTN, and the level of TLN1 in the second sample(s) indicates that the treatment is effective, thereby monitoring the effectiveness of a treatment in the subject having latent TB.

In one aspect the present invention provides methods for determining whether a subject exposed to TB will develop latent tuberculosis (TB). The methods include determining the level of CLEC3B, the level of ECM1, the level of PON1, the level of VTN, and the level of one additional marker selected from the group consisting of IGFALS, IGFBP3, CLU, VWF, SPP2, SELL, LUM, NCAM1, and TLN1 in a sample(s) from the subject; comparing the level of CLEC3B, the level of ECM1, the level of PON1, the level of VTN, and the level of VTN, and the level of one additional marker selected from the group consisting of IGFALS, IGFBP3, CLU, VWF, SPP2, SELL, LUM, NCAM1, and TLN1 in the subject sample(s) with a level of CLEC3B, the level of ECM1, the level of PON1, the level of VTN, and the level of one additional marker selected from the group consisting of IGFALS, IGFBP3, CLU, VWF, SPP2, SELL, LUM, NCAM1, and TLN1 in a control sample(s), wherein a difference in the level of CLEC3B, a difference in the level of ECM1, a difference in the level of PON1, a difference in the level of VTN, and a difference in the level of one additional marker selected from the group consisting of IGFALS, IGFBP3, CLU, VWF, SPP2, SELL, LUM, NCAM1, and TLN1 in the subject sample(s) as compared to the level of CLEC3B, the level of ECM1, the level of PON1, the level of VTN, and the level of one additional marker selected from the group consisting of IGFALS, IGFBP3, CLU, VWF, SPP2, SELL, LUM, NCAM1, and TLN1 in the control sample(s) indicates that the subject will develop latent TB, thereby determining whether the subject exposed to TB will develop latent TB.

In one aspect the present invention provides methods for monitoring the effectiveness of a treatment in a subject having latent tuberculosis (TB). The methods include determining the level of CLEC3B, the level of ECM1, the level of PON1, the level of VTN, and the level of one additional marker selected from the group consisting of IGFALS, IGFBP3, CLU, VWF, SPP2, SELL, LUM, NCAM1, and TLN1 in a first sample(s) from the subject prior to the initiation of the treatment; determining the level of CLEC3B, the level of ECM1, the level of PON1, the level of VTN, and the level of one additional marker selected from the group consisting of IGFALS, IGFBP3, CLU, VWF, SPP2, SELL, LUM, NCAM1, and TLN1 in a second sample(s) from the subject after at least a portion of the treatment has been administered; comparing the level of CLEC3B, the level of ECM1, the level of PON1, the level of VTN, and the level of one additional marker selected from the group consisting of IGFALS, IGFBP3, CLU, VWF, SPP2, SELL, LUM, NCAM1, and TLN1 in the first sample(s) with a level of CLEC3B, the level of ECM1, the level of PON1, the level of VTN, and the level of one additional marker selected from the group consisting of IGFALS, IGFBP3, CLU, VWF, SPP2, SELL, LUM, NCAM1, and TLN1 in the second sample(s), wherein a difference in the level of CLEC3B, the level of ECM1, the level of PON1, the level of VTN, and the level of one additional marker selected from the group consisting of IGFALS, IGFBP3, CLU, VWF, SPP2, SELL, LUM, NCAM1, and TLN1 in the first sample(s) as compared to the level of CLEC3B, the level of ECM1, the level of PON1, the level of VTN, and the level of one additional marker selected from the group consisting of IGFALS, IGFBP3, CLU, VWF, SPP2, SELL, LUM, NCAM1, and TLN1 in the second sample(s) indicates that the treatment is effective, thereby monitoring the effectiveness of a treatment in the subject having latent TB.

In one embodiment, the methods further comprise determining the level of one or more additional markers selected from the group consisting of CLEC3B, ECM1, PON1, VTN, IGFALS, IGFBP3, CLU, VWF, SPP2, SELL, LUM, NCAM1, and TLN1, PRG4, CAL SHBG, CPN1, CPN2, QSOX1, PRDX2, APOA1, CA2, LPA, TAGLN2, GPX3, MST1, CNDP1, ATRN, PFN1, PEPD, VASN, BTD, CPB2, GPLD1, DBH, HGFAC, CDH5, LRG1, MASP1, PGLYRP2, TNXB, CD14, CKM, APOE, MAN1A1, PROS1, S100A8, S100A9, HABP2, BCHE, LCAT, PDLIM1, FCN3, ORM1, TGFBI, THBS1, GPS, CD163, VCAM1, LGALS3BP, PTGDS, APOC3, MINPP1, SEPP1, APOA4, MASP2, HYOU1, IGF2, GP1BA, CACNA2D1, CNTN1, NID1, COMP, PCSK9, LCP1 and APOC1.

In another embodiment, the methods further comprise determining the level of one or more additional markers listed in Table 1.

In one aspect, the present invention provides methods of detecting the level of one or more markers listed in Table 1 in a subject. The methods include obtaining subject sample(s) from a human subject exposed to TB; and detecting whether one or more markers listed in Table 1 is present in the subject sample(s). In one embodiment, the methods further comprise determining the level of one or more markers selected from the group consisting of CLEC3B, ECM1, PON1, VTN, IGFALS, IGFBP3, CLU, VWF, SPP2, SELL, LUM, NCAM1, and TLN1.

In one aspect, the present invention provides methods for detecting the level of one or more markers in a subject excposed to TB. The methods include obtaining subject sample(s) from a human subject; and detecting the level of CLEC3B and the level of ECM1 in said subject sample(s). In one embodiment, the methods further comprise determining the level of one or more markers selected from the group consisting of PON1, VTN, IGFALS, IGFBP3, CLU, VWF, SPP2, SELL, LUM, NCAM1, and TLN1 in the subject sample(s).

In one aspect, the present invention provides methods for detecting the level of one or more markers in a subject exposed to TB. The methods include obtaining subject sample(s) from a human subject; and detecting the level of CLEC3B, the level of ECM1, and the level of PON1 in said subject sample(s). In one embodiment, the methods further comprise determining the level of one or more markers selected from the group consisting of IGFALS, IGFBP3, CLU, VWF, SPP2, SELL, LUM, NCAM1, and TLN1 in the subject sample(s).

In one aspect, the present invention provides methods for detecting the level of one or more markers in a subject exposed to TB. The methods include obtaining subject sample(s) from a human subject; and detecting the level of CLEC3B, the level of ECM1, and the level of VTN in said subject sample(s). In one embodiment, the methods further comprise determining the level of one or more markers selected from the group consisting of IGFALS, IGFBP3, CLU, VWF, SPP2, SELL, LUM, NCAM1, and TLN1 in the subject sample(s).

In one aspect, the present invention provides methods for detecting the level of one or more markers in a subject exposed to TB. The methods include obtaining subject sample(s) from a human subject; and detecting the level of CLEC3B, the level of ECM1, the level of PON1, and the level of VTN in said subject sample(s). In one embodiment, the methods further comprise determining the level of one or more markers selected from the group consisting of IGFALS, IGFBP3, CLU, VWF, SPP2, SELL, LUM, NCAM1, and TLN1 in the subject sample(s).

In one embodiment, the methods further comprise detecting the level of one or more markers listed in Table 1 in a sample(s) from the subject.

In one embodiment, the methods further comprise administering to the subject an effective amount of a therapeutic agent for treating TB, thereby treating latent TB in the subject. In one embodiment, the therapeutic agent modulates the level and/or activity of any one or more of the markers listed in Table 1.

In one aspect, the present invention provides kits for determining whether a subject exposed to tuberculosis (TB) will develop latent TB. The kits include reagents for determining the level of one or more markers listed in Table 1 in a subject sample(s) and instructions for use of the kit to determine whether the subject will develop latent TB.

In one aspect, the present invention provides kits monitoring the effectiveness of a treatment in a subject having latent TB. The kits include reagents for determining the level of one or more markers listed in Table 1 in a subject sample(s) and instructions for use of the kit to monitor the effectiveness of the treatment.

In one embodiment, the kits further comprise reagents for determining the level of one or more markers selected from the group consisting of CLEC3B, ECM1, PON1, VTN, IGFALS, IGFBP3, CLU, VWF, SPP2, SELL, LUM, NCAM1, and TLN1 in the subject sample(s).

In one aspect, the present invention provides kits for determining whether a subject exposed to tuberculosis (TB) will develop latent TB. The kits include reagents for determining the level of CLEC3B and the level of ECM1 in a subject sample(s) and instructions for use of the kit to determine whether the subject will develop latent TB. In one embodiment, the kits further comprise reagents for determining the level of one or more markers selected from the group consisting of PON1, VTN, IGFALS, IGFBP3, CLU, VWF, SPP2, SELL, LUM, NCAM1, and TLN1 in the subject sample(s).

In one aspect, the present invention provides kits monitoring the effectiveness of a treatment in a subject having latent TB. The kits include reagents for determining the level of CLEC3B and the level of ECM1 in a subject sample(s) and instructions for use of the kit to monitor the effectiveness of the treatment. In one embodiment, the kits further comprise reagents for determining the level of one or more markers selected from the group consisting of PON1, VTN, IGFALS, IGFBP3, CLU, VWF, SPP2, SELL, LUM, NCAM1, and TLN1 in the subject sample(s).

In one aspect, the present invention provides kits for determining whether a subject exposed to tuberculosis (TB) will develop latent TB. The kits include reagents for determining the level of CLEC3B, the level of ECM1, and the level of PON1 in a subject sample(s) and instructions for use of the kit to determine whether the subject will develop latent TB. In one embodiment, the kits further comprise reagents for determining the level of one or more markers selected from the group consisting of IGFALS, IGFBP3, CLU, VWF, SPP2, SELL, LUM, NCAM1, and TLN1 in the subject sample(s).

In one aspect, the present invention provides kits monitoring the effectiveness of a treatment in a subject having latent TB. The kits include reagents for determining the level of CLEC3B, the level of ECM1, and the level of PON1 in a subject sample(s) and instructions for use of the kit to monitor the effectiveness of the treatment. In one embodiment, the kits further comprise reagents for determining the level of one or more markers selected from the group consisting of IGFALS, IGFBP3, CLU, VWF, SPP2, SELL, LUM, NCAM1, and TLN1 in the subject sample(s).

In one aspect, the present invention provides kits for determining whether a subject exposed to tuberculosis (TB) will develop latent TB. The kits include reagents for determining the level of CLEC3B, the level of ECM1, and the level of VTN in a subject sample(s) and instructions for use of the kit to determine whether the subject will develop latent TB. In one embodiment, the kits further comprise reagents for determining the level of one or more markers selected from the group consisting of IGFALS, IGFBP3, CLU, VWF, SPP2, SELL, LUM, NCAM1, and TLN1 in the subject sample(s).

In one aspect, the present invention provides kits monitoring the effectiveness of a treatment in a subject having latent TB. The kits include reagents for determining the level of CLEC3B, the level of ECM1, and the level of VTN in a subject sample(s) and instructions for use of the kit to monitor the effectiveness of the treatment. In one embodiment, the kits further comprise reagents for determining the level of one or more markers selected from the group consisting of IGFALS, IGFBP3, CLU, VWF, SPP2, SELL, LUM, NCAM1, and TLN1 in the subject sample(s).

In one aspect, the present invention provides kits for determining whether a subject exposed to tuberculosis (TB) will develop latent TB. The kits include reagents for determining the level of CLEC3B, the level of ECM1, the level of PON1, and the level of VTN in a subject sample(s) and instructions for use of the kit to determine whether the subject will develop latent TB. In one embodiment, the kits further comprise reagents for determining the level of one or more markers selected from the group consisting of IGFALS, IGFBP3, CLU, VWF, SPP2, SELL, LUM, NCAM1, and TLN1 in the subject sample(s).

In one aspect, the present invention provides kits monitoring the effectiveness of a treatment in a subject having latent TB. The kits include reagents for determining the level of CLEC3B, the level of ECM1, the level of PON1, and the level of VTN in a subject sample(s) and instructions for use of the kit to monitor the effectiveness of the treatment. In one embodiment, the kits further comprise reagents for determining the level of one or more markers selected from the group consisting of IGFALS, IGFBP3, CLU, VWF, SPP2, SELL, LUM, NCAM1, and TLN1 in the subject sample(s).

In one embodiment, the kits further comprise reagents for determining the level of one or more markers listed in Table 1 in a sample(s) from the subject.

In one aspect, the present invention provides kits for determining whether a subject exposed to TB will develop latent tuberculosis (TB). The kits include reagents for determining the level of CLEC3B, the level of ECM1, the level of PON1, and the level of IGFALS in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of PON1, and the level of IGFALS in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of PON1, and the level of IGFBP3 in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of PON1, and the level of IGFBP3 in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of PON1, and the level of CLU in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of PON1, and the level of CLU in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of PON1, and the level of VWF in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of PON1, and the level of VWF in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of PON1, and the level of SPP2 in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of PON1, and the level of SPP2 in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of PON1, and the level of SELL in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of PON1, and the level of SELL in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of PON1, and the level of LUM in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of PON1, and the level of LUM in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of PON1, and the level of NCAM1 in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of PON1, and the level of NCAM1 in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of PON1, and the level of TLN1 in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of PON1, and the level of TLN1 in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of VTN, and the level of IGFALS in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of VTN, and the level of IGFALS in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of VTN, and the level of IGFBP3 in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of VTN, and the level of IGFBP3 in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of VTN, and the level of CLU in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of VTN, and the level of CLU in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of VTN, and the level of VWF in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of VTN, and the level of VWF in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of VTN, and the level of SPP2 in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of VTN, and the level of SPP2 in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of VTN, and the level of SELL in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of VTN, and the level of SELL in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of VTN, and the level of LUM in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of VTN, and the level of LUM in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of VTN, and the level of NCAM1 in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of VTN, and the level of NCAM1 in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of VTN, and the level of TLN1 in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of VTN, and the level of TLN1 in a subject sample(s) and instructions for use of the kit to monitor the effectiveness of the treatment.

In one aspect, the present invention provides kits for determining whether a subject exposed to TB will develop latent tuberculosis (TB). The kits include reagents for determining the level of CLEC3B, the level of ECM1, the level of PON1, the level of VTN, and the level of one additional marker selected from the group consisting of IGFALS, IGFBP3, CLU, VWF, SPP2, SELL, LUM, NCAM1, and TLN1 in a sample(s) from the subject and instructions for use of the kit to determine whether the subject will develop latent TB.

In one aspect, the present invention provides kits monitoring the effectiveness of a treatment in a subject having latent TB. The kits include reagents for determining the level of CLEC3B, the level of ECM1, the level of PON1, the level of VTN, and the level of one additional marker selected from the group consisting of IGFALS, IGFBP3, CLU, VWF, SPP2, SELL, LUM, NCAM1, and TLN1 in a subject sample(s) and instructions for use of the kit to monitor the effectiveness of the treatment.

In one embodiment, the kits further comprise reagents for determining the level of any one or more of the markers listed in Table 1 in a sample(s) from the subject.

In one embodiment, the kits further comprise reagents for determining the level of one or more additional markers selected from the group consisting of IGFALS, IGFBP3, CLU, VWF, SPP2, SELL, LUM, NCAM1, and TLN1, PRG4, CAL SHBG, CPN1, CPN2, QSOX1, PRDX2, APOA1, CA2, LPA, TAGLN2, GPX3, MST1, CNDP1, ATRN, PFN1, PEPD, VASN, BTD, CPB2, GPLD1, DBH, HGFAC, CDH5, LRG1, MASP1, PGLYRP2, TNXB, CD14, CKM, APOE, MAN1A1, PROS1, S100A8, S100A9, HABP2, BCHE, LCAT, PDLIM1, FCN3, ORM1, TGFBI, THBS1, GPS, CD163, VCAM1, LGALS3BP, PTGDS, APOC3, MINPP1, SEPP1, APOA4, MASP2, HYOU1, IGF2, GP1BA, CACNA2D1, CNTN1, NID1, COMP, PCSK9, LCP1 and APOC1 in a sample(s) from the subject.

In one aspect, the present invention provides methods for determining whether a subject exposed to TB will develop latent tuberculosis (TB). The methods include determining the level of each marker in any one of the combination of markers set forth in any one of Tables 2, 3, 4, and 5 in a sample(s) from the subject; comparing the level of each of the markers of the combination in the subject sample(s) with a level of each of the markers of the combination in a control sample(s), wherein a difference in the level of all of the markers of the combination in the subject sample(s) as compared to the level of all of the markers of the combination in the control sample(s) indicates that the subject will develop latent TB.

In one aspect, the present invention provides methods for monitoring the effectiveness of a treatment in a subject having latent tuberculosis (TB). The methods include determining the level of any one of the combination of markers set forth in any one of Tables 2, 3, 4, and 5 in a first sample(s) from the subject prior to the initiation of the treatment; determining the level of each of the markers of the combination in a second sample(s) from the subject after at least a portion of the treatment has been administered; comparing the level of each of the markers of the combination in the first sample(s) with a level of each of the markers of the combination in the second sample(s), wherein a difference in the level of all of the markers of the combination in the first sample(s) as compared to the level of all of the markers of the combination in the second sample(s) indicates that the treatment is effective.

In one embodiment, the combination of markers has an area under the curve (AUC) of about 0.85 to about 1.00.

In one aspect, the present invention provides kits for determining whether a subject exposed to TB will develop latent tuberculosis (TB). The kits include reagents for determining the level of each marker in any one of the combination of markers set forth in any one of Tables 2, 3, 4, and 5 in a subject sample(s) and instructions for use of the kit to determine whether the subject will develop latent TB.

In one aspect, the present invention provides kits for monitoring the effectiveness of a treatment in a subject having latent TB. The kits include reagents for determining the level of each marker in any one of the combination of markers set forth in any one of Tables 2, 3, 4, and 5 in a subject sample(s) and instructions for use of the kit to monitor the effectiveness of the treatment.

In one embodiment, the combination of markers has an area under the curve (AUC) of about 0.85 to about 1.00.

BRIEF DESCRIPTION OF THE DRAWINGS

FIG. 1 is a table showing the characteristics of included subjects by study phase and clinical cohort. Patients for this study were enrolled in the Kawempe Community Health Study (KCHS), a prospective cohort of adult pulmonary TB index cases and their household contacts, conducted in Kampala, Uganda. Plasma or serum was collected at baseline from these subjects and at regular time points thereafter. Index cases were adults (age 18 years and older) with initial episodes of newly diagnosed culturepositive pulmonary TB. Household contacts were a person (age 12 years and older) living in the same building as an index case for at least one week during the three-month period immediately preceding the index case diagnosis. After the initial evaluation, participants were evaluated at 3, 6, 12, and 24 months for active TB and with repeat TST if their first and subsequent TST remained negative. All individuals were monitored clinically and if signs and symptoms of TB developed, evaluated as TB suspects. Tuberculin skin testing was done using 5 TU of purified protein derivative (PPD). All subjects were HIV−.

FIG. 2A is a table depicting the cross-sectional comparison of changes in the level of the indicated markers in sera from non-infected (NI), baseline TST-negative future converters (CO), baseline TST-positive (LTBI), and active TB (ATB) groups. Shown are protein expression change ratios (also referred to herein as differential intensity ratios, or DI). The significant changes (p<0.05) are shaded in dark and medium dark gray for increased expression ratios and the the significant changes (p<0.05) are shaded in light or medium light gray for decreases expression ratios. Most protein changes associated with inflammation, immune response, tissue repair, cellular migration and proliferation were observed in subjects with active TB. Early in disease smaller changes were observed in these processes, as well as changes in proteins associated with lipid metabolism and the innate immune response. The results are consistent with low level of distinct observable changes early in disease.

FIG. 2B is a another table depicting the cross-sectional comparison of changes in the level of the indicated markers in sera from non-infected (NI), baseline TST-negative future converters (CO), baseline TST-positive (LTBI), and active TB (ATB) groups. Shown are protein expression change ratios (also referred to herein as differential intensity ratios, or DI). The significant changes (p<0.05) are shaded in dark and medium dark gray for increased expression ratios and the the significant changes (p<0.05) are shaded in light or medium light gray for decreases expression ratios. Most protein changes associated with inflammation, immune response, tissue repair, cellular migration and proliferation were observed in subjects with active TB. Early in disease smaller changes were observed in these processes, as well as changes in proteins associated with lipid metabolism and the innate immune response. The results are consistent with low level of distinct observable changes early in disease.

FIG. 2C is a another table depicting the cross-sectional comparison of changes in the level of the indicated markers in sera from non-infected (NI), baseline TST-negative future converters (CO), baseline TST-positive (LTBI), and active TB (ATB) groups. Shown are protein expression change ratios (also referred to herein as differential intensity ratios, or DI). The significant changes (p<0.05) are shaded in dark and medium dark gray for increased expression ratios and the the significant changes (p<0.05) are shaded in light or medium light gray for decreases expression ratios. Most protein changes associated with inflammation, immune response, tissue repair, cellular migration and proliferation were observed in subjects with active TB. Early in disease smaller changes were observed in these processes, as well as changes in proteins associated with lipid metabolism and the innate immune response. The results are consistent with low level of distinct observable changes early in disease.

FIG. 2D is a another table depicting the cross-sectional comparison of changes in the level of the indicated markers in sera from non-infected (NI), baseline TST-negative future converters (CO), baseline TST-positive (LTBI), and active TB (ATB) groups. Shown are protein expression change ratios (also referred to herein as differential intensity ratios, or DI). The significant changes (p<0.05) are shaded in dark and medium dark gray for increased expression ratios and the the significant changes (p<0.05) are shaded in light or medium light gray for decreases expression ratios. Most protein changes associated with inflammation, immune response, tissue repair, cellular migration and proliferation were observed in subjects with active TB. Early in disease smaller changes were observed in these processes, as well as changes in proteins associated with lipid metabolism and the innate immune response. The results are consistent with low level of distinct observable changes early in disease.

FIG. 3A is a table depicting the longitudinal comparison of changes in selected* plasma proteins from baseline TST-negative subjects (N=52) that converted to TST-positive (N=37) or remained TST-negative (N=15). Shown are protein expression change ratios (also referred to herein as differential intensity ratios, or DI) between each individual's baseline TST-negative sample and the TST-positive conversion sample or corresponding TST-negative sample. The significant changes (p<0.05) are shaded in dark and medium dark gray for increased expression ratios and the the significant changes (p<0.05) are shaded in light or medium light gray for decreases expression ratios. *159 proteins from the cross-sectional discovery phase using the following combination of biological and statistical criteria. All of the significantly differentially expressed proteins from the baseline converter vs NI and LTBI vs NI comparisons were selected along with the most differentially expressed proteins from comparisons to active TB. Also included were the significant proteins described in the MRM-MS assay of U.S. Patent Publication No. 2016/0154005 (incorporated herein in its entirety by reference) and Achkar, et al. (2015 *EBioMedicine*, 2, 1160-8).

FIG. 3B is also a table depicting the longitudinal comparison of changes in selected* plasma proteins from baseline TST-negative subjects (N=52) that converted to TST-positive (N=37) or remained TST-negative (N=15). Shown are protein expression change ratios (also referred to herein as differential intensity ratios, or DI) between each individual's baseline TST-negative sample and the TST-positive conversion sample or corresponding TST-negative sample. The significant changes (p<0.05) are shaded in dark and medium dark gray for increased expression ratios and the the significant changes (p<0.05) are shaded in light or medium light gray for decreases expression ratios. *159 proteins from the cross-sectional discovery phase using the following combination of biological and statistical criteria. All of the significantly differentially expressed proteins from the baseline converter vs NI and LTBI vs NI comparisons were selected along with the most differentially expressed proteins from comparisons to active TB. Also included were the significant proteins described in the MRM-MS assay of U.S. Patent Publication No. 2016/0154005 (incorporated herein in its entirety by reference) and Achkar, et al. (2015 *EBioMedicine*, 2, 1160-8).

FIG. 4A is a table showing changes in plasma protein expression after TST-positive conversion. Shown are protein expression change ratios (also referred to herein as differential intensity ratios, or DI) in subjects (N=19) with samples at baseline (D1), 3 months (M3), and 6 months (M6) that had converted to TST-positive at M3. The significant changes (p<0.05) are shaded in dark and medium dark gray for increased expression ratios and the the significant changes (p<0.05) are shaded in light or medium light gray for decreases expression ratios.

FIG. 4B is also a table showing changes in plasma protein expression after TST-positive conversion. Shown are protein expression change ratios (also referred to herein as differential intensity ratios, or DI) in subjects (N=19) with samples at baseline (D1), 3 months (M3), and 6 months (M6) that had converted to TST-positive at M3. The significant changes (p<0.05) are shaded in dark and medium dark gray for increased expression ratios and the the significant changes (p<0.05) are shaded in light or medium light gray for decreases expression ratios.

DETAILED DESCRIPTION OF THE INVENTION

The present invention is based, at least in part, on the discovery of markers that are associated with latent tuberculosis (TB). In particular, biomarkers associated with latent TB have been discovered, prioritized, and validated in relevant in vitro experimental systems. The markers were identified as being expressed, e.g., essentially specifically expressed, in samples from subjects exposed to TB and developing latent TB as compared to noninfected subjects, subjects having active TB infection, or subjects who convert to TB infection during the study.

Accordingly, the present invention provides sensitive and facile methods and kits for determining whether a subject exposed to TB will develop latent TB, and methods and kits for monitoring the effectiveness of a therapy for treating a subject having latent TB.

Various aspects of the invention are described in further detail in the following subsections:

I. Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "marker" or "biomarker" is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median level, e.g., expression level, of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for, e.g., disease (prognostics and diagnostics), therapeutic effectiveness of a drug (theranostics) and of drug toxicity.

In some embodiments, the accuracy of a marker(s) useful in the compositions and methods of the present invention may be characterized by a Receiver Operating Characteristic curve ("ROC curve"). An ROC is a plot of the true positive rate against the false positive rate for the different possible cutpoints of a diagnostic marker(s). An ROC curve shows the relationship between sensitivity and specificity. That is, an increase in sensitivity will be accompanied by a decrease in specificity. The closer the curve follows the left axis and then the top edge of the ROC space, the more accurate the marker(s). Conversely, the closer the curve comes to the 45-degree diagonal of the ROC graph, the less accurate the marker(s). The area under the ROC is a measure of a marker(s) accuracy. The accuracy of the marker(s) depends on how well the marker(s) separates the group being tested into those with and without the disease in question. An area under the curve (referred to as "AUC") of 1 represents a perfect marker(s), while an area of 0.5 represents a less useful marker(s). Thus, in some embodiments, biomarker(s) and methods of the present invention have an AUC greater than about 0.50, an AUC greater than about 0.60, or an AUC greater than about 0.70.

"Tuberculosis" ("TB") is a multisystemic disease with myriad presentations and manifestations, and is the most common cause of infectious disease-related mortality worldwide. *Mycobacterium tuberculosis*, a tubercle *bacillus*, is the causative agent of TB. The lungs are the most common site for the development of TB (pulmonary TB), and about 85% of patients with TB present with pulmonary complaints. Nonetheless, "extrapulmonary TB", e.g., "disseminated TB", can occur as part of a primary or late, generalized infection. Extrapulmonary TB can affect bones and joints, bronchus, eye, intestines, larynx, peritoneum, meninges, pericardium, lymph node, organs of the male or female urinary and reproductive systems, skin, stomach, and/or urinary systems.

When a person is infected with *M tuberculosis*, the infection can take one of a variety of paths, most of which do not lead to actual TB. The infection may be cleared by the host immune system or suppressed into an inactive form called "latent tuberculosis infection", with resistant hosts controlling mycobacterial growth at distant foci before the development of active disease.

A subject has "latent tuberculosis ("LTB") (also referred to as "latent tuberculosis infection" ("LTBI")) when the subject is infected with *Mycobacterium tuberculosis* but does not have active tuberculosis disease. Subjects having latent tuberculosis are not infectious. The main risk is that approximately 10% of these patients (5% in the first two years after infection and 0.1% per year thereafter but higher risk if immunosuppressed) will go on to develop "active tuberculosis" ("active TB") and spread the disease at a later stage of their life if, for example, there is onset of a disease affecting the immune system (such as AIDS) or a disease whose treatment affects the immune system (e.g., chemotherapy in cancer or systemic steroids in asthma or Enbrel, Humira or Orencia in rheumatoid arthritis); malnutrition (which may be the result of illness or injury affecting the digestive system, or of a prolonged period of not eating, or disturbance in food availability such as famine, residence in refugee camp or concentration camp, or civil war; and/or degradation of the immune system due to aging.

"Miliary tuberculosis" (also known as "disseminated tuberculosis", "tuberculosis cutis *acuta* generalisata", and "Tuberculosis cutis disseminata") is a form of tuberculosis that is characterized by a wide dissemination into the human body and by the tiny size of the lesions (1-5 mm) Miliary tuberculosis is characterized by a chronic and contagious *Mycobacterium tuberculosis* infection that has spread to other organs of the body by the blood or lymph system. Its name comes from a distinctive pattern seen on a chest X-ray of many tiny spots distributed throughout the lung fields with the appearance similar to millet seeds—thus the term "miliary" tuberculosis. Miliary TB may infect any number of organs, including, for example, the lungs, liver, and spleen. Disseminated disease can occur within weeks of the primary infection, or may lie inactive for years before causing illness. Infants, the elderly, those infected with HIV, and those who take immune-suppressing medications are at higher risk for disseminated TB, because of their weaker immune systems.

The symptoms of a subject having TB are similar to the symtoms of a subject having an "other respiratory disease" or "ORD", such a pneumonia, and include, for example, cough (e.g., coughing that lasts three or more weeks, coughing up blood or sputum, chest pain, or pain with breathing or coughing), unintentional weight loss, fatigue, fever, night sweats, chills, and/or loss of appetite.

Methods to diagnose a subject as having active and/or latent TB are known in the art. The primary screening method for TB infection (active or latent) is the Mantoux tuberculin skin test with purified protein derivative (PPD). An in vitro blood test based on interferon-gamma release assay (IGRA) with antigens specific for *M. tuberculosis* can also be used to screen for latent TB infection. Chest X-rays and culturing of sputum samples may also be used.

A subject having latent TB usually has a skin test or blood test result indicating TB infection; has a normal chest x-ray and a negative sputum test; has TB bacteria in his/her body that are alive, but inactive; does not feel sick (e.g. does not have a cough and/or fever); and cannot spread TB bacteria to others. A subject having active TB ususally has a positive skin test or tuberculosis blood test, may have an abnormal chest x-ray, or positive sputum smear or culture; has overt indications of illness (e.g., cough and/or fever), and can spread the disease to others.

A "level of a marker" or "the level of a biomarker" refers to an amount of a marker present in a sample being tested. A level of a marker may be either in absolute level or amount (e.g., µg/ml) or a relative level or amount (e.g., relative intensity of signals).

A "higher level" or an "increase in the level" of marker refers to a level of a marker in a test sample that is greater than the standard error of the assay employed to assess the level of the marker, and is preferably at least twice, and more preferably three, four, five, six, seven, eight, nine, or ten or more times the level of marker in a control sample (e.g., a sample from a subject who is not infected with TB, a subject who has been exposed to TB but is asymptomatic, a subject having active TB, a subject having an ORD, and/or the average level of the marker in several control samples).

A "lower level" or a "decrease in the level" of a marker refers to a level of the marker in a test sample that is less than the standard error of the assay employed to assess the level of the marker, and preferably at least twice, and more preferably three, four, five, six, seven, eight, nine, or ten or more times less than the level of the marker in a control sample (e.g., a sample from a subject who is not infected with TB, a subject who has been exposed to TB but is asymptomatic, a subject having active TB, a subject having an ORD, and/or the average level of the marker in several control samples).

The term "known standard level" or "control level" refers to an accepted or pre-determined level of a marker which is used to compare the level of the marker in a sample derived from a subject. In one embodiment, the control level of a marker is based on the level of the marker in a sample(s) from a subject(s) who is not infected with TB. In one embodiment, the control level of a marker is based on the level of the marker in a sample(s) from a subject(s) who has been exposed to TB, but is asymptomatic (does not present any TB symptoms). In one embodiment, the control level of a marker is based on the level of the marker in a sample(s) from a subject(s) who converted to latent infection 3 months after a sample was collected. In one embodiment, the control level of a marker is based on the level of the marker in a sample(s) from a subject(s) having active TB. In one embodiment, the control level of a marker is based on the level of the marker in a sample(s) from a subject(s) having latent TB. In another embodiment, the control level of a marker is based on the level of the marker in a sample(s) from a subject(s) having an ORD. In one embodiment, the control level of a marker in a sample from a subject is a level of the marker previously determined in a sample(s) from the subject. In yet another embodiment, the control level of a marker is based on the level of the marker in a sample from a subject(s) prior to the administration of a therapy for TB. In another embodiment, the control level of a marker is based on the level of the marker in a sample(s) from a subject(s) having latent TB that is not contacted with a test compound. In another embodiment, the control level of a marker is based on the level of the marker in a sample(s) from a subject(s) having active TB that is not contacted with a test compound. In another embodiment, the control level of a marker is based on the level of the marker in a sample(s) from a subject(s) having latent TB that is contacted with a test compound. In another embodiment, the control level of a marker is based on the level of the marker in a sample(s) from a subject(s) having active TB that is contacted with a test compound. In one embodiment, the control level of a marker is based on the expression level of the marker in a sample(s) from an animal model of TB, a cell, or a cell line derived from the animal model of TB.

Alternatively, and particularly as further information becomes available as a result of routine performance of the methods described herein, population-average values for "control" level of expression of a marker may be used. In other embodiments, the "control" level of a marker may be determined by determining the level of a marker in a subject sample obtained from a subject before the onset of latent TB, from archived subject samples, and the like.

As used herein, the terms "patient" or "subject" refer to human and non-human animals, e.g., veterinary patients. The term "non-human animal" includes all vertebrates, e.g., mammals and non-mammals, such as non-human primates, mice, rabbits, sheep, dog, cat, horse, cow, chickens, amphibians, and reptiles. In one embodiment, the subject is a human, e.g., a pediatric and adult human.

The term "sample" as used herein refers to a collection of similar cells or tissue isolated from a subject, as well as tissues, cells and fluids present within a subject. The term "sample" includes any body fluid (e.g., blood fluids, lymph, gynecological fluids, cystic fluid, urine, ocular fluids and fluids collected by bronchial lavage and/or peritoneal rinsing), or a cell from a subject. In one embodiment, the tissue or cell is removed from the subject. In another embodiment, the tissue or cell is present within the subject. Other subject samples include tear drops, serum, cerebrospinal fluid, feces, sputum and cell extracts. In one embodiment the sample is a blood sample. In another embodiment, the sample is a serum sample. In one embodiment, the biological sample contains protein molecules from the test subject. In another embodiment, the biological sample may contain mRNA molecules from the test subject or genomic DNA molecules from the test subject.

The term "determining" means methods which include detecting the presence or absence of marker(s) in the sample, quantifying the amount of marker(s) in the sample, and/or qualifying the type of biomarker. Measuring can be accomplished by methods known in the art and those further described herein.

As used herein, the various forms of the term "modulate" are intended to include stimulation (e.g., increasing or upregulating a particular response or activity) and inhibition (e.g., decreasing or downregulating a particular response or activity).

A kit is any manufacture (e.g. a package or container) comprising at least one reagent, e.g. a probe, a primer, or an antibody, for specifically detecting a marker of the invention, the manufacture being promoted, distributed, or sold as a unit for performing the methods of the present invention. In certain embodiments, a kit may include a substrate, e.g., a substrate comprising a capture reagent for one or more markers of the invention and/or a capture reagent bound to one or more markers of the invention. In some embodiments, such kits comprise instructions for determining the level of a marker(s) using mass spectrometry.

II. Markers of the Invention

The present invention is based upon the discovery of markers that are essentially specifically expressed in samples from subjects having latent tuberculosis (TB) (Table 1). These markers have been shown to be differentially present in samples of subjects exposed to TB having latent TB and control subjects.

Accordingly, the level of any one marker or any combination of markers listed in Table 1 and found in a test sample compared to a control, or the presence or absence of one marker or combination of markers listed in Table 1 in the test sample may be used in the methods and kits of the present invention.

The nucleotide and amino acid sequences of the markers are known in the art and may be found in, for example, the GenBank Accession numbers listed in Table 1, the entire contents of which are incorporated herein by reference.

TABLE 1

Markers of the Invention.

| Marker Name | Protein Description | UNIPROT_ID | UNIPROT ACCESSION | GENBANK ACCESSION |
|---|---|---|---|---|
| ORM1 | Alpha-1-acid glycoprotein 1 precursor | A1AG1_HUMAN | P02763 | NP_000598.2 NM_000607.2 |
| LRG1 | Leucine-rich alpha-2-glycoprotein precursor | A2GL_HUMAN | P02750 | NP_443204.1 NM_052972.2 |
| IGFALS | Insulin-like growth factor-binding protein complex acid labile subunit precursor | ALS_HUMAN | P35858 | NP_001139478.1 NP_004961.1 NM_001146006.1 NM_004970.2 |
| LPA | Apolipoprotein(a) precursor | APOA_HUMAN | P08519 | NP_005568.2 NM_005577.2 |
| APOA1 | Apolipoprotein A-I precursor | APOA1_HUMAN | P02647 | NP_000030.1 NM_000039.1 |
| APOA4 | Apolipoprotein A-IV precursor | APOA4_HUMAN | P06727 | NP_000473.2 NM_000482.3 |
| APOC1 | Apolipoprotein C-I precursor | APOC1_HUMAN | P02654 | NP_001636.1 NM_001645.3 |
| APOC3 | Apolipoprotein C-III precursor | APOC3_HUMAN | P02656 | NP_000031.1 NM_000040.1 |
| APOE | Apolipoprotein E precursor | APOE_HUMAN | P02649 | NP_000032.1 NM_000041.2 |

TABLE 1-continued

Markers of the Invention.

| Marker Name | Protein Description | UNIPROT_ID | UNIPROT ACCESSION | GENBANK ACCESSION |
|---|---|---|---|---|
| ATRN | Attractin precursor | ATRN_HUMAN | O75882 | NP_001193976.1<br>NP_647537.1<br>NP_647538.1<br>NM_001207047.1<br>NM_139321.2<br>NM_139322.2 |
| TGFBI | Transforming growth factor-beta-induced protein ig-h3 precursor | BGH3_HUMAN | Q15582 | NP_000349.1<br>NM_000358.2 |
| BTD | Biotinidase precursor | BTD_HUMAN | P43251 | NP_000051.1<br>NM_000060.2 |
| CD163 | Scavenger receptor cysteine-rich type 1 protein M130 precursor | C163A_HUMAN | Q86VB7 | NP_004235.4<br>NP_981961.2<br>NM_004244.5<br>NM_203416.3 |
| CACNA2D1 | Voltage-dependent calcium channel subunit alpha-2/delta-1 precursor | CA2D1_HUMAN | P54289 | NP_000713.2<br>NM_000722.2 |
| CDH5 | Cadherin-5 precursor | CADH5_HUMAN | P33151 | NP_001786.2<br>NM_001795.3 |
| CA1 | Carbonic anhydrase 1 | CAH1_HUMAN | P00915 | NP_001122301.1<br>NP_001122302.1<br>NP_001122303.1<br>NP_001158302.1<br>NP_001729.1<br>NM_001128829.2<br>NM_001128830.2<br>NM_001128831.2<br>NM_001164830.1<br>NM_001738.3 |
| CA2 | Carbonic anhydrase 2 | CAH2_HUMAN | P00918 | NP_000058.1<br>NM_000067.2 |
| CPB2 | Carboxypeptidase B2 precursor | CBPB2_HUMAN | Q96IY4 | NP_001863.2<br>NM_001872.3 |
| CPN1 | Carboxypeptidase N catalytic chain precursor | CBPN_HUMAN | P15169 | NP_001299.1<br>NM_001308.2 |
| CD14 | Monocyte differentiation antigen CD14 precursor | CD14_HUMAN | P08571 | NP_000582.1<br>NP_001035110.1<br>NP_001167575.1<br>NP_001167576.1<br>NM_000591.3<br>NM_001040021.2<br>NM_001174104.1<br>NM_001174105.1 |
| BCHE | Cholinesterase precursor | CHLE_HUMAN | P06276 | NP_000046.1<br>NM_000055.2 |
| CLU | Clusterin precursor | CLUS_HUMAN | P10909 | NP_001822.3<br>NM_001831.3 |
| CNDP1 | Beta-Ala-His dipeptidase precursor | CNDP1_HUMAN | Q96KN2 | NP_116038.4<br>NM_032649.5 |
| CNTN1 | Contactin-1 precursor | CNTN1_HUMAN | Q12860 | NP_001242992.1<br>NP_001242993.1<br>NP_001834.2<br>NP_778203.1<br>NM_001256063.1<br>NM_001256064.1<br>NM_001843.3<br>NM_175038.2 |
| COMP | Cartilage oligomeric matrix protein precursor | COMP_HUMAN | P49747 | NP_000086.2<br>NM_000095.2 |
| CPN2 | Carboxypeptidase N subunit 2 precursor | CPN2_HUMAN | P22792 | NP_001073982.2<br>NM_001080513.2 |
| DBH | Dopamine beta-hydroxylase | DOPO_HUMAN | P09172 | NP_000778.3<br>NM_000787.3 |
| ECM1 | Extracellular matrix protein 1 precursor | ECM1_HUMAN | Q16610 | NP_001189787.1<br>NP_004416.2<br>NP_073155.2<br>NM_001202858.1<br>NM_004425.3<br>NM_022664.2 |
| FCN3 | Ficolin-3 precursor | FCN3_HUMAN | O75636 | NP_003656.2<br>NP_775628.1<br>NM_003665.2<br>NM_173452.1 |

TABLE 1-continued

Markers of the Invention.

| Marker Name | Protein Description | UNIPROT_ID | UNIPROT ACCESSION | GENBANK ACCESSION |
|---|---|---|---|---|
| GP1BA | Platelet glycoprotein Ib alpha chain precursor | GP1BA_HUMAN | P07359 | NP_000164.5<br>NM_000173.5 |
| GP5 | Platelet glycoprotein V precursor | GPV_HUMAN | P40197 | NP_004479.1<br>NM_004488.2 |
| GPX3 | Glutathione peroxidase 3 precursor | GPX3_HUMAN | P22352 | NP_002075.2<br>NM_002084.3 |
| HABP2 | Hyaluronan-binding protein 2 precursor | HABP2_HUMAN | Q14520 | NP_001171131.1<br>NP_004123.1<br>NM_001177660.1<br>NM_004132.3 |
| HGFAC | Hepatocyte growth factor activator precursor | HGFA_HUMAN | Q04756 | NP_001519.1<br>NM_001528.2 |
| MST1 | Hepatocyte growth factor-like protein precursor | HGFL_HUMAN | P26927 | NP_066278.3<br>NM_020998.3 |
| HYOU1 | Hypoxia up-regulated protein 1 precursor | HYOU1_HUMAN | Q9Y4L1 | NP_001124463.1<br>NP_006380.1<br>NM_001130991.1<br>NM_006389.3 |
| IGFBP3 | Insulin-like growth factor-binding protein 3 precursor | IBP3_HUMAN | P17936 | NP_000589.2<br>NP_001013416.1<br>NM_000598.4<br>NM_001013398.1 |
| IGFBP6 | Insulin-like growth factor-binding protein 6 precursor | IBP6_HUMAN | P24592 | NP_002169.1<br>NM_002178.2 |
| IGF2 | Insulin-like growth factor II precursor | IGF2_HUMAN | P01344 | NP_000603.1<br>NP_001007140.2<br>NM_000612.4<br>NM_001007139.4 |
| CKM | Creatine kinase M-type | KCRM_HUMAN | P06732 | NP_001815.2<br>NM_001824.4 |
| LCAT | Phosphatidylcholine-sterol acyltransferase precursor | LCAT_HUMAN | P04180 | NP_000220.1<br>NM_000229.1 |
| LGALS3BP | Galectin-3-binding protein precursor | LG3BP_HUMAN | Q08380 | NP_005558.1<br>NM_005567.3 |
| LUM | Lumican precursor | LUM_HUMAN | P51884 | NP_002336.1<br>NM_002345.3 |
| SELL | L-selectin precursor | LYAM1_HUMAN | P14151 | NP_000646.2<br>NM_000655.4 |
| MAN1A1 | Mannosyl-oligosaccharide 1,2-alpha-mannosidase IA | MA1A1_HUMAN | P33908 | NP_005898.2<br>NM_005907.3 |
| MASP1 | Mannan-binding lectin serine protease 1 precursor | MASP1_HUMAN | P48740 | NP_001027019.1<br>NP_001870.3<br>NP_624302.1<br>NM_001031849.2<br>NM_001879.5<br>NM_139125.3 |
| MASP2 | Mannan-binding lectin serine protease 2 precursor | MASP2_HUMAN | O00187 | NP_006601.2<br>NP_631947.1<br>NM_006610.3<br>NM_139208.2 |
| MINPP1 | Multiple inositol polyphosphate phosphatase 1 precursor | MINP1_HUMAN | Q9UNW1 | NP_001171588.1<br>NP_001171589.1<br>NP_004888.2<br>NM_001178117.1<br>NM_001178118.1<br>NM_004897.4 |
| NCAM1 | Neural cell adhesion molecule 1 precursor | NCAM1_HUMAN | P13591 | NP_000606.3<br>NP_001070150.1<br>NP_001229537.1<br>NP_851996.2<br>NM_000615.6<br>NM_001076682.3<br>NM_001242608.1<br>NM_181351.4 |
| NID1 | Nidogen-1 precursor | NID1_HUMAN | P14543 | NP_002499.2<br>NM_002508.2 |
| PCSK9 | Proprotein convertase subtilisin/kexin type 9 precursor | PCSK9_HUMAN | Q8NBP7 | NP_777596.2<br>NM_174936.3 |

TABLE 1-continued

Markers of the Invention.

| Marker Name | Protein Description | UNIPROT_ID | UNIPROT ACCESSION | GENBANK ACCESSION |
|---|---|---|---|---|
| PDLIM1 | PDZ and LIM domain protein 1 | PDLI1_HUMAN | O00151 | NP_066272.1<br>NM_020992.3 |
| PEPD | Xaa-Pro dipeptidase | PEPD_HUMAN | P12955 | NP_000276.2<br>NP_001159528.1<br>NP_001159529.1<br>NM_000285.3<br>NM_001166056.1<br>NM_001166057.1 |
| PGLYRP2 | N-acetylmuramoyl-L-alanine amidase precursor | PGRP2_HUMAN | Q96PD5 | NP_443122.3<br>NM_052890.3 |
| GPLD1 | Phosphatidylinositol-glycan-specific phospholipase D precursor | PHLD_HUMAN | P80108 | NP_001494.2<br>NM_001503.3 |
| LCP1 | Plastin-2 | PLSL_HUMAN | P13796 | NP_002289.2<br>NM_002298.4 |
| PON1 | Serum paraoxonase/arylesterase 1 | PON1_HUMAN | P27169 | NP_000437.3<br>NM_000446.5 |
| PRDX2 | Peroxiredoxin-2 | PRDX2_HUMAN | P32119 | NP_005800.3<br>NP_859428.1<br>NM_005809.4<br>NM_181738.1 |
| PRG4 | Proteoglycan 4 precursor | PRG4_HUMAN | Q92954 | NP_001121180.1<br>NP_001121181.1<br>NP_001121182.1<br>NP_005798.2<br>NM_001127708.1<br>NM_001127709.1<br>NM_001127710.1<br>NM_005807.3 |
| PFN1 | Profilin-1 | PROF1_HUMAN | P07737 | NP_005013.1<br>NM_005022.3 |
| PROS1 | Vitamin K-dependent protein S precursor | PROS_HUMAN | P07225 | NP_000304.2<br>NM_000313.3 |
| PTGDS | Prostaglandin-H2 D-isomerase precursor | PTGDS_HUMAN | P41222 | NP_000945.3<br>NM_000954.5 |
| PTPRG | Receptor-type tyrosine-protein phosphatase gamma precursor | PTPRG_HUMAN | P23470 | NP_002832.3<br>NM_002841.3 |
| QSOX1 | Sulfhydryl oxidase 1 precursor | QSOX1_HUMAN | O00391 | NP_001004128.1<br>NP_002817.2<br>NM_001004128.2<br>NM_002826.4 |
| S100A8 | Protein S100-A8 | S10A8_HUMAN | P05109 | NP_002955.2<br>NM_002964.4 |
| S100A9 | Protein S100-A9 | S10A9_HUMAN | P06702 | NP_002956.1<br>NM_002965.3 |
| SEPP1 | Selenoprotein P precursor | SEPP1_HUMAN | P49908 | NP_001078955.1<br>NP_005401.3<br>NM_001085486.1<br>NM_005410.2 |
| SHBG | Sex hormone-binding globulin precursor | SHBG_HUMAN | P04278 | NP_001031.2<br>NP_001139752.1<br>NP_001139753.1<br>NM_001040.3<br>NM_001146280.1<br>NM_001146281.1 |
| SPP2 | Secreted phosphoprotein 24 precursor | SPP24_HUMAN | Q13103 | NP_008875.1<br>NM_006944.2 |
| TAGLN2 | Transgelin-2 | TAGL2_HUMAN | P37802 | NP_003555.1<br>NM_003564.1 |
| TNXB | Tenascin-X precursor | TENX_HUMAN | P22105 | NP_061978.6<br>NP_115859.2<br>NM_019105.6<br>NM_032470.3 |
| CLEC3B | Tetranectin precursor | TETN_HUMAN | P05452 | NP_003269.2<br>NM_003278.2 |
| TLN1 | Talin-1 | TLN1_HUMAN | Q9Y490 | NP_006280.3<br>NM_006289.3 |
| THBS1 | Thrombospondin-1 precursor | TSP1_HUMAN | P07996 | NP_003237.2<br>NM_003246.2 |
| VASN | Vasorin precursor | VASN_HUMAN | Q6EMK4 | NP_612449.2<br>NM_138440.2 |

TABLE 1-continued

Markers of the Invention.

| Marker Name | Protein Description | UNIPROT_ID | UNIPROT ACCESSION | GENBANK ACCESSION |
|---|---|---|---|---|
| VCAM1 | Vascular cell adhesion protein 1 precursor | VCAM1_HUMAN | P19320 | NP_001069.1<br>NP_001186763.1<br>NP_542413.1<br>NM_001078.3<br>NM_001199834.1<br>NM_080682.2 |
| VTN | Vitronectin precursor | VTNC_HUMAN | P04004 | NP_000629.3<br>NM_000638.3 |
| VWF | von Willebrand factor precursor | VWF_HUMAN | P04275 | NP_000543.2<br>NM_000552.3 |

In one embodiment, the one or more additional markers is selected from the group consisting of CLEC3B, ECM1, PON1, VTN, IGFALS, IGFBP3, CLU, VWF, SPP2, SELL, LUM, NCAM1, and TLN1.

In certain aspects of the invention, a single marker (e.g., any one of the markers listed in Table 1) may be used in the methods and compositions of the invention. In one embodiment, the one or more markers is selected from the group consisting of CLEC3B, ECM1, PON1, VTN, IGFALS, IGFBP3, CLU, VWF, SPP2, SELL, LUM, NCAM1, TLN1, PRG4, CA1, SHBG, CPN1, CPN2, QSOX1, PRDX2, APOA1, CA2, LPA, TAGLN2, GPX3, MST1, CNDP1, ATRN, PFN1, PEPD, VASN, BTD, CPB2, GPLD1, DBH, HGFAC, CDH5, LRG1, MASP1, PGLYRP2, TNXB, CD14, CKM, APOE, MAN1A1, PROS1, S100A8, S100A9, HABP2, BCHE, LCAT, PDLIM1, FCN3, ORM1, TGFBI, THBS1, GPS, CD163, VCAM1, LGALS3BP, PTGDS, APOC3, MINPP1, SEPP1, APOA4, MASP2, HYOU1, IGF2, GP1BA, CACNA2D1, CNTN1, NID1, COMP, PCSK9, LCP1 and APOC1.

In one embodiment, the marker is selected from the group consisting of CLEC3B, ECM1, PON1, VTN, IGFALS, IGFBP3, CLU, VWF, SPP2, SELL, LUM, NCAM1, and TLN1.

In some embodiments, the methods may further comprise determining the level of a marker selected from the group consisting of the markers listed in Table 1. In other embodiments, the methods may further comprise determining the level of one or more markers selected from the group consisting of CLEC3B, ECM1, PON1, VTN, IGFALS, IGFBP3, CLU, VWF, SPP2, SELL, LUM, NCAM1, TLN1, PRG4, CAL SHBG, CPN1, CPN2, QSOX1, PRDX2, APOA1, CA2, LPA, TAGLN2, GPX3, MST1, CNDP1, ATRN, PFN1, PEPD, VASN, BTD, CPB2, GPLD1, DBH, HGFAC, CDH5, LRG1, MASP1, PGLYRP2, TNXB, CD14, CKM, APOE, MAN1A1, PROS1, S100A8, S100A9, HABP2, BCHE, LCAT, PDLIM1, FCN3, ORM1, TGFBI, THBS1, GPS, CD163, VCAM1, LGALS3BP, PTGDS, APOC3, MINPP1, SEPP1, APOA4, MASP2, HYOU1, IGF2, GP1BA, CACNA2D1, CNTN1, NID1, COMP, PCSK9, LCP1 and APOC1

In other aspects of the invention, more than one marker, e.g., a plurality of markers, e.g., two, three, four, five, six, seven, eight, nine, ten, eleven, or more markers, may be used in the methods and compositions of the invention. In one embodiment, the combination of the plurality of the markers has an area under the curve (AUC) of about 0.85 to about 1.0. For example, in one embodiment, the combination of markers suitable for use in the methods and compositions of the invention include one of the combination of markers set forth in Table 2. In another embodiment, the combination of markers suitable for use in the methods and compositions of the invention include one of the combination of markers set forth in Table 3. In another embodiment, the combination of markers suitable for use in the methods and compositions of the invention include one of the combination of markers set forth in Table 4. In another embodiment, the combination of markers suitable for use in the methods and compositions of the invention include one of the combination of markers set forth in Table 5.

In one embodiment, the markers for use in the methods and compositions of the invention include CLEC3B and ECM1. In one embodiment, the markers for use in the methods and compositions of the invention include CLEC3B, ECM1 and PON1. In one embodiment, the markers for use in the methods and compositions of the invention include CLEC3B, ECM1, PON1, and IGFALS. In one embodiment, the markers for use in the methods and compositions of the invention include CLEC3B, ECM1, PON1, and IGFBP3. In one embodiment, the markers for use in the methods and compositions of the invention include CLEC3B, ECM1, PON1, and CLU. In one embodiment, the markers for use in the methods and compositions of the invention include CLEC3B, ECM1, PON1, and VWF. In one embodiment, the markers for use in the methods and compositions of the invention include CLEC3B, ECM1, PON1, and SPP2. In one embodiment, the markers for use in the methods and compositions of the invention include CLEC3B, ECM1, PON1, and SELL. In one embodiment, the markers for use in the methods and compositions of the invention include CLEC3B, ECM1, PON1, and LUM. In one embodiment, the markers for use in the methods and compositions of the invention include CLEC3B, ECM1, PON1, and NCAM1. In one embodiment, the markers for use in the methods and compositions of the invention include CLEC3B, ECM1, PON1, and TLN1. In one embodiment, the markers for use in the methods and compositions of the invention include CLEC3B, ECM1 and VTN. In one embodiment, the markers for use in the methods and compositions of the invention include CLEC3B, ECM1, VTN, and IGFALS. In one embodiment, the markers for use in the methods and compositions of the invention include CLEC3B, ECM1, VTN, and IGFBP3. In one embodiment, the markers for use in the methods and compositions of the invention include CLEC3B, ECM1, VTN, and CLU. In one embodiment, the markers for use in the methods and compositions of the invention include CLEC3B, ECM1, VTN, and VWF. In one embodiment, the markers for use in the methods and compositions of the invention include CLEC3B, ECM1, VTN, and SPP2. In one embodiment, the markers for use in the methods and compositions of the invention include CLEC3B, ECM1, VTN, and SELL. In one embodiment, the markers for use in the methods and compositions of the invention include CLEC3B, ECM1, VTN, and LUM. In one embodiment, the markers for use in the methods and compositions of the invention include CLEC3B, ECM1, VTN, and NCAM1. In one embodiment, the markers for use in the methods and compositions of the invention include CLEC3B, ECM1, VTN, and TLN1. In one embodiment, the markers for use in the methods and compositions of the invention include CLEC3B, ECM1, PON1, and VTN. In one embodiment, the markers for use in the methods and compositions of the invention include CLEC3B, ECM1, and IGFALS. In one embodiment, the markers for use in the methods and compositions of the invention include CLEC3B, ECM1, and IGFB3. In one embodiment, the markers for use in the methods and compositions of the invention include CLEC3B, ECM1, and CLU. In one embodiment, the markers for use in the methods and compositions of the invention include CLEC3B, ECM1, and VWF. In one embodiment, the markers for use in the methods and compositions of the invention include CLEC3B, ECM1, and SPP2. In one embodiment, the markers for use in the methods and compositions of the invention include CLEC3B, ECM1, and SELL. In one embodiment, the markers for use in the methods and compositions of the invention include CLEC3B, ECM1, and LUM. In one embodiment, the markers for use in the methods and compositions of the invention include CLEC3B, ECM1, and NCAM1. In one embodiment, the markers for use in the methods and compositions of the invention include CLEC3B, ECM1, and TLN1. In one embodiment, the combination of the markers has an area under the curve (AUC) of about 0.85 to about 1.0.

In some embodiments, the methods may further comprise determining the level of a marker selected from the group consisting of the markers listed in Table 1. In other embodiments, the methods may further comprise determining the level of one or more markers selected from the group consisting of CLEC3B, ECM1, PON1, VTN, IGFALS, IGFBP3, CLU, VWF, SPP2, SELL, LUM, NCAM1, TLN1, PRG4, CAL SHBG, CPN1, CPN2, QSOX1, PRDX2, APOA1, CA2, LPA, TAGLN2, GPX3, MST1, CNDP1, ATRN, PFN1, PEPD, VASN, BTD, CPB2, GPLD1, DBH, HGFAC, CDH5, LRG1, MASP1, PGLYRP2, TNXB, CD14, CKM, APOE, MAN1A1, PROS1, S100A8, S100A9, HABP2, BCHE, LCAT, PDLIM1, FCN3, ORM1, TGFBI, THBS1, GPS, CD163, VCAM1, LGALS3BP, PTGDS, APOC3, MINPP1, SEPP1, APOA4, MASP2, HYOU1, IGF2, GP1BA, CACNA2D1, CNTN1, NID1, COMP, PCSK9, LCP1 and APOC1.

III. Methods of the Invention

A. Diagnostic Methods

In certain aspects, the present invention provides diagnostic methods. For example, in one aspect, the present invention provides methods for determining whether a subject exposed to TB will develop latent tuberculosis (TB). The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates that the subject will develop latent TB.

The methods of the present invention can be practiced in conjunction with any other method(s) used by the skilled practitioner to diagnose, prognose, and/or monitor TB. For example, the methods of the invention may be performed in conjunction with any clinical measurement of TB known in the art including serological, cytological and/or detection (and quantification, if appropriate) of other molecular markers.

In any of the methods (and kits) of the invention, the level of a marker(s) of the invention in a sample obtained from a subject may be determined by any of a wide variety of well-known techniques and methods, which transform a marker of the invention within the sample into a moiety that can be detected and quantified. Non-limiting examples of such methods include analyzing the sample using immunological methods for detection of proteins, protein purification methods, protein function or activity assays, nucleic acid hybridization methods, nucleic acid reverse transcription methods, and nucleic acid amplification methods, immunoblotting, Western blotting, Northern blotting, electron microscopy, mass spectrometry, e.g., MALDI-TOF and SELDI-TOF, immunoprecipitations, immunofluorescence, immunohistochemistry, enzyme linked immunosorbent assays (ELISAs), e.g., amplified ELISA, quantitative blood based assays, e.g., serum ELISA, quantitative urine based assays, flow cytometry, Southern hybridizations, array analysis, and the like, and combinations or sub-combinations thereof.

For example, an mRNA sample may be obtained from the sample from the subject (e.g., blood, serum, bronchial lavage, mouth swab, biopsy, or peripheral blood mononuclear cells, by standard methods) and expression of mRNA(s) encoding a marker of the invention in the sample may be detected and/or determined using standard molecular biology techniques, such as PCR analysis. A preferred method of PCR analysis is reverse transcriptase-polymerase chain reaction (RT-PCR). Other suitable systems for mRNA sample analysis include microarray analysis (e.g., using Affymetrix's microarray system or Illumina's BeadArray Technology).

It will be readily understood by the ordinarily skilled artisan that essentially any technical means established in the art for detecting the level a marker of the invention at either the nucleic acid or protein level, can be used to determine the level a marker of the invention as discussed herein.

In one embodiment, the level of a marker of the invention in a sample is determined by detecting a transcribed polynucleotide, or portion thereof, e.g., mRNA, or cDNA, of a marker of the invention gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting, in situ hybridization, and microarray analysis.

In one embodiment, the level of a marker of the invention is determined using a nucleic acid probe. The term "probe", as used herein, refers to any molecule that is capable of selectively binding to a specific marker of the invention. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize to a marker mRNA. The nucleic acid probe can be, for example, a full-length cDNA, or a portion thereof, such as an oligonucleotide of at least about 7, 10, 15, 20, 25, 30, 35, 40, 45, 50, 100, 250 or about 500 nucleotides in length and sufficient to specifically hybridize under stringent conditions to marker genomic DNA.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of a marker of the invention mRNA.

An alternative method for determining the level of a marker of the invention in a sample involves the process of nucleic acid amplification and/or reverse transcriptase (to prepare cDNA) of for example mRNA in the sample, e.g., by RT-PCR (the experimental embodiment set forth in Mullis 1987, U.S. Pat. No. 4,683,202), ligase chain reaction (Barany (1991) *Proc. Natl. Acad. Sci. USA* 88:189-193), self-sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of a marker of the invention is determined by quantitative fluorogenic RT-PCR (i.e., the TaqMan™ System). Such methods typically utilize pairs of oligonucleotide primers that are specific for a marker of the invention. Methods for designing oligonucleotide primers specific for a known sequence are well known in the art.

The level of a marker of the invention mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of a level of a marker of the invention may also comprise using nucleic acid probes in solution.

In one embodiment of the invention, microarrays are used to detect the level of a marker of the invention. Microarrays are particularly well suited for this purpose because of the reproducibility between different experiments. DNA microarrays provide one method for the simultaneous measurement of the levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, e.g., U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

In certain situations it may be possible to assay for the level of a marker of the invention at the protein level, using a detection reagent that detects the protein product encoded by the mRNA of a marker of the invention. For example, if an antibody reagent is available that binds specifically to a marker of the invention protein product to be detected, and not to other proteins, then such an antibody reagent can be used to detect the expression of a marker of the invention in a cellular sample from the subject, or a preparation derived from the cellular sample, using standard antibody-based techniques known in the art, such as FACS analysis, and the like.

Other known methods for detecting a marker of the invention at the protein level include methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, and Western blotting.

Proteins from samples can be isolated using techniques that are well known to those of skill in the art. The protein isolation methods employed can, for example, be those described in Harlow and Lane (Harlow and Lane, 1988, Antibodies: A Laboratory Manual, Cold Spring Harbor Laboratory Press, Cold Spring Harbor, N.Y.).

In one embodiment, antibodies, or antibody fragments, are used in methods such as Western blots or immunofluorescence techniques to detect the expressed proteins. Antibodies for determining the expression of a marker of the invention are commercially available and one of ordinary skill in the art can readily identify appropriate antibodies for use in the methods of the invention.

It is generally preferable to immobilize either the antibody or proteins on a solid support for Western blots and immunofluorescence techniques. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means. Means of detecting proteins using electrophoretic techniques are well known to those of skill in the art (see generally, R. Scopes (1982) Protein Purification, Springer-Verlag, N.Y.;

Deutscher, (1990) *Methods in Enzymology* Vol. 182: *Guide to Protein Purification*, Academic Press, Inc., N.Y.).

Other standard methods include immunoassay techniques which are well known to one of ordinary skill in the art and may be found in Principles And Practice Of Immunoassay, 2nd Edition, Price and Newman, eds., MacMillan (1997) and Antibodies, A Laboratory Manual, Harlow and Lane, eds., Cold Spring Harbor Laboratory, Ch. 9 (1988), each of which is incorporated herein by reference in its entirety.

Antibodies used in immunoassays to determine the level of a marker of the invention, may be labeled with a detectable label. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In one embodiment, the antibody is labeled, e.g. a radiolabeled, chromophore-labeled, fluorophore-labeled, or enzyme-labeled antibody. In another embodiment, an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a marker of the invention.

In one embodiment of the invention, proteomic methods, e.g., mass spectrometry, are used to determine the level of a marker of the invention. Mass spectrometry is an analytical technique that consists of ionizing chemical compounds to generate charged molecules (or fragments thereof) and measuring their mass-to-charge ratios. In a typical mass spectrometry procedure, a sample is obtained from a subject, loaded onto the mass spectrometry, and its components (e.g., a marker of the invention) are ionized by different methods (e.g., by impacting them with an electron beam), resulting in the formation of charged particles (ions). The mass-to-charge ratio of the particles is then calculated from the motion of the ions as they transit through electromagnetic fields.

For example, matrix-associated laser desorption/ionization time-of-flight mass spectrometry (MALDI-TOF MS) or surface-enhanced laser desorption/ionization time-of-flight mass spectrometry (SELDI-TOF MS) which involves the application of a biological sample, such as serum, to a protein-binding chip (Wright, G. L., Jr., et al. (2002) *Expert Rev Mol Diagn* 2:549; Li, J., et al. (2002) *Clin Chem* 48:1296; Laronga, C., et al. (2003) *Dis Markers* 19:229; Petricoin, E. F., et al. (2002) 359:572; Adam, B. L., et al. (2002) *Cancer Res* 62:3609; Tolson, J., et al. (2004) *Lab Invest* 84:845; Xiao, Z., et al. (2001) *Cancer Res* 61:6029) can be used to determine the level of a marker of the invention.

Furthermore, in vivo techniques for determination of the level of a marker of the invention include introducing into a subject a labeled antibody directed against a marker of the invention, which binds to and transforms a marker of the invention into a detectable molecule. As discussed above, the presence, level, or even location of the detectable marker of the invention in a subject may be detected determined by standard imaging techniques.

In general, it is preferable that the difference between the level of a marker of the invention in a sample from a subject and the amount of a marker of the invention in a control sample, is as great as possible. Although this difference can be as small as the limit of detection of the method for determining the level of a marker it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the standard error of the assessment method.

B. Methods for Monitoring the Effectiveness of a Treatment

The present invention also provides methods for monitoring the effectiveness of a therapy or treatment regimen or any other therapeutic approach useful for treating a subject having latent TB and/or inhibiting the progression of TB to disseminated TB (or a complication associated with disseminated TB (e.g., spinal and kidney meningitis, peritonitis, pericarditis, bone and joint complications, fallopian tube infection, bowel infection, Adult respiratory distress syndrome (ARDS), liver inflammation, lung failure, and/or relapse of the disease) in a subject having TB.

In these methods the level of one or more markers of the invention in a pair of samples (a first sample not subjected to the treatment regimen and a second sample subjected to at least a portion of the treatment regimen) is assessed. A modulation in the level of expression of the one or more markers in the first sample, relative to the second sample, is an indication that the therapy is effective for treating a subject having latent TB and/or inhibiting the progression of TB to disseminated TB (or a complication associated with disseminated TB (e.g., spinal and kidney meningitis, peritonitis, pericarditis, bone and joint complications, fallopian tube infection, bowel infection, Adult respiratory distress syndrome (ARDS), liver inflammation, lung failure, and/or relapse of the disease) in a subject having TB.

C. Treatment Methods

The present invention also provides methods for treating a subject having latent TB and methods for reducing or inhibiting the development of complications associated with the disease in a subject The methods of "inhibiting", "slowing", and/or "treating" include administration of a therapeutic agent to a subject in order to cure or to prolong the health or survival of a subject beyond that expected in the absence of such treatment.

The terms "patient" or "subject" as used herein is intended to include human and veterinary patients. In a particular embodiment, the subject is a human The term "non-human animal" includes all vertebrates, e.g., mammals and non-mammals, such as non-human primates, mice, rabbits, sheep, dog, cow, chickens, amphibians, and reptiles.

The methods of the invention include administering to the subject one or more "standard" therapies. For example, the therapeutic agents include cytotoxins, immunosuppressive agents, radiotoxic agents, and/or therapeutic antibodies. Particular co-therapeutics contemplated by the present invention include, but are not limited to, Isoniazid, Rifampin (Rifadin, Rimactane), Ethambutol (Myambutol), Pyrazinamide, streptomycin, vitamin D, Clarithromycin, Dapsone, Ofloxacin, Rifabutin, Non-nucleoside reverse transcriptase inhibitors (NNRTIs; e.g., efavirenz (Sustiva), etravirine (Intelence) and nevirapine (Viramune, Nucleoside reverse transcriptase inhibitors (NRTIs; e.g., Abacavir (Ziagen), and the combination drugs emtricitabine and tenofovir (Truvada), and lamivudine and zidovudine (Combivir), Protease inhibitors (PIs; e.g., atazanavir (Reyataz), darunavir (Prezista), fosamprenavir (Lexiva) and ritonavir (Norvir), Entry or fusion inhibitors, e.g., enfuvirtide (Fuzeon) and maraviroc (Selzentry), and Integrase inhibitors, e.g., Raltegravir (Isentress), or combinations thereof.

The methods of the invention also contemplate the use of therapeutic agents in combination with other therapies, including life-style changes.

In some embodiments, two or more therapeutic agents are applied to a subject. Two or more therapeutic agents can be administered in the same formulation or separately. In the case of separate administration, the therapeutic agents can be administered before, after or concurrently with the co-therapeutic or co-therapy. One agent may precede or follow administration of the other agent by intervals ranging from minutes to weeks. In embodiments where two or more different kinds of therapeutic agents are applied separately to a subject, one would generally ensure that a significant period of time did not expire between the time of each delivery, such that these different kinds of agents would still be able to exert an advantageously combined effect on the target tissues or cells.

The term "effective amount" as used herein, refers to that amount of therapeutic agent(s) which is sufficient to treat and/or inhibit the progression of latent TB and/or a complication of TB in a subject when administered to a subject. An effective amount will vary depending upon the subject and the severity of the disease and age of the subject, the manner of administration and the like, which can readily be determined by one of ordinary skill in the art. Dosage regimens may be adjusted to provide the optimum therapeutic response. An effective amount is also one in which any toxic or detrimental effects (i.e., side effects) of a therapeutic agent(s) are minimized and/or outweighed by the beneficial effects.

IV. Kits of the Invention

The invention also provides kits for determining whether a subject exposed to TB will develop latent TB. Kits for monitoring the effectiveness of a treatment for latent TB are also provided.

These kits include means for determining the level of one or more markers of the invention and instructions for use of the kit.

The kits of the invention may optionally comprise additional components useful for performing the methods of the invention. By way of example, the kits may comprise reagents for obtaining a biological sample from a subject, a control sample, one or more sample compartments, a diabetic therapeutic, an instructional material which describes performance of a method of the invention and tissue specific controls/standards.

The reagents for determining the level of one or more marker(s) can include, for example, buffers or other reagents for use in an assay for evaluating the level of one or more markers, e.g., expression level (e.g., at either the mRNA or protein level). The instructions can be, for example, printed instructions for performing the assay for evaluating the level of one or more marker(s) of the invention.

The reagents for isolating a biological sample from a subject can comprise one or more reagents that can be used to obtain a fluid or tissue from a subject, such as means for obtaining a saliva or blood.

The kits of the invention may further comprise reagents for culturing a sample obtained from a subject.

Preferably, the kits are designed for use with a human subject.

The present invention is further illustrated by the following examples which should not be construed as further limiting. The contents of all references, patents and published patent applications cited throughout this application, as well as the Figures, are expressly incorporated herein by reference in their entirety.

EXAMPLES

Example I. Biomarker Identification

Introduction

Approximately one-third of the world's population is latently infected with *Mycobacterium tuberculosis*, meaning they do not have symptoms, chest radiographic abnormalities, or other findings of active tuberculosis (TB). People with latent Mtb infection (LTBI) are the primary source of future TB cases, and their identification is important for TB control. Diagnosis of LTBI is based on immunological activity suggesting current or previous infection, commonly measured by either the tuberculin skin test (TST) or interferon gamma release assay (IGRA). Neither test is able to differentiate between LTBI and active TB, nor distinguish recent from remote infection. This is an important distinction since recent infection is a strong risk factor for progression to active TB, and in some high incidence areas, the majority of TB cases are likely due to recent infections from ongoing TB transmission (Chin et al., 1998, *Am J Respir Crit Care Med*, 158, 1797-803, Verver et al., 2004 *Int J Epidemiol*, 33, 351-7). Developing a diagnostic assay that identifies recent Mtb infection (LTBI) would allow for targeted treatment of those persons most likely to progress to active TB and is a priority among international TB agencies (Pai and Schito, 2015 *J Infect Dis*, 211 Suppl 2, S21-8).

Mass spectrometry (MS) coupled with multiple reaction monitoring (MRM-MS) allows for rapid detection and quantification of proteins with high sensitivity and precision (Hunter and Paramithiotis, 2010 *Expert Opin Med Diagn*, 4, 11-20). Previous studies have used MRM-MS proteomic assays to identify new biomarkers of LTBI by detecting both Mtb (Kruh-Garcia et al., 2014 *PLoS One*, 9, e103811) and human host proteins in peripheral blood (Sandhu et al., 2012, *PLoS One*, 7, e38080, Zhang et al., 2014 *Diagn Microbiol Infect Dis*, 79, 432-7). In these previous cross-sectional studies, LTBI was diagnosed by TST or IGRA, but it was not known when the subject was infected with Mtb (recent vs remote infection). In this study, blood samples from a prospective TB household contact cohort were analyzed using MRM-MS to assess the host-protein proteomic profiles in blood from household contacts who converted from TST-negative to TST-positive. Changes in circulating host-proteins as a person develops LTBI are reported.

Materials and Methods

Study Design and Subjects

The studies described below was designed to identify protein biomarkers associated with early stage TB infection. The studies entailed two parts, a discovery and a verification phase. For both parts, independent serum and plasma samples were collected and evaluated from a household exposure study in Kampala, Uganda. Patients in this study were enrolled in the Kawempe Community Health Study (KCHS), a prospective cohort of adult pulmonary TB index cases and their household contacts, conducted in Kampala, Uganda. Individuals diagnosed with TB and their household members were recruited and followed for a period of 2 years. In this study, index cases were adults (age 18 and older) with initial episodes of newly diagnosed culture-positive pulmonary TB. Household contacts included persons (age 12 years and older) living in the same building as an index case for at least one week during the three-month period immediately preceding the index case diagnosis. After the initial evaluation, participants were evaluated at 3, 6, 12, and 24 months for active TB and with repeat TST if their first and subsequent TST remained negative. All individuals were monitored clinically and if signs and symptoms of TB developed, evaluated as TB suspects. Tuberculin skin testing was done using 5 TU of purified protein derivative (PPD). All subjects were HIV−. A subset of the household members developed TB infection, and a portion of these progressed to active TB. The study was approved by the responsible institutional review boards in Uganda and the U.S. Converters were defined as household contacts, with an initial TST≤10 mm at baseline visit, who subsequently converted their skin test to positive (TST≥10 mm and an increment of 6 mm) during follow-up testing. Subjects that remained TST-negative and did not convert their TST were considered to be persistently not infected (NI) (Ma et al., 2014 *BMC Infect Dis*, 14, 352). All subjects with a positive TST (at baseline or conversion during follow-up) were offered treatment with isoniazid preventive therapy (IPT) (10-20 mg/kg or a maximum dose of 300 mg/day) for 9 months.

TB cases were compared to various controls groups in a case-control design. In the discovery phase, cross-sectional comparisons of biomarker expression were made between individuals that were either non-infected for the period of the study (NI), or had been exposed and will convert to latent infection 3 months after the sample was collected (CO), or had a latent infection at the time of sample collection (LTBI), or had an active infection (ATB) at the time of sample collection. The clinical data of the subjects for the discovery phase is provided in FIG. 1.

In the verification phase, two sets of independent cross-sectional and longitudinal samples from the same household exposure study were used to confirm performance of candidate biomarkers identified in the discovery phase in predicting the establishment of latent TB infection. The clinical data of the subjects for the verification phases is also provided in the FIG. 1.

Sample Processing.

To avoid introducing bias in the sample preparation, the samples were grouped into blocks containing one of each of the groups (if possible). The order of the groups within each block was then randomized.

For the discovery samples, all sera samples were depleted of abundant proteins using affinity chromatography ((an antibody column (IgY14 and Supermix, Sigma)). The remaining lower abundance proteins were digested with trypsin (Promega) prior to analysis by LC-MS. Plasma from the longitudinal verification phase was also depleted of abundant proteins using affinity chromatography and trypsin digestion prior to LC-MS analysis. Following freeze-drying of the digested samples, they were resolubilized and treated with TCEP (tris(2-carboxyethyl)phosphine) to reduce disulfide bonds. The samples were then desalted by solid phase extraction using a 3M Empore C18 desalting plate and distributed into 96-well plates and vacuum evaporated. Peptides were stored at −20° C. until use.

Tandem Mass Spectrometry Analysis

Freeze dried peptides were resuspended in 92.5/7.5 water/acn+0.2% formic acid and analyzed using a nanoAcquity pump (Waters) coupled to a Q-TOF mass spectrometer (Waters). Peptide separation was achieved using a Waters nanoAcquity Symmetry UPLC Trap column (180 μm×20 mm, 5 μm particle size) and a Waters nanoAcquity UPLC BEH300 analytical column (150 μm×100 mm, 1.7 μm particle size). Each sample was loaded on the trapping column for 3 min at a flow rate of 10 μL/min, and then the gradient was started at a flow rate at 1.8 μL/min. The total run time per sample was 105 min Components were detected and matched across all samples using the Elucidator software (Rosetta Biosoftware) and compared for relative peak intensity. All intensity values were log (base e) transformed with values<0 replaced by 0. Peak intensity was normalized to account for small differences in protein concentration between samples: a subset of the samples was used to create an average sample (i.e. the Reference sample) against which all samples were then normalized. The normalization factors were chosen so that the median of log ratios between each sample and the Reference sample over all the peptides was adjusted to zero. For batch-effect correction, a one-way ANOVA model $I_{ij}=M+D_i+\varepsilon_{ij}$ (I: intensity, M: overall interception, and D: batch-factor) was solved and parameters $D_i$ (i=1,2) under the constraint of $\Sigma_{i=1}^{2}(N_i*D_i)=0$ were obtained; the $D_i$'s were then subtracted from the normalized intensities to form the "batch-effect corrected" intensities. Intensities below the limit of detection (LOD=30) were transformed to avoid spurious large fold changes: intensities in the range of (0, LOD) were linearly mapped to the range of (LOD/2, LOD). A one-way ANOVA analysis was then applied to identify peptides that were differentially expressed between the groups of interest. High stringency thresholds were used to ensure the statistical significance of the identified peptides. Each group was analyzed using the same one-way ANOVA model [=(Montgomery, D. C., *Design and Analysis of Experiments*, Wiley, 2001; Keeping, E. S., *Introduction to Statistical Inference*, Dover Publication, Inc. 1995): $I_{ij}=M+C_i+\varepsilon_{ij}$ where I is the peptide intensity, M is the overall average intensity, C is the 'clinical group' factor, and ε is random error. FDR (false detection rate) and q-value were calculated, based on the p-values obtained from the ANOVA, using Storey's method (Storey, J. D. (2002) *Journal of the Royal Statistical Society* 64(3):479-498) to make multiple testing adjustments (implemented in MATLAB) (mathworks.com/access/helpdesk/help/helpdesk.html; MATLAB for Math Works Inc.). 'Post hoc' contrast analyses were conducted using Tukey's hsd (Hochberg, Y., and A. C. Tamhane. *Multiple Comparison Procedures*. John Wiley & Sons, 1987) method to calculate p-values associated with each pair wise comparison. Protein identification was done by analysis of replicate samples by tandem mass spectrometry (LC-MS/MS). A protein level analysis was then applied using an extension of the one-way ANOVA used above in the peptide level analysis, which takes into consideration that one protein may have several peptides, by introducing a 'peptide factor' in the model: $I_{ijk}=M+C_i+P_j+\varepsilon_{ijk}$ where I is the protein intensity, M an overall constant, C the 'clinical group', and P the peptide factor. The number of the levels for P is protein-dependent, equal to the number of children peptides for the protein. These calculations were implemented in MATLAB (mathworks.com/access/helpdesk/help/helpdesk.html; MATLAB for Math Works Inc.). Proteins were considered to be differentially expressed if they met the following thresholds: p- and q-values<0.05, and Differential Intensity (DI) superior at 1.1-fold change Multiple Reaction Monitoring Mass Spectrometry A multiplex MRM assay was developed for the selected biomarker candidates. The assay contained 392 peptides representing 162 host proteins. Peptides were synthesized by JPT Peptide Technologies (Berlin, Germany) The synthesized peptides were resolubilized in 72/25 water/DMSO, pooled and diluted with water+0.2% formic acid to a final concentration of 2 nmol/mL. Five μL of this solution was analyzed on a QTRAP 5500 mass spectrometer (ABSciex, Canada) using a 320 μm×150 mm, 5 μm particle size, Thermo Biobasic C18 column. A linear gradient of 10-40% acetonitrile (0.2% formic acid) in 30 minutes was used for peptide separation. MS/MS spectra of the synthetic peptides were acquired using selected reaction monitoring (SRM)-triggered MS/MS allowing the identification of peptide and peptide fragments (transitions). The two most intense fragment ions (b or y fragment ions only) in the MS/MS spectrum and its elution time were determined for each acquired peptide. The collision energy (CE) was then optimized for each of the chosen transitions. The CE values evaluated were the empirical calculated CE value and the empirical CE value −6, +3 and +6. Independent plasma samples from those used for the discovery study by tandem mass spectrometry were processed as described and the resulting peptides were analyzed by the MRM assay.

Expression analysis of MRM data was performed using R version 2.14.0, platform x86_64-pc-mingw32/x64 (64-bit). The calculation of q-values was done using function "qvalue" from Storey's package "qvalue" version 1.24.0. A limit of quantification (LOQ), defined as an intensity value below which the measure is deemed unreliable, was determined empirically according to the QTRAP 5500 and was set to 10000, pre-normalization. The detection rate (DR), defined for each group that needed to be compared, was defined as the proportion of samples with a raw intensity (i.e. pre normalization) value greater or equal to the LOQ. Transitions for which the DR was below 50% for one of the two groups were excluded from expression analysis. Prior to expression analysis, an outlier and pattern detection analysis was performed. The distribution of sample detection was investigated and a sample was rejected from analysis because of a poor detection rate. The sample intensity average distribution by depletion day was also investigated and three samples were rejected for being too weak. A standard Principal Component Analysis (PCA) was applied to the ln intensities in order to visually assess any pattern in the data that are likely to be unrelated to sample condition. Differential intensity ratios (DI) were then calculated for each transition, for two-group comparisons (e.g., Active TB vs Latent TB), as the ratio of the median normalized intensities of each group. Prior to calculating the differential intensity ratios, all intensity values that were below the LOQ quantity in the raw data prior to normalization were replaced by the half-LOQ value. Student's t-test were applied for the expression analysis Protein-level statistics were also computed by first linearly combining the transitions of a given protein into a single variable and then applying a t-test on it.

Panel Definition

Area Under the Curve (AUC) values were computed from bootstrap. Select n samples with replacement (i.e. take a sample at random, then a second—with the first selected sample being possibly selected again, and so on). By design, some samples were left out, called out-of-bag. The selected samples (some more than once) are called the bootstrap samples. Build panel on the bootstrap samples and evaluate on the out-of-bag sample by calculating AUC. This was done 100 times. Reported AUC is the average of the 100 AUC. Each protein was represented by a single transition. Transitions with a DR lower than 80% were filtered-out. Among the remaining transitions, proteins for which the transitions were not trending the same way, based on DI, were filtered-out. The selected transition of a protein was the one with the highest DR. In situation of ties, this transition was selected randomly. Logistic Regression models were built with the proteins (i.e. represented by its selected transition) as explanatory variables. All combinations of proteins from 1 to 4 were systematically fitted into such logistic models. Proteins were then ranked by their propensity to be a good team player. For k from 1 to 4, combinations were ranked by their AUC and for each protein, the mean rank of the combinations they appear in, for a given k, was calculated. Within each k, the protein rank was calculated as the rank of the average rank. The final rank was taken as the weighted average over k of the ranks. The highest ranking of the 4 protein panels were then used as the base for extending panel size to 8 proteins, and the larger panels were evaluated in the same manner as decribed.

Results

Peripheral blood specimens previously collected from 172 TB patients and household contacts were used for this study. The clinical characteristics of the subjects are shown in Table 1. The discovery phase was conducted by a cross-sectional analysis of proteomic expressions among baseline samples from 37 index cases with active TB, 8 TST-negative contacts who remained TST-negative and non-infected (NI), 21 TST-negative contacts who later converted their TST at either 3 or 6 months (converters), and 38 TST-positive contacts with LTBI at baseline.

Peptide expression data acquired were log-transformed and normalized for injection order and depletion day. ANOVA analysis was then applied to identify differentially expressed peptides. The average peptide intensity was used to create an intensity value per protein which was z-scored and differential intensity ratios (DI) were calculated.

Two hundred eight-nine proteins were identified to be significantly differentially expressed in any of these comparisons using mass spectrometry (LC-MS)(($p<0.05$)). FIGS. 2A-2D show cross-sectional comparisons of changes in blood protein expression ratios from the baseline samples. The significant changes in Differntial Intensity (DI) ($p<0.05$) are shaded in gray as described above. If the DI value is above 1 the level of the protein is upregulated. If the DI value is less than 1, the level of the marker is downregulated.

It was found that when compared to the NI group, the number of differentially expressed proteins increased by the following group order: converters, LTBI, and active TB. The largest absolute differences in protein expression were observed between NI participants and patients with active TB. It was also found differences in protein expression when looking at changes grouped by biological processes. Most protein changes associated with inflammation, immune response, tissue repair, cellular migration and proliferation were observed in subjects with active TB. Among the LTBI and converter groups, smaller changes were observed in these processes, as well as changes in proteins associated with lipid metabolism and the innate immune response (FIGS. 2A-2D). The results are consistent with a low level of distinct observable changes in Mtb infection, including very recent infection, exhibited by the baseline TST-negative future converters who were in the process of developing LTBI.

A targeted MRM-MS assay was developed for 159 proteins selected from each comparison in the cross-sectional discovery phase using the following combination of biological and statistical criteria. All of the significantly differentially expressed proteins from the baseline converter vs NI and LTBI vs NI comparisons were selected along with the most differentially expressed proteins from comparisons to active TB. Also included were the significant proteins identified previously in an active TB biomarker study, as provided in U.S. Patent Publication No. 2016/0154005 (incorporated herein in its entirety by reference) and Achkar, et al. (2015 *EBioMedicine*, 2, 1160-8)). Re-analysis of the discovery samples with the MRM-MS assay confirmed the differential expression observed in the discovery phase. Next, an independent set of 161 longitudinal samples collected from 52 subjects who were initially all TST-negative and either converted to TST-positive (N=37) or remained TST-negative (N=15) were tested with the prioritized candidate biomarkers. The changes in plasma proteins at baseline and at a minimum of 2 additional time points over a 6 month period were calculated.

FIGS. 3A and 3B show protein expression change ratios between each individual's baseline TST-negative sample and the longitudinal TST-positive conversion sample or corresponding TST-negative sample. The significant changes (p<0.05) are shded in gray as described above. As expected, subjects who became TST-positive had a more extensive host response than the subjects that remained TST-negative.

In an analysis of subjects that converted by 3 months, most of the proteins associated with inflammatory, innate and adaptive immune responses were elevated at month 3, when TST conversion was recorded, but returned to baseline levels by month 6. In contrast, most of the proteins associated with cellular movement and tissue repair remained elevated through month 6 (FIGS. 4A and 4B). Converters were treated with isoniazid preventive therapy for 9 months after TST conversion, and this may have had an effect on protein expression measured at month 6.

This data was used to define combinations of up to 4 candidate biomarker proteins able to distinguish latent TB from the other clinical groups. 131 proteins from the MRM assay were detected in this second study. A subset of 76 proteins were used to derive panel combinations in order to identify proteins that predict the establishment of latent TB infection (see Tables 2-5).

In verification phase 2, the panel combinations of the 76 proteins were evaluated further using another set of longitudinal samples, collected from subjects from the same household exposure study who had not participated in prior phases of the project. A total of 43 longitudinal samples from 16 subjects were used in this sample set. As demonstrated in Tables 3-5, the data demonstrate that small panel combinations of 13 proteins (CLEC3B, ECM1, PON1, VTN, IGFALS, IGFBP3, CLU, VWF, SPP2, SELL, LUM, NCAM1, and TLN1) predict the establishment of latent infection consistently. Combining the biomarker candidates into panels was a more effective strategy to derive high performing discriminators (see Tables 3-5). A small number of combinations of the biomarkers identified in this study were found to be predictive of latent and active TB infection (Table 7).

Biomarkers predictive of active TB infection (as provided in U.S. Patent Publication No. 2016/0154005 (incorporated herein in its entirety by reference) were evaluated for their ability to predict latent TB infection as well. As provided in Table 6, combinations of two or three of the previously identified active TB biomarkers showed significantly lower AUC values than high performing panel combinations of latent TB biomarkers (see Tables 3-5).

The performance of the candidate biomarkers for latent TB is presented in Tables 8-9 which provide the Differential Intensity (DI) value for each marker comparison. If the DI value is above 1, the level of the protein is upregulated for that particular comparison. If the DI value is less than 1, the level of the marker is downregulated for that particular comparison. Table 8 provides a cross-sectional comparison of DI values for 13 markers in sera from non-infected (NI), TST+ converter (CO), latent TB (LTBI) and active TB groups. Table 9 provides a longitudinal comparison of DI values for 13 markers in plasma from TST-subjects that converted to TST+ during the sampling time course, or TST- subjects that remained TST- during the sampling time course.

These results demonstrate that small panels of biomarkers are able to predict 3-6 months ahead of time the conversion from a TST-negative to a TST-positive state and thus predict the establishment of LTBI.

TABLE 2

Panel Combinations of Two Candidate Latent TB Biomarkers

| protein.1 | protein.2 | AUC |
| --- | --- | --- |
| COMP | ECM1 | 0.85 |
| CKM | ECM1 | 0.84 |
| CLEC3B | ECM1 | 0.83 |
| ECM1 | THBS1 | 0.82 |
| PDLIM1 | PON1 | 0.82 |
| ECM1 | PDLIM1 | 0.81 |
| PON1 | THBS1 | 0.81 |
| ECM1 | NA | 0.81 |
| SELL | THBS1 | 0.81 |
| ECM1 | PON1 | 0.81 |
| ECM1 | QSOX1 | 0.81 |
| ECM1 | MST1 | 0.81 |
| PON1 | VWF | 0.80 |
| ECM1 | TGFBI | 0.80 |
| CNDP1 | ECM1 | 0.80 |
| ECM1 | NCAM1 | 0.80 |
| CLU | ECM1 | 0.80 |
| ECM1 | PRDX2 | 0.80 |
| ECM1 | ORM1 | 0.80 |
| ECM1 | PEPD | 0.80 |
| ECM1 | MASP2 | 0.80 |
| ECM1 | SEPP1 | 0.80 |
| BCHE | ECM1 | 0.80 |
| ECM1 | MAN1A1 | 0.80 |
| ECM1 | GP5 | 0.80 |
| APOE | ECM1 | 0.80 |
| APOC1 | ECM1 | 0.80 |
| CA1 | ECM1 | 0.80 |
| ECM1 | LCAT | 0.80 |
| CPN1 | ECM1 | 0.79 |
| ECM1 | VWF | 0.79 |
| ECM1 | MINPP1 | 0.79 |
| ECM1 | SPP2 | 0.79 |
| ECM1 | GPX3 | 0.79 |
| ECM1 | GPLD1 | 0.79 |
| ECM1 | LPA | 0.79 |
| PDLIM1 | TAGLN2 | 0.79 |
| HABP2 | THBS1 | 0.79 |
| BTD | ECM1 | 0.79 |
| IGFALS | THBS1 | 0.79 |
| ECM1 | LGALS3BP | 0.79 |
| ECM1 | VCAM1 | 0.79 |
| CA2 | ECM1 | 0.79 |
| ECM1 | IGF2 | 0.79 |
| ECM1 | GP1BA | 0.79 |
| ECM1 | MASP1 | 0.79 |
| ECM1 | TNXB | 0.79 |
| ECM1 | IGFBP3 | 0.79 |
| ECM1 | HABP2 | 0.79 |
| CPB2 | ECM1 | 0.79 |
| ECM1 | IGFALS | 0.79 |

TABLE 2-continued

Panel Combinations of Two Candidate Latent TB Biomarkers

| protein.1 | protein.2 | AUC |
|---|---|---|
| ECM1 | PGLYRP2 | 0.79 |
| ECM1 | SELL | 0.79 |
| ECM1 | LCP1 | 0.79 |
| APOA4 | ECM1 | 0.79 |
| ECM1 | HGFAC | 0.79 |
| ECM1 | PFN1 | 0.79 |
| ECM1 | VTN | 0.79 |
| ECM1 | LRG1 | 0.79 |
| ECM1 | LUM | 0.79 |
| LCP1 | THBS1 | 0.79 |
| CD163 | ECM1 | 0.79 |
| APOA1 | ECM1 | 0.79 |
| APOC3 | ECM1 | 0.79 |
| PDLIM1 | SELL | 0.79 |
| ECM1 | VASN | 0.79 |
| ECM1 | FCN3 | 0.79 |
| ECM1 | SHBG | 0.79 |
| ECM1 | NID1 | 0.79 |
| ATRN | ECM1 | 0.78 |
| ECM1 | PRG4 | 0.78 |
| ECM1 | PTGDS | 0.78 |
| ECM1 | PROS1 | 0.78 |
| CD14 | ECM1 | 0.78 |
| ECM1 | S100A8 | 0.78 |
| ECM1 | TAGLN2 | 0.78 |
| CDH5 | ECM1 | 0.78 |
| CD14 | PON1 | 0.78 |
| LCP1 | PON1 | 0.78 |
| IGFBP3 | THBS1 | 0.78 |
| DBH | ECM1 | 0.78 |
| ECM1 | HYOU1 | 0.78 |
| ECM1 | S100A9 | 0.78 |
| ECM1 | TLN1 | 0.78 |
| PON1 | TLN1 | 0.78 |
| ECM1 | PCSK9 | 0.78 |
| PON1 | PRDX2 | 0.78 |
| CPN2 | ECM1 | 0.78 |
| APOC1 | PON1 | 0.78 |
| BTD | THBS1 | 0.78 |
| ORM1 | PON1 | 0.78 |
| PON1 | NA | 0.77 |
| GP5 | PON1 | 0.77 |
| CLEC3B | SELL | 0.77 |
| LCP1 | PDLIM1 | 0.77 |
| PON1 | SELL | 0.77 |
| CA2 | PON1 | 0.77 |
| ORM1 | SELL | 0.77 |
| LPA | PON1 | 0.77 |
| PTGDS | THBS1 | 0.77 |
| COMP | SELL | 0.77 |
| MASP1 | PON1 | 0.77 |
| IGFALS | VWF | 0.77 |
| SELL | VWF | 0.77 |
| NID1 | PON1 | 0.77 |
| MAN1A1 | PON1 | 0.77 |
| HABP2 | PON1 | 0.77 |
| CDH5 | PON1 | 0.77 |
| ORM1 | THBS1 | 0.77 |
| LCP1 | NA | 0.77 |
| PON1 | S100A8 | 0.77 |
| PDLIM1 | PFN1 | 0.77 |
| GPX3 | PON1 | 0.77 |
| PON1 | PTGDS | 0.77 |
| IGFALS | PON1 | 0.77 |
| COMP | PON1 | 0.77 |
| CD163 | PON1 | 0.77 |
| LCP1 | VWF | 0.77 |
| PON1 | TAGLN2 | 0.77 |
| PFN1 | PON1 | 0.77 |
| HABP2 | PDLIM1 | 0.77 |
| CA1 | PON1 | 0.77 |
| IGFALS | NA | 0.76 |
| CLEC3B | PON1 | 0.76 |
| S100A8 | SELL | 0.76 |
| PON1 | SEPP1 | 0.76 |
| PON1 | SPP2 | 0.76 |
| IGF2 | PON1 | 0.76 |
| IGFBP3 | PON1 | 0.76 |
| CNDP1 | PON1 | 0.76 |
| NCAM1 | PON1 | 0.76 |
| LGALS3BP | PON1 | 0.76 |
| APOC3 | PON1 | 0.76 |
| GP1BA | PON1 | 0.76 |
| PON1 | TGFBI | 0.76 |
| SELL | NA | 0.76 |
| PEPD | PON1 | 0.76 |
| GPLD1 | PON1 | 0.76 |
| LRG1 | PON1 | 0.76 |
| APOE | PON1 | 0.76 |
| BCHE | PON1 | 0.76 |
| S100A8 | THBS1 | 0.76 |
| ORM1 | PDLIM1 | 0.76 |
| PON1 | VCAM1 | 0.76 |
| PON1 | PRG4 | 0.76 |
| PON1 | QSOX1 | 0.76 |
| MASP2 | PON1 | 0.76 |
| CPN1 | PON1 | 0.76 |
| FCN3 | PON1 | 0.76 |
| APOA4 | PON1 | 0.76 |
| HYOU1 | PON1 | 0.76 |
| MINPP1 | PON1 | 0.76 |
| CLU | PON1 | 0.76 |
| CPN2 | PON1 | 0.76 |
| CLU | THBS1 | 0.76 |
| PON1 | SHBG | 0.76 |
| LCAT | PON1 | 0.76 |
| ORM1 | TNXB | 0.76 |
| HABP2 | MST1 | 0.76 |
| APOA1 | PON1 | 0.76 |
| CPB2 | PON1 | 0.76 |
| HABP2 | NA | 0.76 |
| PON1 | TNXB | 0.75 |
| ATRN | PON1 | 0.75 |
| ORM1 | VWF | 0.75 |
| LCP1 | SELL | 0.75 |
| COMP | HABP2 | 0.75 |
| BTD | COMP | 0.75 |
| PGLYRP2 | PON1 | 0.75 |
| IGFALS | ORM1 | 0.75 |
| BTD | PON1 | 0.75 |
| CACNA2D1 | ECM1 | 0.75 |
| IGFBP3 | ORM1 | 0.75 |
| BTD | PDLIM1 | 0.75 |
| LCP1 | QSOX1 | 0.75 |
| PON1 | S100A9 | 0.75 |
| QSOX1 | SELL | 0.75 |
| CLEC3B | LCP1 | 0.75 |
| CKM | PON1 | 0.75 |
| THBS1 | VTN | 0.75 |
| HGFAC | PON1 | 0.75 |
| MST1 | SELL | 0.75 |
| S100A9 | SELL | 0.75 |
| HABP2 | SELL | 0.75 |
| MINPP1 | THBS1 | 0.75 |
| MST1 | PON1 | 0.75 |
| PON1 | VASN | 0.75 |
| LUM | PON1 | 0.75 |
| DBH | PON1 | 0.75 |
| PDLIM1 | S100A8 | 0.75 |
| CNDP1 | HABP2 | 0.75 |
| LRG1 | PDLIM1 | 0.75 |
| HABP2 | VWF | 0.75 |
| LCAT | LCP1 | 0.75 |
| LRG1 | SELL | 0.75 |
| ATRN | THBS1 | 0.75 |
| PON1 | VTN | 0.75 |
| CPN1 | SELL | 0.75 |
| LCP1 | PRDX2 | 0.75 |
| CLEC3B | HABP2 | 0.75 |
| CD14 | THBS1 | 0.75 |

TABLE 2-continued

Panel Combinations of Two Candidate Latent TB Biomarkers

| protein.1 | protein.2 | AUC |
|---|---|---|
| IGFALS | SELL | 0.75 |
| BTD | ORM1 | 0.75 |
| BTD | LCP1 | 0.75 |
| CD14 | SELL | 0.75 |
| BTD | CLEC3B | 0.75 |
| LRG1 | THBS1 | 0.75 |
| CA2 | LCP1 | 0.74 |
| IGFALS | PDLIM1 | 0.74 |
| PRDX2 | SELL | 0.74 |
| PCSK9 | PON1 | 0.74 |
| CDH5 | THBS1 | 0.74 |
| PON1 | PROS1 | 0.74 |
| IGFBP3 | VWF | 0.74 |
| ORM1 | NA | 0.74 |
| CD14 | VWF | 0.74 |
| LCAT | SELL | 0.74 |
| HABP2 | LCP1 | 0.74 |
| CD14 | PDLIM1 | 0.74 |
| APOA4 | THBS1 | 0.74 |
| CPN1 | LCP1 | 0.74 |
| MAN1A1 | SELL | 0.74 |
| CNDP1 | LCP1 | 0.74 |
| BTD | VWF | 0.74 |
| LCP1 | TGFBI | 0.74 |
| MASP1 | SELL | 0.74 |
| GP1BA | SELL | 0.74 |
| IGFBP3 | LCP1 | 0.74 |
| CKM | SELL | 0.74 |
| IGFALS | LCP1 | 0.74 |
| GPX3 | SELL | 0.74 |
| BCHE | SELL | 0.74 |
| IGFBP3 | PDLIM1 | 0.74 |
| CPN1 | PDLIM1 | 0.74 |
| CD163 | SELL | 0.74 |
| LCP1 | LGALS3BP | 0.74 |
| CPN2 | SELL | 0.74 |
| SELL | TGFBI | 0.74 |
| SELL | SPP2 | 0.74 |
| LCP1 | MASP2 | 0.74 |
| LCP1 | ORM1 | 0.74 |
| APOC1 | LCP1 | 0.74 |
| NID1 | SELL | 0.74 |
| CNTN1 | ECM1 | 0.74 |
| LRG1 | VWF | 0.74 |
| SELL | TLN1 | 0.74 |
| BCHE | LCP1 | 0.74 |
| CA1 | SELL | 0.73 |
| NCAM1 | SELL | 0.73 |
| CLU | SELL | 0.73 |
| SELL | SEPP1 | 0.73 |
| THBS1 | TNXB | 0.73 |
| FCN3 | LCP1 | 0.73 |
| CNDP1 | SELL | 0.73 |
| HABP2 | SEPP1 | 0.73 |
| HABP2 | ORM1 | 0.73 |
| MASP2 | SELL | 0.73 |
| CPN2 | THBS1 | 0.73 |
| NCAM1 | THBS1 | 0.73 |
| LPA | SELL | 0.73 |
| CDH5 | SELL | 0.73 |
| IGFBP3 | SELL | 0.73 |
| PEPD | SELL | 0.73 |
| HABP2 | PRDX2 | 0.73 |
| CA2 | SELL | 0.73 |
| SELL | VCAM1 | 0.73 |
| LCP1 | TNXB | 0.73 |
| APOE | SELL | 0.73 |
| PDLIM1 | VTN | 0.73 |
| LPA | ORM1 | 0.73 |
| THBS1 | VWF | 0.73 |
| APOA4 | COMP | 0.73 |
| FCN3 | SELL | 0.73 |
| HABP2 | QSOX1 | 0.73 |
| LGALS3BP | SELL | 0.73 |
| CD163 | LCP1 | 0.73 |
| MASP1 | PDLIM1 | 0.73 |
| PDLIM1 | PTGDS | 0.73 |
| LCP1 | TLN1 | 0.73 |
| VTN | VWF | 0.73 |
| GPLD1 | SELL | 0.73 |
| HABP2 | TNXB | 0.73 |
| CPN1 | THBS1 | 0.73 |
| GPX3 | LCP1 | 0.73 |
| ORM1 | PTGDS | 0.73 |
| APOE | LCP1 | 0.73 |
| CD14 | COMP | 0.73 |
| CPB2 | LCP1 | 0.73 |
| HABP2 | MASP2 | 0.73 |
| LCP1 | LPA | 0.73 |
| CD14 | NA | 0.73 |
| PRG4 | SELL | 0.73 |
| CDH5 | LCP1 | 0.73 |
| LCP1 | NID1 | 0.73 |
| HABP2 | TGFBI | 0.73 |
| LCP1 | NCAM1 | 0.73 |
| CD14 | IGFALS | 0.73 |
| CD14 | LCP1 | 0.73 |
| CLEC3B | IGFALS | 0.73 |
| APOA4 | ORM1 | 0.73 |
| APOC1 | SELL | 0.73 |
| CLU | PDLIM1 | 0.73 |
| APOC3 | SELL | 0.73 |
| HABP2 | IGFALS | 0.73 |
| IGFALS | S100A8 | 0.73 |
| IGF2 | SELL | 0.73 |
| LCP1 | PEPD | 0.73 |
| LCP1 | SPP2 | 0.73 |
| CPB2 | SELL | 0.73 |
| LCP1 | S100A8 | 0.73 |
| SELL | SHBG | 0.73 |
| GP5 | SELL | 0.73 |
| CA1 | LCP1 | 0.73 |
| CA2 | HABP2 | 0.73 |
| HABP2 | LCAT | 0.73 |
| APOA4 | VWF | 0.73 |
| LCP1 | PCSK9 | 0.73 |
| IGFALS | PRDX2 | 0.73 |
| VWF | NA | 0.73 |
| LCP1 | MINPP1 | 0.73 |
| BTD | SELL | 0.73 |
| MASP1 | VWF | 0.73 |
| IGFBP3 | PROS1 | 0.73 |
| TNXB | VWF | 0.73 |
| APOC3 | HABP2 | 0.73 |
| PDLIM1 | VWF | 0.73 |
| HABP2 | IGFBP3 | 0.73 |
| HGFAC | LCP1 | 0.73 |
| LCP1 | MASP1 | 0.73 |
| HGFAC | SELL | 0.73 |
| CA1 | IGFALS | 0.73 |
| APOC3 | LCP1 | 0.73 |
| LCP1 | LUM | 0.73 |
| COMP | LCP1 | 0.73 |
| HABP2 | PCSK9 | 0.73 |
| PGLYRP2 | SELL | 0.73 |
| GP1BA | LCP1 | 0.73 |
| ATRN | LCP1 | 0.73 |
| LCP1 | PTGDS | 0.73 |
| HABP2 | S100A8 | 0.73 |
| CLU | VWF | 0.72 |
| APOA4 | SELL | 0.72 |
| APOE | HABP2 | 0.72 |
| LUM | ORM1 | 0.72 |
| LCP1 | MST1 | 0.72 |
| BTD | NA | 0.72 |
| MINPP1 | SELL | 0.72 |
| CD14 | VCAM1 | 0.72 |
| HABP2 | MAN1A1 | 0.72 |
| ORM1 | VTN | 0.72 |
| MASP1 | THBS1 | 0.72 |

TABLE 2-continued

Panel Combinations of Two Candidate Latent TB Biomarkers

| protein.1 | protein.2 | AUC |
|---|---|---|
| LCP1 | SHBG | 0.72 |
| BTD | HABP2 | 0.72 |
| S100A8 | VWF | 0.72 |
| SELL | TNXB | 0.72 |
| APOA4 | CLEC3B | 0.72 |
| CPN1 | IGFALS | 0.72 |
| PROS1 | SELL | 0.72 |
| IGFALS | LRG1 | 0.72 |
| LCP1 | SEPP1 | 0.72 |
| CDH5 | ORM1 | 0.72 |
| CD163 | VWF | 0.72 |
| PTGDS | SELL | 0.72 |
| APOA4 | PDLIM1 | 0.72 |
| COMP | TNXB | 0.72 |
| SELL | VTN | 0.72 |
| DBH | SELL | 0.72 |
| PCSK9 | SELL | 0.72 |
| GP5 | HABP2 | 0.72 |
| CD14 | HABP2 | 0.72 |
| BTD | LRG1 | 0.72 |
| APOA1 | SELL | 0.72 |
| BTD | S100A8 | 0.72 |
| IGF2 | LCP1 | 0.72 |
| BCHE | THBS1 | 0.72 |
| LUM | SELL | 0.72 |
| ATRN | ORM1 | 0.72 |
| CD14 | IGFBP3 | 0.72 |
| GP5 | LCP1 | 0.72 |
| GPLD1 | LCP1 | 0.72 |
| MASP2 | ORM1 | 0.72 |
| APOC1 | HABP2 | 0.72 |
| SELL | TAGLN2 | 0.72 |
| HYOU1 | THBS1 | 0.72 |
| ATRN | SELL | 0.72 |
| LCAT | ORM1 | 0.72 |
| BTD | PRDX2 | 0.72 |
| CLU | LCP1 | 0.72 |
| LCP1 | PFN1 | 0.72 |
| LCP1 | VCAM1 | 0.72 |
| BTD | IGFALS | 0.72 |
| ORM1 | QSOX1 | 0.72 |
| PFN1 | SELL | 0.72 |
| CPB2 | HABP2 | 0.72 |
| ORM1 | PRDX2 | 0.72 |
| LCP1 | PRG4 | 0.72 |
| MST1 | ORM1 | 0.72 |
| CNTN1 | PON1 | 0.72 |
| HABP2 | LUM | 0.72 |
| HABP2 | PTGDS | 0.72 |
| IGFBP3 | S100A8 | 0.72 |
| APOA1 | HABP2 | 0.72 |
| CD163 | IGFALS | 0.72 |
| HABP2 | LRG1 | 0.72 |
| SELL | VASN | 0.72 |
| HYOU1 | SELL | 0.72 |
| LCP1 | PROS1 | 0.72 |
| HABP2 | SPP2 | 0.72 |
| S100A8 | TNXB | 0.72 |
| CD14 | TNXB | 0.72 |
| MASP1 | ORM1 | 0.72 |
| IGFALS | S100A9 | 0.72 |
| HABP2 | SHBG | 0.72 |
| LUM | VWF | 0.72 |
| LCP1 | VASN | 0.72 |
| CA2 | IGFALS | 0.72 |
| CA1 | HABP2 | 0.72 |
| CPN1 | HABP2 | 0.72 |
| IGF2 | ORM1 | 0.72 |
| LCP1 | PGLYRP2 | 0.72 |
| HABP2 | PRG4 | 0.72 |
| LCP1 | MAN1A1 | 0.72 |
| CD14 | LCAT | 0.72 |
| CNDP1 | ORM1 | 0.72 |
| LCP1 | S100A9 | 0.72 |
| IGFALS | LGALS3BP | 0.71 |
| HABP2 | NCAM1 | 0.71 |
| GPX3 | HABP2 | 0.71 |
| CD14 | QSOX1 | 0.71 |
| CD163 | HABP2 | 0.71 |
| APOA1 | LCP1 | 0.71 |
| CDH5 | HABP2 | 0.71 |
| S100A9 | THBS1 | 0.71 |
| HABP2 | TLN1 | 0.71 |
| FCN3 | HABP2 | 0.71 |
| COMP | IGFALS | 0.71 |
| HABP2 | MASP1 | 0.71 |
| CKM | LCP1 | 0.71 |
| CPN1 | IGFBP3 | 0.71 |
| IGFBP3 | LRG1 | 0.71 |
| PTGDS | VWF | 0.71 |
| GP5 | IGFALS | 0.71 |
| LRG1 | TNXB | 0.71 |
| CPN2 | VWF | 0.71 |
| NCAM1 | VWF | 0.71 |
| CD163 | THBS1 | 0.71 |
| CPN2 | PDLIM1 | 0.71 |
| ORM1 | S100A8 | 0.71 |
| APOA4 | S100A8 | 0.71 |
| FCN3 | IGFALS | 0.71 |
| PDLIM1 | PRG4 | 0.71 |
| HYOU1 | LCP1 | 0.71 |
| LCP1 | TAGLN2 | 0.71 |
| BTD | GP5 | 0.71 |
| GP1BA | HABP2 | 0.71 |
| HABP2 | HGFAC | 0.71 |
| CD14 | MST1 | 0.71 |
| CD14 | LPA | 0.71 |
| CA2 | ORM1 | 0.71 |
| DBH | LCP1 | 0.71 |
| APOA4 | LCP1 | 0.71 |
| APOE | IGFALS | 0.71 |
| LCP1 | LRG1 | 0.71 |
| IGFALS | LPA | 0.71 |
| ORM1 | SPP2 | 0.71 |
| IGFALS | PCSK9 | 0.71 |
| IGFALS | MASP1 | 0.71 |
| COMP | ORM1 | 0.71 |
| BTD | S100A9 | 0.71 |
| NCAM1 | ORM1 | 0.71 |
| FCN3 | ORM1 | 0.71 |
| HABP2 | VCAM1 | 0.71 |
| BTD | CD14 | 0.71 |
| HABP2 | LPA | 0.71 |
| LCP1 | VTN | 0.71 |
| ORM1 | TLN1 | 0.71 |
| APOC1 | IGFALS | 0.71 |
| APOE | ORM1 | 0.71 |
| CD14 | VTN | 0.71 |
| CACNA2D1 | PON1 | 0.71 |
| PGLYRP2 | VWF | 0.71 |
| PDLIM1 | TNXB | 0.71 |
| IGFALS | TGFBI | 0.71 |
| CPN1 | VWF | 0.71 |
| HABP2 | VASN | 0.71 |
| IGFALS | TNXB | 0.71 |
| ORM1 | SHBG | 0.71 |
| CNDP1 | IGFALS | 0.71 |
| ORM1 | VCAM1 | 0.71 |
| GPLD1 | ORM1 | 0.71 |
| HABP2 | S100A9 | 0.71 |
| ORM1 | PGLYRP2 | 0.71 |
| HABP2 | PEPD | 0.71 |
| APOE | VWF | 0.71 |
| CA1 | ORM1 | 0.71 |
| CKM | ORM1 | 0.71 |
| BCHE | HABP2 | 0.71 |
| IGFALS | PTGDS | 0.71 |
| IGFALS | SPP2 | 0.71 |
| APOA4 | PRDX2 | 0.71 |
| MASP1 | PTGDS | 0.71 |

TABLE 2-continued

Panel Combinations of Two Candidate Latent TB Biomarkers

| protein.1 | protein.2 | AUC |
|---|---|---|
| APOC3 | ORM1 | 0.71 |
| IGFALS | MASP2 | 0.71 |
| HABP2 | LGALS3BP | 0.71 |
| LPA | MASP1 | 0.71 |
| CPB2 | IGFALS | 0.71 |
| S100A8 | NA | 0.71 |
| COMP | LUM | 0.71 |
| HGFAC | ORM1 | 0.71 |
| CPN1 | ORM1 | 0.71 |
| GP1BA | THBS1 | 0.71 |
| CLU | HABP2 | 0.71 |
| HYOU1 | VWF | 0.71 |
| CD14 | ORM1 | 0.71 |
| BCHE | IGFALS | 0.71 |
| IGFALS | PEPD | 0.71 |
| HABP2 | PGLYRP2 | 0.71 |
| CD163 | ORM1 | 0.71 |
| DBH | HABP2 | 0.71 |
| S100A9 | TNXB | 0.71 |
| LUM | THBS1 | 0.71 |
| CD14 | PTGDS | 0.71 |
| HYOU1 | PDLIM1 | 0.71 |
| CLEC3B | ORM1 | 0.70 |
| APOA4 | CD14 | 0.70 |
| BCHE | ORM1 | 0.70 |
| ATRN | IGFALS | 0.70 |
| APOC1 | ORM1 | 0.70 |
| LRG1 | NA | 0.70 |
| CLU | ORM1 | 0.70 |
| APOA1 | PDLIM1 | 0.70 |
| PTGDS | NA | 0.70 |
| CD14 | MASP2 | 0.70 |
| NID1 | ORM1 | 0.70 |
| BTD | CA1 | 0.70 |
| IGFALS | PROS1 | 0.70 |
| ATRN | HABP2 | 0.70 |
| BTD | IGFBP3 | 0.70 |
| CACNA2D1 | ORM1 | 0.70 |
| VTN | NA | 0.70 |
| CD14 | CNDP1 | 0.70 |
| BTD | FCN3 | 0.70 |
| HABP2 | PFN1 | 0.70 |
| IGFBP3 | S100A9 | 0.70 |
| IGFALS | LUM | 0.70 |
| ORM1 | PRG4 | 0.70 |
| PROS1 | VWF | 0.70 |
| PRG4 | VWF | 0.70 |
| LGALS3BP | ORM1 | 0.70 |
| CD163 | PDLIM1 | 0.70 |
| GPLD1 | HABP2 | 0.70 |
| HABP2 | NID1 | 0.70 |
| GP1BA | ORM1 | 0.70 |
| NID1 | THBS1 | 0.70 |
| ORM1 | PCSK9 | 0.70 |
| CDH5 | MASP1 | 0.70 |
| HABP2 | TAGLN2 | 0.70 |
| HABP2 | IGF2 | 0.70 |
| S100A9 | VWF | 0.70 |
| CPN2 | LCP1 | 0.70 |
| GPX3 | IGFALS | 0.70 |
| CDH5 | PDLIM1 | 0.70 |
| ORM1 | SEPP1 | 0.70 |
| BTD | QSOX1 | 0.70 |
| IGFALS | VTN | 0.70 |
| PDLIM1 | PGLYRP2 | 0.70 |
| HABP2 | VTN | 0.70 |
| TLN1 | VTN | 0.70 |
| PCSK9 | VWF | 0.70 |
| APOA1 | IGFALS | 0.70 |
| APOE | CD14 | 0.70 |
| CD14 | CLEC3B | 0.70 |
| QSOX1 | THBS1 | 0.70 |
| CDH5 | IGFALS | 0.70 |
| ORM1 | PROS1 | 0.70 |
| CD14 | FCN3 | 0.70 |
| ORM1 | S100A9 | 0.70 |
| CKM | HABP2 | 0.70 |
| HABP2 | PROS1 | 0.70 |
| CPB2 | THBS1 | 0.70 |
| APOC3 | IGFALS | 0.70 |
| LPA | LRG1 | 0.70 |
| BCHE | VWF | 0.70 |
| PDLIM1 | S100A9 | 0.70 |
| GPX3 | ORM1 | 0.70 |
| CPN2 | ORM1 | 0.70 |
| APOC3 | VWF | 0.70 |
| IGFALS | NID1 | 0.70 |
| APOA1 | THBS1 | 0.70 |
| MAN1A1 | ORM1 | 0.70 |
| APOC3 | THBS1 | 0.70 |
| S100A8 | VTN | 0.70 |
| BTD | CA2 | 0.70 |
| LPA | VWF | 0.70 |
| MINPP1 | ORM1 | 0.70 |
| BTD | LPA | 0.70 |
| CPB2 | ORM1 | 0.70 |
| APOA4 | NA | 0.70 |
| IGFALS | SHBG | 0.70 |
| APOA4 | HABP2 | 0.70 |
| BTD | TNXB | 0.70 |
| IGFALS | PRG4 | 0.70 |
| DBH | ORM1 | 0.70 |
| IGFBP3 | NA | 0.70 |
| GPX3 | PDLIM1 | 0.70 |
| NID1 | VWF | 0.70 |
| CLU | IGFALS | 0.70 |
| VASN | VWF | 0.70 |
| CD163 | PTGDS | 0.70 |
| ORM1 | PEPD | 0.70 |
| QSOX1 | VWF | 0.70 |
| CPN2 | IGFALS | 0.70 |
| BTD | CDH5 | 0.70 |
| GP1BA | IGFALS | 0.70 |
| CD14 | CDH5 | 0.70 |
| CDH5 | VWF | 0.70 |
| HABP2 | HYOU1 | 0.70 |
| CD14 | S100A8 | 0.70 |
| ORM1 | TGFBI | 0.70 |
| IGFALS | TLN1 | 0.70 |
| NCAM1 | PDLIM1 | 0.70 |
| CD14 | NID1 | 0.70 |
| GP5 | ORM1 | 0.70 |
| APOC1 | BTD | 0.70 |
| HYOU1 | ORM1 | 0.70 |
| ORM1 | PFN1 | 0.70 |
| ATRN | VWF | 0.70 |
| BTD | CD163 | 0.70 |
| BTD | PTGDS | 0.70 |
| ORM1 | VASN | 0.70 |
| ATRN | S100A8 | 0.70 |
| IGFALS | IGFBP3 | 0.70 |
| IGFALS | NCAM1 | 0.70 |
| GPLD1 | IGFALS | 0.70 |
| CACNA2D1 | CD14 | 0.70 |
| CD14 | CLU | 0.69 |
| CPN1 | TNXB | 0.69 |
| CPN2 | HABP2 | 0.69 |
| APOA4 | LRG1 | 0.69 |
| CPN2 | S100A8 | 0.69 |
| APOA1 | ORM1 | 0.69 |
| CPN1 | PTGDS | 0.69 |
| ORM1 | TAGLN2 | 0.69 |
| APOC3 | CD14 | 0.69 |
| BTD | CLU | 0.69 |
| LRG1 | ORM1 | 0.69 |
| APOA4 | IGFALS | 0.69 |
| PDLIM1 | SEPP1 | 0.69 |
| IGFALS | SEPP1 | 0.69 |
| PTGDS | S100A8 | 0.69 |
| IGFALS | QSOX1 | 0.69 |

TABLE 2-continued

Panel Combinations of Two Candidate Latent TB Biomarkers

| protein.1 | protein.2 | AUC |
|---|---|---|
| CD14 | CPN1 | 0.69 |
| CLU | IGFBP3 | 0.69 |
| BTD | CPN1 | 0.69 |
| BTD | PROS1 | 0.69 |
| GP1BA | VWF | 0.69 |
| ATRN | CD14 | 0.69 |
| LUM | S100A8 | 0.69 |
| APOA4 | LPA | 0.69 |
| CD14 | TLN1 | 0.69 |
| CPN2 | IGFBP3 | 0.69 |
| CD14 | PCSK9 | 0.69 |
| HYOU1 | IGFALS | 0.69 |
| APOC3 | BTD | 0.69 |
| APOA4 | S100A9 | 0.69 |
| CD14 | CPN2 | 0.69 |
| CD14 | SHBG | 0.69 |
| LUM | PDLIM1 | 0.69 |
| PGLYRP2 | VTN | 0.69 |
| PRDX2 | S100A8 | 0.69 |
| BTD | CNDP1 | 0.69 |
| TAGLN2 | VWF | 0.69 |
| BTD | MST1 | 0.69 |
| CD14 | SPP2 | 0.69 |
| BTD | MASP2 | 0.69 |
| PGLYRP2 | THBS1 | 0.69 |
| BTD | GPX3 | 0.69 |
| APOA4 | APOC1 | 0.69 |
| CDH5 | CPN1 | 0.69 |
| PROS1 | S100A8 | 0.69 |
| CNDP1 | VWF | 0.69 |
| IGFALS | LCAT | 0.69 |
| CNTN1 | LCP1 | 0.69 |
| TNXB | VTN | 0.69 |
| CD14 | TGFBI | 0.69 |
| IGFALS | MST1 | 0.69 |
| IGFBP3 | VTN | 0.69 |
| CPB2 | VWF | 0.69 |
| LGALS3BP | VWF | 0.69 |
| GPX3 | VWF | 0.69 |
| CD14 | MAN1A1 | 0.69 |
| LRG1 | VTN | 0.69 |
| CD14 | MASP1 | 0.69 |
| BTD | GP1BA | 0.69 |
| BTD | NID1 | 0.69 |
| BTD | SEPP1 | 0.69 |
| CACNA2D1 | SELL | 0.69 |
| PDLIM1 | QSOX1 | 0.69 |
| CD14 | GPLD1 | 0.69 |
| PEPD | VWF | 0.69 |
| BTD | SHBG | 0.69 |
| IGF2 | IGFALS | 0.69 |
| CDH5 | NA | 0.69 |
| GPLD1 | VWF | 0.69 |
| CKM | IGFALS | 0.69 |
| CD14 | PRDX2 | 0.69 |
| MAN1A1 | PDLIM1 | 0.69 |
| APOE | THBS1 | 0.69 |
| GPLD1 | PDLIM1 | 0.69 |
| CD14 | IGF2 | 0.69 |
| MASP1 | S100A8 | 0.69 |
| IGFALS | MINPP1 | 0.69 |
| MASP2 | VWF | 0.69 |
| COMP | MASP1 | 0.69 |
| BTD | VTN | 0.69 |
| CPN1 | NA | 0.69 |
| PTGDS | VTN | 0.69 |
| BTD | PCSK9 | 0.69 |
| IGFBP3 | MASP1 | 0.69 |
| APOA4 | CA1 | 0.69 |
| CD14 | CD163 | 0.69 |
| PGLYRP2 | PTGDS | 0.69 |
| BCHE | CD14 | 0.69 |
| HABP2 | MINPP1 | 0.69 |
| BTD | CPB2 | 0.69 |
| APOA4 | CD163 | 0.69 |
| CPB2 | PDLIM1 | 0.69 |
| GPX3 | IGFBP3 | 0.69 |
| LPA | PGLYRP2 | 0.69 |
| CD14 | GP1BA | 0.69 |
| PRDX2 | VWF | 0.69 |
| COMP | IGFBP3 | 0.69 |
| PFN1 | VWF | 0.69 |
| ATRN | LRG1 | 0.69 |
| COMP | HYOU1 | 0.69 |
| ATRN | PDLIM1 | 0.69 |
| GP5 | VWF | 0.69 |
| IGFALS | MAN1A1 | 0.69 |
| BCHE | BTD | 0.69 |
| BCHE | PDLIM1 | 0.69 |
| BTD | CKM | 0.69 |
| CNTN1 | SELL | 0.69 |
| CPN2 | TNXB | 0.69 |
| CD14 | LGALS3BP | 0.69 |
| APOA4 | BTD | 0.69 |
| CD14 | GP5 | 0.69 |
| PRG4 | S100A8 | 0.69 |
| DBH | IGFALS | 0.69 |
| APOA4 | CPN1 | 0.69 |
| PROS1 | TNXB | 0.69 |
| BTD | LUM | 0.69 |
| BTD | NCAM1 | 0.69 |
| BTD | SPP2 | 0.69 |
| CACNA2D1 | LCP1 | 0.69 |
| IGFBP3 | PTGDS | 0.69 |
| PCSK9 | PTGDS | 0.69 |
| LRG1 | MASP1 | 0.69 |
| APOA4 | NID1 | 0.69 |
| MST1 | VWF | 0.69 |
| APOA4 | CA2 | 0.69 |
| HGFAC | VWF | 0.69 |
| FCN3 | PTGDS | 0.68 |
| CACNA2D1 | VWF | 0.68 |
| CD14 | NCAM1 | 0.68 |
| CLEC3B | VWF | 0.68 |
| LRG1 | QSOX1 | 0.68 |
| MAN1A1 | VWF | 0.68 |
| SHBG | VWF | 0.68 |
| CD14 | CPB2 | 0.68 |
| CD14 | HGFAC | 0.68 |
| LRG1 | LUM | 0.68 |
| APOE | BTD | 0.68 |
| BTD | MAN1A1 | 0.68 |
| CD14 | HYOU1 | 0.68 |
| CA2 | S100A8 | 0.68 |
| CD14 | S100A9 | 0.68 |
| CD14 | MINPP1 | 0.68 |
| CPN1 | PGLYRP2 | 0.68 |
| LPA | VTN | 0.68 |
| FCN3 | VWF | 0.68 |
| CPN2 | PTGDS | 0.68 |
| MASP1 | TNXB | 0.68 |
| NCAM1 | S100A8 | 0.68 |
| GPLD1 | S100A8 | 0.68 |
| APOA1 | IGFBP3 | 0.68 |
| APOA1 | VWF | 0.68 |
| IGFALS | VCAM1 | 0.68 |
| COMP | VTN | 0.68 |
| LGALS3BP | PTGDS | 0.68 |
| PROS1 | THBS1 | 0.68 |
| BTD | HGFAC | 0.68 |
| APOC1 | PTGDS | 0.68 |
| CDH5 | VTN | 0.68 |
| CD163 | NA | 0.68 |
| APOA4 | TNXB | 0.68 |
| PRDX2 | VTN | 0.68 |
| IGFBP3 | TLN1 | 0.68 |
| APOA1 | S100A8 | 0.68 |
| CPN1 | MASP1 | 0.68 |
| APOA4 | PTGDS | 0.68 |
| CLU | S100A8 | 0.68 |

TABLE 2-continued

Panel Combinations of Two Candidate Latent TB Biomarkers

| protein.1 | protein.2 | AUC |
|---|---|---|
| CLU | PGLYRP2 | 0.68 |
| CD14 | PRG4 | 0.68 |
| BTD | MASP1 | 0.68 |
| LRG1 | PROS1 | 0.68 |
| COMP | VWF | 0.68 |
| BTD | VASN | 0.68 |
| BTD | TGFBI | 0.68 |
| LPA | S100A8 | 0.68 |
| CD14 | TAGLN2 | 0.68 |
| MASP1 | NA | 0.68 |
| LRG1 | PGLYRP2 | 0.68 |
| LRG1 | PTGDS | 0.68 |
| LCAT | LRG1 | 0.68 |
| CD14 | SEPP1 | 0.68 |
| ATRN | BTD | 0.68 |
| LRG1 | S100A8 | 0.68 |
| CACNA2D1 | HABP2 | 0.68 |
| GP5 | VTN | 0.68 |
| PRDX2 | PTGDS | 0.68 |
| LRG1 | TLN1 | 0.68 |
| CD14 | LUM | 0.68 |
| NID1 | VTN | 0.68 |
| COMP | CPN2 | 0.68 |
| LUM | NA | 0.68 |
| BTD | IGF2 | 0.68 |
| CLU | TNXB | 0.68 |
| BTD | GPLD1 | 0.68 |
| BTD | TLN1 | 0.68 |
| LGALS3BP | S100A8 | 0.68 |
| LGALS3BP | PDLIM1 | 0.68 |
| SPP2 | VWF | 0.68 |
| TGFBI | THBS1 | 0.68 |
| TNXB | NA | 0.68 |
| CPB2 | IGFBP3 | 0.68 |
| APOA4 | APOE | 0.68 |
| CA1 | VTN | 0.68 |
| CPN1 | LUM | 0.68 |
| CD14 | GPX3 | 0.68 |
| IGFBP3 | PRDX2 | 0.68 |
| APOA4 | QSOX1 | 0.68 |
| MAN1A1 | THBS1 | 0.68 |
| CACNA2D1 | LRG1 | 0.68 |
| CA2 | VTN | 0.68 |
| DBH | VWF | 0.68 |
| APOA4 | IGFBP3 | 0.68 |
| GPLD1 | THBS1 | 0.68 |
| CLU | MASP1 | 0.68 |
| IGFALS | PGLYRP2 | 0.68 |
| IGFALS | VASN | 0.68 |
| CA2 | CD14 | 0.68 |
| SEPP1 | VWF | 0.68 |
| CPN2 | LRG1 | 0.68 |
| BTD | VCAM1 | 0.68 |
| IGFALS | PFN1 | 0.68 |
| PRG4 | PTGDS | 0.68 |
| BTD | DBH | 0.68 |
| GPX3 | TNXB | 0.68 |
| CD14 | PROS1 | 0.68 |
| APOA4 | PCSK9 | 0.68 |
| QSOX1 | VTN | 0.68 |
| CD14 | DBH | 0.68 |
| CPN2 | NA | 0.68 |
| LCAT | VWF | 0.68 |
| CD14 | CKM | 0.68 |
| CD163 | VTN | 0.68 |
| IGF2 | VWF | 0.68 |
| HGFAC | IGFALS | 0.68 |
| PTGDS | S100A9 | 0.68 |
| TLN1 | VWF | 0.68 |
| CD14 | PEPD | 0.68 |
| BTD | TAGLN2 | 0.68 |
| TGFBI | VWF | 0.68 |
| CKM | VWF | 0.68 |
| APOA4 | CNDP1 | 0.68 |
| CD14 | PFN1 | 0.68 |
| BTD | PRG4 | 0.68 |
| LRG1 | PRDX2 | 0.68 |
| CD14 | LRG1 | 0.68 |
| CD163 | PROS1 | 0.68 |
| CPN1 | S100A8 | 0.68 |
| HYOU1 | PTGDS | 0.68 |
| CDH5 | S100A8 | 0.68 |
| BTD | MINPP1 | 0.68 |
| APOA4 | VTN | 0.68 |
| S100A9 | VTN | 0.68 |
| FCN3 | LRG1 | 0.68 |
| LPA | THBS1 | 0.68 |
| VCAM1 | VWF | 0.68 |
| IGFBP3 | LPA | 0.68 |
| BTD | PGLYRP2 | 0.68 |
| MASP1 | VTN | 0.68 |
| APOA4 | CDH5 | 0.68 |
| COMP | PTGDS | 0.68 |
| GPX3 | PTGDS | 0.68 |
| CA2 | VWF | 0.68 |
| CNTN1 | HABP2 | 0.68 |
| PGLYRP2 | S100A8 | 0.68 |
| ATRN | S100A9 | 0.68 |
| GPLD1 | LRG1 | 0.68 |
| PRG4 | THBS1 | 0.68 |
| BTD | PFN1 | 0.68 |
| BTD | CPN2 | 0.68 |
| CD163 | CDH5 | 0.68 |
| CA1 | S100A8 | 0.68 |
| GPX3 | THBS1 | 0.68 |
| MINPP1 | PDLIM1 | 0.68 |
| BTD | LCAT | 0.68 |
| CA1 | CD14 | 0.68 |
| CPN1 | VTN | 0.68 |
| PFN1 | VTN | 0.68 |
| COMP | NCAM1 | 0.68 |
| APOA1 | CD14 | 0.67 |
| CDH5 | CPN2 | 0.67 |
| APOC1 | CD14 | 0.67 |
| CDH5 | PRG4 | 0.67 |
| LPA | TNXB | 0.67 |
| CD163 | CPN1 | 0.67 |
| IGFALS | TAGLN2 | 0.67 |
| LPA | PTGDS | 0.67 |
| IGFBP3 | TNXB | 0.67 |
| FCN3 | S100A8 | 0.67 |
| CPB2 | PTGDS | 0.67 |
| BTD | LGALS3BP | 0.67 |
| APOA4 | NCAM1 | 0.67 |
| BTD | HYOU1 | 0.67 |
| MASP1 | PROS1 | 0.67 |
| SEPP1 | THBS1 | 0.67 |
| LUM | S100A9 | 0.67 |
| APOA4 | CLU | 0.67 |
| NID1 | PDLIM1 | 0.67 |
| CD163 | LPA | 0.67 |
| APOA4 | LUM | 0.67 |
| LRG1 | NCAM1 | 0.67 |
| CA1 | VWF | 0.67 |
| APOA4 | MST1 | 0.67 |
| PCSK9 | S100A8 | 0.67 |
| NID1 | PTGDS | 0.67 |
| IGFBP3 | PRG4 | 0.67 |
| S100A9 | NA | 0.67 |
| CDH5 | LRG1 | 0.67 |
| APOA4 | GP5 | 0.67 |
| APOE | S100A8 | 0.67 |
| PROS1 | VTN | 0.67 |
| CD14 | PGLYRP2 | 0.67 |
| APOA1 | TNXB | 0.67 |
| COMP | LRG1 | 0.67 |
| APOE | PTGDS | 0.67 |
| LRG1 | VCAM1 | 0.67 |
| CD163 | MASP1 | 0.67 |
| CD14 | VASN | 0.67 |

TABLE 2-continued

Panel Combinations of Two Candidate Latent TB Biomarkers

| protein.1 | protein.2 | AUC |
| --- | --- | --- |
| COMP | CPN1 | 0.67 |
| CLEC3B | PTGDS | 0.67 |
| QSOX1 | S100A8 | 0.67 |
| APOA4 | FCN3 | 0.67 |
| NCAM1 | VTN | 0.67 |
| CLEC3B | LRG1 | 0.67 |
| CPN1 | LPA | 0.67 |
| PTGDS | QSOX1 | 0.67 |
| APOA4 | CKM | 0.67 |
| PGLYRP2 | PROS1 | 0.67 |
| PROS1 | PTGDS | 0.67 |
| LUM | VTN | 0.67 |
| APOA4 | MASP1 | 0.67 |
| CDH5 | GPX3 | 0.67 |
| APOA4 | MASP2 | 0.67 |
| HYOU1 | S100A8 | 0.67 |
| APOC3 | LRG1 | 0.67 |
| APOA4 | CPB2 | 0.67 |
| CLU | LUM | 0.67 |
| CLEC3B | VTN | 0.67 |
| CA2 | PTGDS | 0.67 |
| SPP2 | VTN | 0.67 |
| CLU | NA | 0.67 |
| CNDP1 | LRG1 | 0.67 |
| LGALS3BP | LRG1 | 0.67 |
| GP1BA | S100A8 | 0.67 |
| APOA4 | LGALS3BP | 0.67 |
| BTD | PEPD | 0.67 |
| PRG4 | TNXB | 0.67 |
| APOA4 | APOC3 | 0.67 |
| APOE | VTN | 0.67 |
| APOA4 | PROS1 | 0.67 |
| APOE | LRG1 | 0.67 |
| MINPP1 | VWF | 0.67 |
| MASP1 | NCAM1 | 0.67 |
| S100A8 | S100A9 | 0.67 |
| GPLD1 | PTGDS | 0.67 |
| IGF2 | LRG1 | 0.67 |
| S100A8 | TLN1 | 0.67 |
| IGFBP3 | NCAM1 | 0.67 |
| CD163 | IGFBP3 | 0.67 |
| CDH5 | CLU | 0.67 |
| APOC3 | PTGDS | 0.67 |
| APOA4 | TGFBI | 0.67 |
| APOA4 | SPP2 | 0.67 |
| CPN1 | QSOX1 | 0.67 |
| CKM | LRG1 | 0.67 |
| CDH5 | PGLYRP2 | 0.67 |
| IGF2 | VTN | 0.67 |
| CNDP1 | VTN | 0.67 |
| CDH5 | HYOU1 | 0.67 |
| PEPD | THBS1 | 0.67 |
| LPA | LUM | 0.67 |
| APOC3 | VTN | 0.67 |
| CPN1 | LRG1 | 0.67 |
| HGFAC | S100A8 | 0.67 |
| APOA4 | SHBG | 0.67 |
| APOC1 | VWF | 0.67 |
| MASP2 | PTGDS | 0.67 |
| GP1BA | PDLIM1 | 0.67 |
| CDH5 | PRDX2 | 0.67 |
| APOC3 | S100A8 | 0.67 |
| APOA1 | BTD | 0.67 |
| LRG1 | NID1 | 0.67 |
| CPB2 | S100A8 | 0.67 |
| LPA | PDLIM1 | 0.67 |
| LRG1 | S100A9 | 0.67 |
| MAN1A1 | PTGDS | 0.67 |
| S100A8 | VASN | 0.67 |
| MASP1 | S100A9 | 0.67 |
| IGFBP3 | PGLYRP2 | 0.67 |
| FCN3 | VTN | 0.67 |
| PDLIM1 | TGFBI | 0.67 |
| NCAM1 | PTGDS | 0.67 |
| APOA4 | SEPP1 | 0.67 |
| BCHE | PTGDS | 0.67 |
| CACNA2D1 | S100A8 | 0.67 |
| CD163 | LRG1 | 0.67 |
| LRG1 | PFN1 | 0.67 |
| COMP | PGLYRP2 | 0.67 |
| APOA4 | GP1BA | 0.67 |
| NCAM1 | PRDX2 | 0.67 |
| CA2 | LRG1 | 0.67 |
| ATRN | IGFBP3 | 0.67 |
| GP5 | IGFBP3 | 0.67 |
| PTGDS | SHBG | 0.67 |
| APOA4 | HGFAC | 0.67 |
| APOA4 | CPN2 | 0.67 |
| LUM | PRDX2 | 0.67 |
| CLU | LPA | 0.67 |
| CA1 | IGFBP3 | 0.67 |
| CLU | TLN1 | 0.67 |
| CD163 | CPN2 | 0.67 |
| IGFBP3 | SPP2 | 0.67 |
| CKM | VTN | 0.67 |
| HGFAC | LRG1 | 0.67 |
| CPN2 | S100A9 | 0.67 |
| CLEC3B | S100A8 | 0.67 |
| S100A8 | SPP2 | 0.67 |
| LUM | PROS1 | 0.67 |
| APOE | PDLIM1 | 0.67 |
| BCHE | LRG1 | 0.67 |
| PFN1 | S100A8 | 0.67 |
| CD163 | S100A8 | 0.67 |
| CDH5 | PTGDS | 0.67 |
| GPX3 | VTN | 0.67 |
| CPN2 | LUM | 0.67 |
| APOA4 | MAN1A1 | 0.67 |
| APOA4 | GPX3 | 0.66 |
| GPLD1 | IGFBP3 | 0.66 |
| APOE | TNXB | 0.66 |
| CDH5 | GPLD1 | 0.66 |
| APOA1 | LRG1 | 0.66 |
| SPP2 | THBS1 | 0.66 |
| CDH5 | LPA | 0.66 |
| APOA4 | ATRN | 0.66 |
| S100A8 | TGFBI | 0.66 |
| PDLIM1 | PROS1 | 0.66 |
| SEPP1 | VTN | 0.66 |
| CNDP1 | PTGDS | 0.66 |
| GP1BA | LRG1 | 0.66 |
| FCN3 | IGFBP3 | 0.66 |
| TAGLN2 | VTN | 0.66 |
| LRG1 | PCSK9 | 0.66 |
| IGFBP3 | LGALS3BP | 0.66 |
| CD163 | TNXB | 0.66 |
| CLU | VTN | 0.66 |
| PROS1 | NA | 0.66 |
| CDH5 | PROS1 | 0.66 |
| CKM | S100A8 | 0.66 |
| IGF2 | S100A8 | 0.66 |
| S100A8 | SEPP1 | 0.66 |
| PRG4 | VTN | 0.66 |
| CA2 | IGFBP3 | 0.66 |
| TGFBI | VTN | 0.66 |
| CLU | PTGDS | 0.66 |
| CACNA2D1 | IGFALS | 0.66 |
| LRG1 | SHBG | 0.66 |
| HYOU1 | NA | 0.66 |
| CNDP1 | S100A8 | 0.66 |
| CA1 | LRG1 | 0.66 |
| CA1 | PTGDS | 0.66 |
| LRG1 | SPP2 | 0.66 |
| PTGDS | SEPP1 | 0.66 |
| LRG1 | MASP2 | 0.66 |
| VCAM1 | VTN | 0.66 |
| GP5 | S100A8 | 0.66 |
| CLU | LRG1 | 0.66 |
| PROS1 | S100A9 | 0.66 |
| HGFAC | VTN | 0.66 |

TABLE 2-continued

Panel Combinations of Two Candidate Latent TB Biomarkers

| protein.1 | protein.2 | AUC |
|---|---|---|
| PTGDS | TLN1 | 0.66 |
| PTGDS | TNXB | 0.66 |
| LRG1 | TAGLN2 | 0.66 |
| CPB2 | LRG1 | 0.66 |
| APOA4 | BCHE | 0.66 |
| CPN2 | VTN | 0.66 |
| IGFBP3 | MASP2 | 0.66 |
| PEPD | S100A8 | 0.66 |
| NCAM1 | TNXB | 0.66 |
| BCHE | VTN | 0.66 |
| APOA1 | APOA4 | 0.66 |
| NCAM1 | PROS1 | 0.66 |
| LRG1 | MST1 | 0.66 |
| PDLIM1 | SPP2 | 0.66 |
| CPB2 | VTN | 0.66 |
| CDH5 | CPB2 | 0.66 |
| LRG1 | PRG4 | 0.66 |
| DBH | PTGDS | 0.66 |
| IGF2 | PTGDS | 0.66 |
| NID1 | S100A8 | 0.66 |
| DBH | S100A8 | 0.66 |
| APOA4 | DBH | 0.66 |
| CNDP1 | CPN2 | 0.66 |
| CDH5 | IGFBP3 | 0.66 |
| LGALS3BP | TNXB | 0.66 |
| LGALS3BP | VTN | 0.66 |
| NCAM1 | NA | 0.66 |
| CDH5 | FCN3 | 0.66 |
| APOA1 | PTGDS | 0.66 |
| CPN1 | NCAM1 | 0.66 |
| LRG1 | VASN | 0.66 |
| CPN2 | LPA | 0.66 |
| LPA | S100A9 | 0.66 |
| LGALS3BP | THBS1 | 0.66 |
| VASN | VTN | 0.66 |
| CPN2 | PRDX2 | 0.66 |
| SEPP1 | TNXB | 0.66 |
| APOA4 | PRG4 | 0.66 |
| APOC1 | S100A8 | 0.66 |
| LRG1 | TGFBI | 0.66 |
| DBH | LRG1 | 0.66 |
| LUM | PTGDS | 0.66 |
| GP5 | LRG1 | 0.66 |
| FCN3 | LUM | 0.66 |
| MASP1 | NID1 | 0.66 |
| APOA4 | PEPD | 0.66 |
| LRG1 | MINPP1 | 0.66 |
| CD163 | CLU | 0.66 |
| HYOU1 | LPA | 0.66 |
| PGLYRP2 | TNXB | 0.66 |
| PCSK9 | VTN | 0.66 |
| CD163 | NCAM1 | 0.66 |
| MASP2 | VTN | 0.66 |
| PTGDS | TGFBI | 0.66 |
| ATRN | VTN | 0.66 |
| MASP1 | PCSK9 | 0.66 |
| HYOU1 | IGFBP3 | 0.66 |
| GPX3 | LRG1 | 0.66 |
| PRDX2 | TNXB | 0.66 |
| PTGDS | SPP2 | 0.66 |
| IGFBP3 | SEPP1 | 0.66 |
| CNTN1 | ORM1 | 0.66 |
| IGFBP3 | TGFBI | 0.66 |
| APOE | IGFBP3 | 0.66 |
| S100A8 | TAGLN2 | 0.66 |
| CDH5 | S100A9 | 0.66 |
| LRG1 | PEPD | 0.66 |
| FCN3 | TNXB | 0.66 |
| GPX3 | LUM | 0.66 |
| CPB2 | TNXB | 0.66 |
| SHBG | VTN | 0.66 |
| CLEC3B | CPN2 | 0.66 |
| APOA4 | VASN | 0.66 |
| APOC1 | VTN | 0.66 |
| CPN1 | HYOU1 | 0.66 |
| BCHE | CDH5 | 0.66 |
| APOA4 | HYOU1 | 0.66 |
| CNDP1 | IGFBP3 | 0.66 |
| IGFBP3 | LUM | 0.66 |
| ATRN | NA | 0.66 |
| IGFBP3 | PCSK9 | 0.66 |
| APOE | CDH5 | 0.66 |
| GP5 | PTGDS | 0.66 |
| GPX3 | S100A8 | 0.66 |
| APOA4 | PGLYRP2 | 0.66 |
| APOA4 | VCAM1 | 0.66 |
| HGFAC | PTGDS | 0.66 |
| MST1 | PTGDS | 0.66 |
| BCHE | S100A8 | 0.66 |
| APOC1 | CPN1 | 0.66 |
| APOA4 | GPLD1 | 0.66 |
| MAN1A1 | VTN | 0.66 |
| MST1 | S100A8 | 0.66 |
| CPN2 | NID1 | 0.66 |
| PGLYRP2 | NA | 0.66 |
| HYOU1 | LRG1 | 0.66 |
| COMP | S100A8 | 0.66 |
| GP1BA | IGFBP3 | 0.66 |
| CNTN1 | IGFALS | 0.66 |
| CPN1 | PRDX2 | 0.66 |
| CNDP1 | CPN1 | 0.66 |
| LCAT | VTN | 0.66 |
| IGFBP3 | NID1 | 0.66 |
| CKM | PTGDS | 0.66 |
| BCHE | CD163 | 0.66 |
| APOA4 | LCAT | 0.66 |
| ATRN | PTGDS | 0.66 |
| DBH | VTN | 0.66 |
| MASP1 | QSOX1 | 0.66 |
| BCHE | IGFBP3 | 0.66 |
| NCAM1 | S100A9 | 0.66 |
| CPN1 | VASN | 0.66 |
| S100A8 | SHBG | 0.66 |
| CDH5 | LGALS3BP | 0.66 |
| MINPP1 | PTGDS | 0.66 |
| IGFBP3 | MAN1A1 | 0.66 |
| CDH5 | QSOX1 | 0.66 |
| LUM | MASP1 | 0.66 |
| APOA1 | CDH5 | 0.66 |
| BTD | CNTN1 | 0.66 |
| CLEC3B | CPN1 | 0.65 |
| CPN1 | FCN3 | 0.65 |
| APOC1 | LRG1 | 0.65 |
| IGFBP3 | SHBG | 0.65 |
| LUM | PRG4 | 0.65 |
| MASP2 | TNXB | 0.65 |
| PRDX2 | S100A9 | 0.65 |
| APOA4 | TLN1 | 0.65 |
| GP1BA | PTGDS | 0.65 |
| CD163 | HYOU1 | 0.65 |
| CLU | COMP | 0.65 |
| ATRN | CD163 | 0.65 |
| MST1 | VTN | 0.65 |
| PTGDS | VCAM1 | 0.65 |
| PFN1 | THBS1 | 0.65 |
| PFN1 | PTGDS | 0.65 |
| APOA4 | MINPP1 | 0.65 |
| HYOU1 | PRDX2 | 0.65 |
| LCAT | PTGDS | 0.65 |
| CLU | NCAM1 | 0.65 |
| FCN3 | MASP1 | 0.65 |
| CDH5 | NCAM1 | 0.65 |
| CDH5 | PCSK9 | 0.65 |
| PTGDS | TAGLN2 | 0.65 |
| APOE | CPN1 | 0.65 |
| CD163 | GPX3 | 0.65 |
| CPN1 | GPX3 | 0.65 |
| NID1 | PROS1 | 0.65 |
| CNTN1 | MASP1 | 0.65 |
| CLU | S100A9 | 0.65 |

TABLE 2-continued

Panel Combinations of Two Candidate Latent TB Biomarkers

| protein.1 | protein.2 | AUC |
|---|---|---|
| LGALS3BP | S100A9 | 0.65 |
| CPN1 | S100A9 | 0.65 |
| PTGDS | VASN | 0.65 |
| MAN1A1 | TNXB | 0.65 |
| CNTN1 | IGFBP3 | 0.65 |
| CPB2 | MASP1 | 0.65 |
| HYOU1 | TNXB | 0.65 |
| CDH5 | COMP | 0.65 |
| CLU | QSOX1 | 0.65 |
| APOA4 | TAGLN2 | 0.65 |
| MASP2 | S100A8 | 0.65 |
| CD163 | SPP2 | 0.65 |
| APOA4 | PFN1 | 0.65 |
| CA1 | CDH5 | 0.65 |
| CLEC3B | IGFBP3 | 0.65 |
| PEPD | PTGDS | 0.65 |
| IGFBP3 | TAGLN2 | 0.65 |
| CD163 | HGFAC | 0.65 |
| APOA1 | VTN | 0.65 |
| QSOX1 | TNXB | 0.65 |
| CD14 | CNTN1 | 0.65 |
| LRG1 | SEPP1 | 0.65 |
| IGFBP3 | QSOX1 | 0.65 |
| APOA4 | IGF2 | 0.65 |
| CA1 | CPN2 | 0.65 |
| CPN1 | MINPP1 | 0.65 |
| CPN1 | IGF2 | 0.65 |
| APOC3 | IGFBP3 | 0.65 |
| CPN2 | PGLYRP2 | 0.65 |
| ATRN | CPN1 | 0.65 |
| CLEC3B | TNXB | 0.65 |
| NCAM1 | PGLYRP2 | 0.65 |
| PGLYRP2 | S100A9 | 0.65 |
| PDLIM1 | PEPD | 0.65 |
| CA2 | CPN2 | 0.65 |
| BCHE | CPN1 | 0.65 |
| HGFAC | THBS1 | 0.65 |
| LRG1 | MAN1A1 | 0.65 |
| PGLYRP2 | SPP2 | 0.65 |
| CPN1 | MST1 | 0.65 |
| CPN1 | GP1BA | 0.65 |
| CPN2 | PCSK9 | 0.65 |
| MINPP1 | S100A8 | 0.65 |
| CDH5 | NID1 | 0.65 |
| CPN2 | NCAM1 | 0.65 |
| GPLD1 | VTN | 0.65 |
| GPLD1 | S100A9 | 0.65 |
| CLEC3B | HYOU1 | 0.65 |
| CA2 | CDH5 | 0.65 |
| CLU | FCN3 | 0.65 |
| CPN2 | FCN3 | 0.65 |
| NID1 | TNXB | 0.65 |
| IGFBP3 | PFN1 | 0.65 |
| GPX3 | MASP1 | 0.65 |
| CDH5 | CNDP1 | 0.65 |
| CD163 | PGLYRP2 | 0.65 |
| LCAT | THBS1 | 0.65 |
| CPN1 | PROS1 | 0.65 |
| LPA | NCAM1 | 0.65 |
| LGALS3BP | PROS1 | 0.65 |
| LCAT | PDLIM1 | 0.65 |
| ATRN | CDH5 | 0.65 |
| GP1BA | VTN | 0.65 |
| CPN1 | NID1 | 0.65 |
| CDH5 | TNXB | 0.65 |
| BCHE | TNXB | 0.65 |
| CLU | NID1 | 0.65 |
| CPN1 | MASP2 | 0.65 |
| CPN1 | SPP2 | 0.65 |
| CPN2 | TGFBI | 0.65 |
| LGALS3BP | MASP1 | 0.65 |
| IGFBP3 | MST1 | 0.65 |
| QSOX1 | NA | 0.65 |
| GP1BA | PROS1 | 0.65 |
| CA2 | CPN1 | 0.65 |
| CNDP1 | TNXB | 0.65 |
| MASP1 | SPP2 | 0.65 |
| PCSK9 | TNXB | 0.65 |
| CPN2 | MASP1 | 0.65 |
| CLU | CPN1 | 0.65 |
| APOC3 | PDLIM1 | 0.65 |
| CPB2 | PGLYRP2 | 0.65 |
| CPN1 | SHBG | 0.65 |
| HGFAC | TNXB | 0.65 |
| PRG4 | S100A9 | 0.65 |
| APOA1 | CD163 | 0.65 |
| CD163 | CPB2 | 0.65 |
| CPN1 | PCSK9 | 0.65 |
| CPN1 | TGFBI | 0.65 |
| APOC3 | CPN1 | 0.65 |
| CA1 | LUM | 0.65 |
| CLU | PRDX2 | 0.65 |
| CDH5 | LUM | 0.65 |
| CD163 | QSOX1 | 0.65 |
| HYOU1 | S100A9 | 0.65 |
| IGFBP3 | VASN | 0.65 |
| APOC3 | CDH5 | 0.65 |
| APOA1 | LUM | 0.65 |
| HGFAC | IGFBP3 | 0.64 |
| CLEC3B | CLU | 0.64 |
| CA2 | S100A9 | 0.64 |
| APOA1 | S100A9 | 0.64 |
| CLU | PROS1 | 0.64 |
| QSOX1 | S100A9 | 0.64 |
| TGFBI | TNXB | 0.64 |
| BTD | CACNA2D1 | 0.64 |
| MAN1A1 | S100A8 | 0.64 |
| CPN2 | QSOX1 | 0.64 |
| CD163 | LUM | 0.64 |
| CD163 | FCN3 | 0.64 |
| ATRN | TNXB | 0.64 |
| FCN3 | NCAM1 | 0.64 |
| MST1 | TNXB | 0.64 |
| CPB2 | CPN1 | 0.64 |
| CPN1 | GP5 | 0.64 |
| MASP1 | VASN | 0.64 |
| CDH5 | GP1BA | 0.64 |
| HYOU1 | MASP1 | 0.64 |
| ATRN | MASP1 | 0.64 |
| LGALS3BP | NCAM1 | 0.64 |
| MINPP1 | VTN | 0.64 |
| CNTN1 | VWF | 0.64 |
| PEPD | VTN | 0.64 |
| CPN1 | VCAM1 | 0.64 |
| APOE | LUM | 0.64 |
| HYOU1 | VTN | 0.64 |
| CD163 | PEPD | 0.64 |
| CA1 | CPN1 | 0.64 |
| CPN2 | HYOU1 | 0.64 |
| IGFBP3 | PEPD | 0.64 |
| CLU | CNDP1 | 0.64 |
| CD163 | PCSK9 | 0.64 |
| MASP1 | PGLYRP2 | 0.64 |
| IGF2 | IGFBP3 | 0.64 |
| MASP1 | MASP2 | 0.64 |
| CPN2 | IGF2 | 0.64 |
| CNDP1 | MASP1 | 0.64 |
| S100A8 | VCAM1 | 0.64 |
| CLU | GP5 | 0.64 |
| CD163 | COMP | 0.64 |
| GP1BA | PGLYRP2 | 0.64 |
| GP1BA | MASP1 | 0.64 |
| CA1 | TNXB | 0.64 |
| APOA1 | COMP | 0.64 |
| HYOU1 | NCAM1 | 0.64 |
| APOE | MASP1 | 0.64 |
| APOC3 | TNXB | 0.64 |
| CDH5 | TGFBI | 0.64 |
| MASP1 | SEPP1 | 0.64 |
| CA2 | NCAM1 | 0.64 |

TABLE 2-continued

Panel Combinations of Two Candidate Latent TB Biomarkers

| protein.1 | protein.2 | AUC |
|---|---|---|
| CD163 | S100A9 | 0.64 |
| CPN1 | HGFAC | 0.64 |
| APOC1 | CLU | 0.64 |
| GPLD1 | TNXB | 0.64 |
| CDH5 | MASP2 | 0.64 |
| CA1 | NCAM1 | 0.64 |
| CA1 | HYOU1 | 0.64 |
| MASP1 | PRDX2 | 0.64 |
| LPA | PROS1 | 0.64 |
| CPN1 | MAN1A1 | 0.64 |
| CD163 | CNTN1 | 0.64 |
| CD163 | PRDX2 | 0.64 |
| CDH5 | CLEC3B | 0.64 |
| MASP1 | TLN1 | 0.64 |
| ATRN | COMP | 0.64 |
| LUM | SPP2 | 0.64 |
| CD163 | GPLD1 | 0.64 |
| CA2 | CLU | 0.64 |
| APOE | CLU | 0.64 |
| SPP2 | TNXB | 0.64 |
| GP5 | THBS1 | 0.64 |
| DBH | IGFBP3 | 0.64 |
| CPN2 | VASN | 0.64 |
| MASP1 | MST1 | 0.64 |
| LGALS3BP | PGLYRP2 | 0.64 |
| CDH5 | SEPP1 | 0.64 |
| CPN1 | TLN1 | 0.64 |
| CPN1 | LCAT | 0.64 |
| APOC1 | IGFBP3 | 0.64 |
| HYOU1 | NID1 | 0.64 |
| PGLYRP2 | PRDX2 | 0.64 |
| APOC1 | NCAM1 | 0.64 |
| CLU | CPN2 | 0.64 |
| APOE | CPN2 | 0.64 |
| LPA | NA | 0.64 |
| CD163 | MINPP1 | 0.64 |
| GPX3 | NCAM1 | 0.64 |
| CDH5 | SHBG | 0.64 |
| CLU | HYOU1 | 0.64 |
| LPA | PRG4 | 0.64 |
| CPN1 | CPN2 | 0.64 |
| GPX3 | PGLYRP2 | 0.64 |
| SHBG | TNXB | 0.64 |
| CPN2 | MASP2 | 0.64 |
| CA1 | CD163 | 0.64 |
| MAN1A1 | MASP1 | 0.64 |
| APOE | S100A9 | 0.64 |
| APOE | PROS1 | 0.64 |
| GP5 | TNXB | 0.64 |
| LGALS3BP | LUM | 0.64 |
| NCAM1 | PRG4 | 0.64 |
| HYOU1 | PGLYRP2 | 0.64 |
| TAGLN2 | THBS1 | 0.64 |
| HYOU1 | PROS1 | 0.64 |
| CPN1 | SEPP1 | 0.64 |
| CD163 | PRG4 | 0.64 |
| CKM | TNXB | 0.64 |
| CPN2 | SPP2 | 0.64 |
| IGF2 | PDLIM1 | 0.64 |
| IGFBP3 | MINPP1 | 0.64 |
| CPB2 | NCAM1 | 0.64 |
| CKM | CLU | 0.64 |
| GPLD1 | NCAM1 | 0.64 |
| CPN1 | GPLD1 | 0.64 |
| CA2 | HYOU1 | 0.64 |
| HGFAC | PDLIM1 | 0.64 |
| NCAM1 | QSOX1 | 0.64 |
| MASP1 | PRG4 | 0.64 |
| CNTN1 | LRG1 | 0.64 |
| IGFBP3 | LCAT | 0.64 |
| PRG4 | PROS1 | 0.64 |
| CDH5 | MST1 | 0.64 |
| CPB2 | LUM | 0.64 |
| LCAT | TNXB | 0.64 |
| APOC1 | CDH5 | 0.64 |
| CPN2 | GP5 | 0.64 |
| BCHE | MASP1 | 0.64 |
| CPB2 | S100A9 | 0.64 |
| APOC1 | CPN2 | 0.64 |
| CA2 | CD163 | 0.64 |
| IGF2 | TNXB | 0.64 |
| CLU | VASN | 0.64 |
| CPN2 | GP1BA | 0.64 |
| ATRN | FCN3 | 0.64 |
| GP5 | MASP1 | 0.64 |
| PCSK9 | S100A9 | 0.64 |
| CDH5 | GP5 | 0.64 |
| ATRN | CPN2 | 0.64 |
| CA1 | S100A9 | 0.64 |
| CD163 | IGF2 | 0.64 |
| ATRN | PGLYRP2 | 0.64 |
| CKM | CPN1 | 0.64 |
| CA1 | CLU | 0.64 |
| APOE | CD163 | 0.64 |
| LCAT | S100A8 | 0.64 |
| APOA1 | NA | 0.64 |
| CDH5 | HGFAC | 0.64 |
| HYOU1 | MASP2 | 0.64 |
| CLU | CPB2 | 0.64 |
| LUM | NCAM1 | 0.64 |
| LUM | TNXB | 0.64 |
| LUM | SEPP1 | 0.64 |
| GP1BA | S100A9 | 0.64 |
| IGF2 | MASP1 | 0.64 |
| MINPP1 | TNXB | 0.64 |
| APOC1 | TNXB | 0.64 |
| ATRN | PRDX2 | 0.64 |
| CPN2 | TLN1 | 0.64 |
| CPN1 | PEPD | 0.64 |
| APOC3 | MASP1 | 0.64 |
| CLU | GP1BA | 0.64 |
| CD163 | LGALS3BP | 0.64 |
| LUM | PCSK9 | 0.64 |
| FCN3 | S100A9 | 0.64 |
| CACNA2D1 | S100A9 | 0.63 |
| CPB2 | NA | 0.63 |
| CDH5 | SPP2 | 0.63 |
| MASP1 | TGFBI | 0.63 |
| CDH5 | MAN1A1 | 0.63 |
| LPA | MAN1A1 | 0.63 |
| CD163 | GP5 | 0.63 |
| CKM | IGFBP3 | 0.63 |
| CLEC3B | MASP1 | 0.63 |
| LPA | PRDX2 | 0.63 |
| CLU | SPP2 | 0.63 |
| CD163 | SEPP1 | 0.63 |
| GP1BA | TNXB | 0.63 |
| LUM | PGLYRP2 | 0.63 |
| CDH5 | DBH | 0.63 |
| CNTN1 | S100A8 | 0.63 |
| COMP | PROS1 | 0.63 |
| APOA1 | PGLYRP2 | 0.63 |
| CA2 | TNXB | 0.63 |
| GP1BA | NCAM1 | 0.63 |
| S100A9 | VASN | 0.63 |
| CPN2 | MST1 | 0.63 |
| CLU | LGALS3BP | 0.63 |
| CLU | GPX3 | 0.63 |
| GPLD1 | PGLYRP2 | 0.63 |
| BCHE | CLU | 0.63 |
| S100A9 | SPP2 | 0.63 |
| PROS1 | QSOX1 | 0.63 |
| CPN1 | DBH | 0.63 |
| TNXB | VASN | 0.63 |
| CLU | PFN1 | 0.63 |
| LUM | NID1 | 0.63 |
| CPN1 | LGALS3BP | 0.63 |
| MASP1 | VCAM1 | 0.63 |

TABLE 2-continued

Panel Combinations of Two Candidate Latent TB Biomarkers

| protein.1 | protein.2 | AUC |
|---|---|---|
| CD163 | CLEC3B | 0.63 |
| CD163 | TGFBI | 0.63 |
| DBH | TNXB | 0.63 |
| CD163 | CNDP1 | 0.63 |
| HGFAC | S100A9 | 0.63 |
| LUM | MAN1A1 | 0.63 |
| CDH5 | MINPP1 | 0.63 |
| APOA1 | MASP1 | 0.63 |
| APOC3 | LUM | 0.63 |
| CPN2 | PROS1 | 0.63 |
| ATRN | CLU | 0.63 |
| CPN1 | PRG4 | 0.63 |
| IGFBP3 | VCAM1 | 0.63 |
| CPN2 | VCAM1 | 0.63 |
| HGFAC | LUM | 0.63 |
| MASP2 | PDLIM1 | 0.63 |
| APOC3 | CLU | 0.63 |
| CLU | PCSK9 | 0.63 |
| FCN3 | PROS1 | 0.63 |
| ATRN | CLEC3B | 0.63 |
| ATRN | NID1 | 0.63 |
| APOC3 | CPN2 | 0.63 |
| CLU | LCAT | 0.63 |
| APOA4 | CNTN1 | 0.63 |
| HYOU1 | LGALS3BP | 0.63 |
| LUM | QSOX1 | 0.63 |
| LPA | NID1 | 0.63 |
| PCSK9 | PGLYRP2 | 0.63 |
| CLU | VCAM1 | 0.63 |
| MASP1 | SHBG | 0.63 |
| CPB2 | CPN2 | 0.63 |
| CPN2 | HGFAC | 0.63 |
| CPB2 | LPA | 0.63 |
| CLU | MASP2 | 0.63 |
| MINPP1 | NA | 0.63 |
| APOC3 | PROS1 | 0.63 |
| BCHE | CPN2 | 0.63 |
| CD163 | MST1 | 0.63 |
| CDH5 | PEPD | 0.63 |
| BCHE | S100A9 | 0.63 |
| CA2 | LUM | 0.63 |
| ATRN | LUM | 0.63 |
| APOC3 | S100A9 | 0.63 |
| MASP1 | MINPP1 | 0.63 |
| CA2 | MASP1 | 0.63 |
| APOA1 | NCAM1 | 0.63 |
| CPN1 | TAGLN2 | 0.63 |
| CD163 | GP1BA | 0.63 |
| LUM | MASP2 | 0.63 |
| CLU | IGF2 | 0.63 |
| TLN1 | TNXB | 0.63 |
| CD163 | NID1 | 0.63 |
| FCN3 | PGLYRP2 | 0.63 |
| PEPD | S100A9 | 0.63 |
| GPLD1 | MASP1 | 0.63 |
| APOA1 | LPA | 0.63 |
| PGLYRP2 | SEPP1 | 0.63 |
| CDH5 | LCAT | 0.63 |
| S100A9 | TGFBI | 0.63 |
| PEPD | TNXB | 0.63 |
| CDH5 | TAGLN2 | 0.63 |
| APOC1 | HYOU1 | 0.63 |
| CD163 | VASN | 0.63 |
| CLU | SEPP1 | 0.63 |
| CNTN1 | VTN | 0.63 |
| BCHE | LUM | 0.63 |
| GPLD1 | LUM | 0.63 |
| S100A9 | TLN1 | 0.63 |
| CPN2 | LGALS3BP | 0.63 |
| GP1BA | LPA | 0.63 |
| APOE | NCAM1 | 0.63 |
| APOA1 | CLU | 0.63 |
| ATRN | LPA | 0.63 |
| CLU | SHBG | 0.63 |
| CDH5 | IGF2 | 0.63 |
| APOE | LPA | 0.63 |
| PDLIM1 | TLN1 | 0.63 |
| CLEC3B | LUM | 0.63 |
| CLEC3B | S100A9 | 0.63 |
| CLEC3B | THBS1 | 0.63 |
| CD163 | MASP2 | 0.63 |
| CKM | S100A9 | 0.63 |
| GPX3 | LPA | 0.63 |
| NID1 | S100A9 | 0.63 |
| HYOU1 | MINPP1 | 0.63 |
| APOC1 | MASP1 | 0.63 |
| TNXB | VCAM1 | 0.63 |
| HYOU1 | LUM | 0.63 |
| CLU | MST1 | 0.63 |
| LUM | MST1 | 0.63 |
| DBH | MASP1 | 0.63 |
| ATRN | HYOU1 | 0.63 |
| CLU | PRG4 | 0.63 |
| CKM | LUM | 0.63 |
| CPN2 | SHBG | 0.63 |
| APOE | HYOU1 | 0.63 |
| CPN2 | MINPP1 | 0.63 |
| BCHE | NCAM1 | 0.63 |
| CD163 | MAN1A1 | 0.63 |
| ATRN | PROS1 | 0.63 |
| PEN1 | TNXB | 0.63 |
| CLU | TGFBI | 0.63 |
| PROS1 | SPP2 | 0.63 |
| CPN1 | PFN1 | 0.63 |
| LUM | TGFBI | 0.63 |
| CPN2 | DBH | 0.63 |
| COMP | MAN1A1 | 0.63 |
| HYOU1 | MST1 | 0.63 |
| APOE | NA | 0.63 |
| ATRN | NCAM1 | 0.63 |
| GP5 | PGLYRP2 | 0.63 |
| CDH5 | PFN1 | 0.63 |
| CPN2 | LCAT | 0.63 |
| CACNA2D1 | VTN | 0.63 |
| LGALS3BP | QSOX1 | 0.63 |
| PRG4 | NA | 0.63 |
| APOC1 | LUM | 0.63 |
| FCN3 | HYOU1 | 0.63 |
| HYOU1 | QSOX1 | 0.63 |
| NCAM1 | SPP2 | 0.63 |
| APOE | ATRN | 0.63 |
| CNDP1 | PGLYRP2 | 0.63 |
| CLEC3B | PDLIM1 | 0.63 |
| CA1 | MASP1 | 0.63 |
| TAGLN2 | TNXB | 0.63 |
| CACNA2D1 | PTGDS | 0.63 |
| CNDP1 | LUM | 0.63 |
| CLU | DBH | 0.63 |
| CACNA2D1 | CPN1 | 0.63 |
| APOC3 | CD163 | 0.63 |
| CLU | GPLD1 | 0.63 |
| MST1 | PDLIM1 | 0.63 |
| CLEC3B | NCAM1 | 0.62 |
| CLU | HGFAC | 0.62 |
| CLU | MAN1A1 | 0.62 |
| PRDX2 | PROS1 | 0.62 |
| GP5 | LUM | 0.62 |
| LCAT | MASP1 | 0.62 |
| APOA4 | CACNA2D1 | 0.62 |
| PGLYRP2 | PRG4 | 0.62 |
| BCHE | HYOU1 | 0.62 |
| HYOU1 | SPP2 | 0.62 |
| APOA1 | CPN1 | 0.62 |
| APOC3 | NCAM1 | 0.62 |
| S100A9 | SEPP1 | 0.62 |
| GPX3 | HYOU1 | 0.62 |
| PDLIM1 | VASN | 0.62 |
| APOA1 | NID1 | 0.62 |
| MST1 | S100A9 | 0.62 |
| CDH5 | TLN1 | 0.62 |

TABLE 2-continued

Panel Combinations of Two Candidate Latent TB Biomarkers

| protein.1 | protein.2 | AUC |
|---|---|---|
| FCN3 | PDLIM1 | 0.62 |
| GP5 | S100A9 | 0.62 |
| HGFAC | MASP1 | 0.62 |
| IGF2 | LUM | 0.62 |
| DBH | LUM | 0.62 |
| BCHE | COMP | 0.62 |
| CKM | MASP1 | 0.62 |
| CLU | MINPP1 | 0.62 |
| GPX3 | S100A9 | 0.62 |
| CNTN1 | TNXB | 0.62 |
| ATRN | PRG4 | 0.62 |
| CLU | PEPD | 0.62 |
| HGFAC | NCAM1 | 0.62 |
| CPN2 | PRG4 | 0.62 |
| MINPP1 | PROS1 | 0.62 |
| NCAM1 | TLN1 | 0.62 |
| GPLD1 | HYOU1 | 0.62 |
| LPA | QSOX1 | 0.62 |
| CPB2 | HYOU1 | 0.62 |
| CDH5 | VCAM1 | 0.62 |
| GP5 | PROS1 | 0.62 |
| PGLYRP2 | SHBG | 0.62 |
| BCHE | NA | 0.62 |
| GPLD1 | PROS1 | 0.62 |
| BCHE | PROS1 | 0.62 |
| GPLD1 | LPA | 0.62 |
| HYOU1 | PCSK9 | 0.62 |
| CPB2 | PROS1 | 0.62 |
| MINPP1 | PRDX2 | 0.62 |
| CDH5 | VASN | 0.62 |
| DBH | S100A9 | 0.62 |
| PDLIM1 | NA | 0.62 |
| LUM | TAGLN2 | 0.62 |
| CDH5 | CKM | 0.62 |
| CD163 | DBH | 0.62 |
| NCAM1 | PCSK9 | 0.62 |
| CNDP1 | S100A9 | 0.62 |
| CD163 | CKM | 0.62 |
| CKM | HYOU1 | 0.62 |
| PFN1 | S100A9 | 0.62 |
| LUM | TLN1 | 0.62 |
| MASP1 | TAGLN2 | 0.62 |
| CPB2 | QSOX1 | 0.62 |
| CPN2 | GPX3 | 0.62 |
| CNTN1 | PTGDS | 0.62 |
| FCN3 | QSOX1 | 0.62 |
| CD163 | TLN1 | 0.62 |
| NCAM1 | SHBG | 0.62 |
| MASP1 | PFN1 | 0.62 |
| GP1BA | LUM | 0.62 |
| IGF2 | S100A9 | 0.62 |
| HGFAC | HYOU1 | 0.62 |
| PROS1 | VCAM1 | 0.62 |
| S100A9 | TAGLN2 | 0.62 |
| CPN2 | GPLD1 | 0.62 |
| MAN1A1 | NA | 0.62 |
| CD163 | LCAT | 0.62 |
| HGFAC | PROS1 | 0.62 |
| MASP2 | NCAM1 | 0.62 |
| CPN2 | PEPD | 0.62 |
| APOA1 | TLN1 | 0.62 |
| APOA1 | PRDX2 | 0.62 |
| IGF2 | NCAM1 | 0.62 |
| APOC3 | HYOU1 | 0.62 |
| MINPP1 | S100A9 | 0.62 |
| APOA1 | PROS1 | 0.62 |
| BCHE | PRDX2 | 0.62 |
| APOC1 | PROS1 | 0.62 |
| CNTN1 | CPN2 | 0.62 |
| CD163 | SHBG | 0.62 |
| BCHE | PGLYRP2 | 0.62 |
| MAN1A1 | PGLYRP2 | 0.62 |
| GPX3 | NA | 0.62 |
| CNTN1 | LGALS3BP | 0.62 |
| MST1 | PGLYRP2 | 0.62 |
| GP5 | PDLIM1 | 0.62 |
| CACNA2D1 | CLU | 0.62 |
| LUM | PFN1 | 0.62 |
| CKM | CPN2 | 0.62 |
| CPN2 | SEPP1 | 0.62 |
| NID1 | PGLYRP2 | 0.62 |
| LPA | VCAM1 | 0.62 |
| PGLYRP2 | QSOX1 | 0.62 |
| PRG4 | VASN | 0.62 |
| PDLIM1 | VCAM1 | 0.62 |
| CNTN1 | PGLYRP2 | 0.62 |
| ATRN | GPX3 | 0.62 |
| PGLYRP2 | VASN | 0.62 |
| NCAM1 | NID1 | 0.62 |
| MASP2 | THBS1 | 0.62 |
| CA2 | PGLYRP2 | 0.62 |
| CPN2 | PFN1 | 0.62 |
| GP5 | LPA | 0.62 |
| LPA | MINPP1 | 0.62 |
| CA1 | LPA | 0.62 |
| APOA1 | APOE | 0.62 |
| COMP | S100A9 | 0.62 |
| LCAT | LUM | 0.62 |
| PCSK9 | PROS1 | 0.62 |
| MAN1A1 | PRDX2 | 0.62 |
| CNDP1 | NCAM1 | 0.62 |
| ATRN | QSOX1 | 0.62 |
| CPN2 | TAGLN2 | 0.62 |
| NID1 | NA | 0.62 |
| MST1 | NCAM1 | 0.62 |
| HYOU1 | SEPP1 | 0.62 |
| APOC3 | ATRN | 0.62 |
| GP1BA | HYOU1 | 0.62 |
| GPX3 | NID1 | 0.62 |
| CPN2 | MAN1A1 | 0.62 |
| NCAM1 | TGFBI | 0.62 |
| MAN1A1 | NCAM1 | 0.62 |
| CD163 | TAGLN2 | 0.62 |
| GP1BA | GPX3 | 0.62 |
| APOC3 | PGLYRP2 | 0.62 |
| CD163 | VCAM1 | 0.62 |
| LGALS3BP | LPA | 0.62 |
| THBS1 | VASN | 0.62 |
| MAN1A1 | PROS1 | 0.62 |
| NCAM1 | PEPD | 0.62 |
| CD163 | PFN1 | 0.62 |
| PRG4 | QSOX1 | 0.62 |
| TGFBI | NA | 0.61 |
| APOA1 | CPN2 | 0.61 |
| FCN3 | LPA | 0.61 |
| DBH | PROS1 | 0.61 |
| HYOU1 | PRG4 | 0.61 |
| PGLYRP2 | TLN1 | 0.61 |
| THBS1 | VCAM1 | 0.61 |
| GP5 | HYOU1 | 0.61 |
| GPLD1 | NID1 | 0.61 |
| APOA1 | HYOU1 | 0.61 |
| CNTN1 | LUM | 0.61 |
| MASP1 | PEPD | 0.61 |
| APOA1 | QSOX1 | 0.61 |
| GP5 | NCAM1 | 0.61 |
| MASP2 | PGLYRP2 | 0.61 |
| LPA | SEPP1 | 0.61 |
| IGF2 | PRG4 | 0.61 |
| CA1 | PGLYRP2 | 0.61 |
| CA2 | MINPP1 | 0.61 |
| CA1 | PROS1 | 0.61 |
| HYOU1 | PEPD | 0.61 |
| CA2 | PROS1 | 0.61 |
| LUM | PEPD | 0.61 |
| IGF2 | THBS1 | 0.61 |
| CNDP1 | HYOU1 | 0.61 |
| S100A9 | SHBG | 0.61 |
| CNDP1 | PROS1 | 0.61 |
| APOA1 | ATRN | 0.61 |

TABLE 2-continued

Panel Combinations of Two Candidate Latent TB Biomarkers

| protein.1 | protein.2 | AUC |
|---|---|---|
| DBH | HYOU1 | 0.61 |
| MINPP1 | NCAM1 | 0.61 |
| APOC1 | S100A9 | 0.61 |
| MASP2 | PROS1 | 0.61 |
| LCAT | PROS1 | 0.61 |
| HYOU1 | MAN1A1 | 0.61 |
| PGLYRP2 | TGFBI | 0.61 |
| APOA1 | FCN3 | 0.61 |
| HYOU1 | TGFBI | 0.61 |
| APOE | PGLYRP2 | 0.61 |
| PROS1 | SEPP1 | 0.61 |
| PGLYRP2 | TAGLN2 | 0.61 |
| LUM | MINPP1 | 0.61 |
| ATRN | CA1 | 0.61 |
| GPX3 | PROS1 | 0.61 |
| COMP | SEPP1 | 0.61 |
| APOC1 | PGLYRP2 | 0.61 |
| ATRN | LGALS3BP | 0.61 |
| CA2 | LPA | 0.61 |
| LPA | MASP2 | 0.61 |
| CACNA2D1 | CD163 | 0.61 |
| DBH | NCAM1 | 0.61 |
| HYOU1 | TLN1 | 0.61 |
| NCAM1 | TAGLN2 | 0.61 |
| NCAM1 | SEPP1 | 0.61 |
| APOE | CPB2 | 0.61 |
| HYOU1 | SHBG | 0.61 |
| CNTN1 | CPN1 | 0.61 |
| NCAM1 | VASN | 0.61 |
| ATRN | CA2 | 0.61 |
| ATRN | MAN1A1 | 0.61 |
| HYOU1 | IGF2 | 0.61 |
| PROS1 | SHBG | 0.61 |
| COMP | QSOX1 | 0.61 |
| ATRN | CPB2 | 0.61 |
| IGF2 | PGLYRP2 | 0.61 |
| LCAT | PGLYRP2 | 0.61 |
| GPX3 | QSOX1 | 0.61 |
| MST1 | PROS1 | 0.61 |
| HYOU1 | VCAM1 | 0.61 |
| ATRN | VCAM1 | 0.61 |
| MASP2 | S100A9 | 0.61 |
| ATRN | TGFBI | 0.61 |
| GPLD1 | NA | 0.61 |
| APOA1 | BCHE | 0.61 |
| PROS1 | TGFBI | 0.61 |
| CPB2 | NID1 | 0.61 |
| PFN1 | PGLYRP2 | 0.61 |
| CLEC3B | PGLYRP2 | 0.61 |
| CKM | NCAM1 | 0.61 |
| LPA | TGFBI | 0.61 |
| LCAT | NCAM1 | 0.61 |
| APOC1 | CD163 | 0.61 |
| NID1 | PRG4 | 0.61 |
| BCHE | FCN3 | 0.61 |
| COMP | PRG4 | 0.61 |
| CPB2 | MINPP1 | 0.61 |
| APOC3 | LPA | 0.61 |
| ATRN | PCSK9 | 0.61 |
| BCHE | LPA | 0.61 |
| PCSK9 | QSOX1 | 0.61 |
| COMP | LPA | 0.61 |
| HGFAC | PGLYRP2 | 0.61 |
| MINPP1 | PGLYRP2 | 0.61 |
| PRDX2 | QSOX1 | 0.61 |
| MAN1A1 | S100A9 | 0.61 |
| GPX3 | LGALS3BP | 0.61 |
| LGALS3BP | VASN | 0.61 |
| CPB2 | FCN3 | 0.61 |
| CLEC3B | PROS1 | 0.61 |
| LCAT | LPA | 0.61 |
| CNDP1 | PRG4 | 0.61 |
| CNTN1 | THBS1 | 0.61 |
| GP1BA | PRG4 | 0.61 |
| LUM | VASN | 0.61 |
| APOA1 | APOC3 | 0.61 |
| PROS1 | TAGLN2 | 0.61 |
| CACNA2D1 | IGFBP3 | 0.61 |
| APOE | PRDX2 | 0.61 |
| LGALS3BP | NA | 0.61 |
| NCAM1 | PFN1 | 0.61 |
| LPA | SHBG | 0.61 |
| APOA1 | VASN | 0.61 |
| ATRN | GP5 | 0.60 |
| ATRN | SPP2 | 0.60 |
| HGFAC | LPA | 0.60 |
| CPB2 | PRDX2 | 0.60 |
| LPA | PCSK9 | 0.60 |
| LPA | SPP2 | 0.60 |
| HYOU1 | VASN | 0.60 |
| LGALS3BP | NID1 | 0.60 |
| PROS1 | VASN | 0.60 |
| DBH | PGLYRP2 | 0.60 |
| APOA1 | CNDP1 | 0.60 |
| PFN1 | PROS1 | 0.60 |
| APOE | GP1BA | 0.60 |
| APOE | SPP2 | 0.60 |
| PDLIM1 | SHBG | 0.60 |
| MAN1A1 | QSOX1 | 0.60 |
| APOA1 | CA2 | 0.60 |
| PROS1 | TLN1 | 0.60 |
| NID1 | QSOX1 | 0.60 |
| APOE | LGALS3BP | 0.60 |
| CACNA2D1 | CDH5 | 0.60 |
| GPLD1 | QSOX1 | 0.60 |
| GPX3 | VASN | 0.60 |
| GPX3 | PRDX2 | 0.60 |
| IGF2 | PROS1 | 0.60 |
| APOA1 | GP1BA | 0.60 |
| IGF2 | LPA | 0.60 |
| LCAT | S100A9 | 0.60 |
| BCHE | CA2 | 0.60 |
| ATRN | VASN | 0.60 |
| BCHE | CPB2 | 0.60 |
| ATRN | CNDP1 | 0.60 |
| ATRN | MINPP1 | 0.60 |
| LGALS3BP | MINPP1 | 0.60 |
| BCHE | LGALS3BP | 0.60 |
| CACNA2D1 | CPN2 | 0.60 |
| MAN1A1 | MST1 | 0.60 |
| CPB2 | GPX3 | 0.60 |
| S100A9 | VCAM1 | 0.60 |
| PRDX2 | TGFBI | 0.60 |
| APOA1 | CLEC3B | 0.60 |
| COMP | MINPP1 | 0.60 |
| ATRN | HGFAC | 0.60 |
| CDH5 | CNTN1 | 0.60 |
| PRG4 | TLN1 | 0.60 |
| APOA1 | HGFAC | 0.60 |
| COMP | CPB2 | 0.60 |
| ATRN | MASP2 | 0.60 |
| NCAM1 | VCAM1 | 0.60 |
| APOA1 | SPP2 | 0.60 |
| PEPD | PROS1 | 0.60 |
| GPX3 | PCSK9 | 0.60 |
| CLU | CNTN1 | 0.60 |
| MINPP1 | PCSK9 | 0.60 |
| CNDP1 | LPA | 0.60 |
| DBH | LPA | 0.60 |
| MINPP1 | PRG4 | 0.60 |
| CKM | PRG4 | 0.60 |
| LPA | VASN | 0.60 |
| LUM | VCAM1 | 0.60 |
| NID1 | SPP2 | 0.60 |
| IGF2 | LGALS3BP | 0.60 |
| ATRN | GPLD1 | 0.60 |
| CKM | PROS1 | 0.60 |
| PGLYRP2 | VCAM1 | 0.60 |
| CA2 | GPX3 | 0.60 |
| CACNA2D1 | TNXB | 0.60 |

TABLE 2-continued

Panel Combinations of Two Candidate Latent TB Biomarkers

| protein.1 | protein.2 | AUC |
|---|---|---|
| NID1 | PEPD | 0.60 |
| APOA1 | PCSK9 | 0.60 |
| ATRN | BCHE | 0.60 |
| MAN1A1 | PCSK9 | 0.60 |
| HYOU1 | PEN1 | 0.60 |
| LPA | TAGLN2 | 0.60 |
| LPA | PEN1 | 0.60 |
| PRDX2 | PRG4 | 0.60 |
| BCHE | NID1 | 0.60 |
| LGALS3BP | MAN1A1 | 0.60 |
| SHBG | THBS1 | 0.60 |
| APOA1 | MINPP1 | 0.60 |
| CA2 | MAN1A1 | 0.60 |
| LPA | PEPD | 0.60 |
| QSOX1 | SEPP1 | 0.60 |
| CA1 | MINPP1 | 0.60 |
| CPB2 | GP1BA | 0.60 |
| GPLD1 | VCAM1 | 0.60 |
| ATRN | SHBG | 0.60 |
| APOE | QSOX1 | 0.60 |
| APOC1 | ATRN | 0.60 |
| APOA1 | PRG4 | 0.60 |
| GP1BA | MAN1A1 | 0.60 |
| LPA | MST1 | 0.60 |
| GP1BA | QSOX1 | 0.60 |
| COMP | TGFBI | 0.60 |
| BCHE | GPX3 | 0.60 |
| CPB2 | VASN | 0.60 |
| BCHE | QSOX1 | 0.60 |
| CACNA2D1 | MASP1 | 0.60 |
| ATRN | MST1 | 0.60 |
| BCHE | GP1BA | 0.60 |
| ATRN | GP1BA | 0.60 |
| APOE | BCHE | 0.60 |
| FCN3 | PRG4 | 0.60 |
| CNDP1 | PDLLVI1 | 0.60 |
| CACNA2D1 | LUM | 0.60 |
| QSOX1 | SPP2 | 0.60 |
| APOA1 | MST1 | 0.59 |
| HGFAC | NID1 | 0.59 |
| APOA1 | APOC1 | 0.59 |
| GP1BA | NA | 0.59 |
| ATRN | SEPP1 | 0.59 |
| HYOU1 | TAGLN2 | 0.59 |
| FCN3 | MAN1A1 | 0.59 |
| ATRN | TLN1 | 0.59 |
| PRDX2 | SEPP1 | 0.59 |
| GP1BA | MINPP1 | 0.59 |
| BCHE | PRG4 | 0.59 |
| CPB2 | LGALS3BP | 0.59 |
| BCHE | MAN1A1 | 0.59 |
| CKM | PGLYRP2 | 0.59 |
| APOA1 | GPX3 | 0.59 |
| THBS1 | NA | 0.59 |
| APOA1 | LGALS3BP | 0.59 |
| PEPD | PGLYRP2 | 0.59 |
| CPB2 | PRG4 | 0.59 |
| HYOU1 | LCAT | 0.59 |
| BCHE | PCSK9 | 0.59 |
| ATRN | IGF2 | 0.59 |
| MINPP1 | NID1 | 0.59 |
| APOA1 | MASP2 | 0.59 |
| BCHE | CA1 | 0.59 |
| APOE | PRG4 | 0.59 |
| LPA | TLN1 | 0.59 |
| GPX3 | MINPP1 | 0.59 |
| APOA1 | CA1 | 0.59 |
| LGALS3BP | PRG4 | 0.59 |
| FCN3 | GPX3 | 0.59 |
| COMP | GPLD1 | 0.59 |
| APOA1 | IGF2 | 0.59 |
| APOA1 | VCAM1 | 0.59 |
| APOE | MINPP1 | 0.59 |
| NID1 | TGFBI | 0.59 |
| APOA1 | SHBG | 0.59 |
| APOE | GPX3 | 0.59 |
| APOA1 | GP5 | 0.59 |
| CA1 | MAN1A1 | 0.59 |
| APOC1 | BCHE | 0.59 |
| MAN1A1 | NID1 | 0.59 |
| CLEC3B | LPA | 0.59 |
| APOE | COMP | 0.59 |
| MST1 | QSOX1 | 0.59 |
| GP1BA | SEPP1 | 0.59 |
| PCSK9 | PRG4 | 0.59 |
| CKM | LPA | 0.59 |
| FCN3 | MINPP1 | 0.59 |
| APOE | GPLD1 | 0.59 |
| GPX3 | VCAM1 | 0.59 |
| MINPP1 | SPP2 | 0.59 |
| APOE | NID1 | 0.59 |
| APOE | PCSK9 | 0.59 |
| CNDP1 | MAN1A1 | 0.59 |
| CNDP1 | GPX3 | 0.59 |
| ATRN | CKM | 0.59 |
| CPB2 | MAN1A1 | 0.59 |
| FCN3 | GPLD1 | 0.59 |
| GPLD1 | PRG4 | 0.59 |
| APOE | VASN | 0.59 |
| APOA1 | MAN1A1 | 0.59 |
| GPX3 | PRG4 | 0.59 |
| GP1BA | GPLD1 | 0.59 |
| GP1BA | NID1 | 0.59 |
| PRG4 | SPP2 | 0.59 |
| LGALS3BP | TGFBI | 0.59 |
| CPB2 | SHBG | 0.59 |
| CA1 | CPB2 | 0.59 |
| GPLD1 | MAN1A1 | 0.59 |
| GPLD1 | VASN | 0.59 |
| GPLD1 | LGALS3BP | 0.59 |
| PCSK9 | PDLIM1 | 0.59 |
| GP1BA | TGFBI | 0.59 |
| ATRN | PEN1 | 0.59 |
| GPLD1 | PCSK9 | 0.59 |
| APOE | MAN1A1 | 0.59 |
| CPB2 | GPLD1 | 0.59 |
| SEPP1 | NA | 0.59 |
| NID1 | SEPP1 | 0.59 |
| PEPD | PRDX2 | 0.59 |
| ATRN | TAGLN2 | 0.59 |
| APOA1 | TGFBI | 0.59 |
| GPX3 | MAN1A1 | 0.59 |
| CNTN1 | PRG4 | 0.59 |
| BCHE | MINPP1 | 0.59 |
| CACNA2D1 | PROS1 | 0.59 |
| CA2 | TGFBI | 0.59 |
| SPP2 | VASN | 0.59 |
| PDLIM1 | PRDX2 | 0.59 |
| ATRN | LCAT | 0.59 |
| GPLD1 | GPX3 | 0.59 |
| APOE | CA1 | 0.59 |
| NID1 | PRDX2 | 0.59 |
| FCN3 | NID1 | 0.59 |
| APOA1 | CPB2 | 0.59 |
| MINPP1 | QSOX1 | 0.59 |
| APOA1 | CKM | 0.59 |
| GPX3 | MST1 | 0.59 |
| CNTN1 | S100A9 | 0.59 |
| COMP | GPX3 | 0.59 |
| ATRN | PEPD | 0.59 |
| BCHE | SEPP1 | 0.59 |
| CACNA2D1 | PGLYRP2 | 0.59 |
| APOE | FCN3 | 0.59 |
| CA1 | PDLIM1 | 0.59 |
| NID1 | PCSK9 | 0.59 |
| GPX3 | SPP2 | 0.59 |
| ATRN | DBH | 0.59 |
| PDLIM1 | THBS1 | 0.59 |
| APOC3 | CPB2 | 0.59 |
| APOA1 | TAGLN2 | 0.58 |

TABLE 2-continued

Panel Combinations of Two Candidate Latent TB Biomarkers

| protein.1 | protein.2 | AUC |
|---|---|---|
| APOC1 | GPX3 | 0.58 |
| CPB2 | MST1 | 0.58 |
| APOE | TGFBI | 0.58 |
| MAN1A1 | SPP2 | 0.58 |
| MAN1A1 | MINPP1 | 0.58 |
| CA1 | TGFBI | 0.58 |
| GP1BA | LGALS3BP | 0.58 |
| CA1 | GPX3 | 0.58 |
| APOC1 | MINPP1 | 0.58 |
| CA2 | QSOX1 | 0.58 |
| CA1 | NID1 | 0.58 |
| APOA1 | DBH | 0.58 |
| APOA1 | SEPP1 | 0.58 |
| APOA1 | LCAT | 0.58 |
| CNTN1 | HYOU1 | 0.58 |
| APOA1 | PFN1 | 0.58 |
| CNDP1 | CPB2 | 0.58 |
| LGALS3BP | SPP2 | 0.58 |
| CPB2 | HGFAC | 0.58 |
| APOC3 | LGALS3BP | 0.58 |
| CA2 | CPB2 | 0.58 |
| BCHE | TGFBI | 0.58 |
| CA1 | QSOX1 | 0.58 |
| FCN3 | THBS1 | 0.58 |
| CNDP1 | MINPP1 | 0.58 |
| MAN1A1 | PRG4 | 0.58 |
| IGF2 | MAN1A1 | 0.58 |
| CLEC3B | GPX3 | 0.58 |
| CPB2 | SPP2 | 0.58 |
| APOE | CA2 | 0.58 |
| PCSK9 | TGFBI | 0.58 |
| CPB2 | VCAM1 | 0.58 |
| QSOX1 | TGFBI | 0.58 |
| BCHE | GPLD1 | 0.58 |
| APOC1 | PDLIM1 | 0.58 |
| APOC3 | PRG4 | 0.58 |
| FCN3 | GP1BA | 0.58 |
| BCHE | CNDP1 | 0.58 |
| CPB2 | IGF2 | 0.58 |
| CACNA2D1 | NCAM1 | 0.58 |
| CNDP1 | QSOX1 | 0.58 |
| BCHE | SPP2 | 0.58 |
| DBH | PDLIM1 | 0.58 |
| CA2 | PDLIM1 | 0.58 |
| MINPP1 | VASN | 0.58 |
| CKM | LGALS3BP | 0.58 |
| BCHE | VCAM1 | 0.58 |
| CPB2 | MASP2 | 0.58 |
| CLEC3B | CPB2 | 0.58 |
| GPX3 | IGF2 | 0.58 |
| CPB2 | TLN1 | 0.58 |
| MINPP1 | MST1 | 0.58 |
| CPB2 | TGFBI | 0.58 |
| HGFAC | QSOX1 | 0.58 |
| APOA1 | GPLD1 | 0.58 |
| MST1 | THBS1 | 0.58 |
| APOA1 | PEPD | 0.58 |
| LGALS3BP | SEPP1 | 0.58 |
| MINPP1 | SEPP1 | 0.58 |
| PRG4 | SEPP1 | 0.58 |
| GP1BA | PEPD | 0.58 |
| GPLD1 | MINPP1 | 0.58 |
| FCN3 | TGFBI | 0.58 |
| DBH | MAN1A1 | 0.58 |
| MAN1A1 | VASN | 0.58 |
| GPLD1 | SEPP1 | 0.58 |
| MST1 | PRG4 | 0.58 |
| BCHE | CLEC3B | 0.58 |
| GP1BA | HGFAC | 0.58 |
| CA2 | NID1 | 0.58 |
| COMP | PEPD | 0.58 |
| CLEC3B | MINPP1 | 0.58 |
| APOC1 | CPB2 | 0.58 |
| GP5 | PRG4 | 0.58 |
| MINPP1 | TLN1 | 0.58 |
| HGFAC | PRG4 | 0.58 |
| CA2 | PRG4 | 0.58 |
| MASP2 | QSOX1 | 0.58 |
| CLEC3B | NID1 | 0.58 |
| BCHE | MST1 | 0.58 |
| CLEC3B | MAN1A1 | 0.58 |
| PRG4 | VCAM1 | 0.58 |
| APOE | SEPP1 | 0.58 |
| CPB2 | PCSK9 | 0.58 |
| GP5 | MINPP1 | 0.58 |
| COMP | GP1BA | 0.58 |
| CNTN1 | LPA | 0.58 |
| GP5 | GPX3 | 0.58 |
| PRG4 | TGFBI | 0.58 |
| GPLD1 | LCAT | 0.58 |
| BCHE | GP5 | 0.58 |
| APOC3 | MAN1A1 | 0.58 |
| FCN3 | SEPP1 | 0.58 |
| BCHE | TLN1 | 0.58 |
| CNDP1 | TGFBI | 0.58 |
| CNTN1 | NCAM1 | 0.58 |
| HGFAC | MINPP1 | 0.58 |
| GPX3 | HGFAC | 0.58 |
| SPP2 | TGFBI | 0.58 |
| HGFAC | LGALS3BP | 0.58 |
| ATRN | CNTN1 | 0.58 |
| QSOX1 | VASN | 0.58 |
| PEPD | QSOX1 | 0.57 |
| LGALS3BP | PEPD | 0.57 |
| GPLD1 | SPP2 | 0.57 |
| CACNA2D1 | HYOU1 | 0.57 |
| HGFAC | MAN1A1 | 0.57 |
| MST1 | NID1 | 0.57 |
| PEPD | NA | 0.57 |
| SEPP1 | VASN | 0.57 |
| APOE | CNDP1 | 0.57 |
| BCHE | VASN | 0.57 |
| GPX3 | SEPP1 | 0.57 |
| CKM | QSOX1 | 0.57 |
| MASP2 | MINPP1 | 0.57 |
| NID1 | VASN | 0.57 |
| GPX3 | PEPD | 0.57 |
| CLEC3B | PRG4 | 0.57 |
| LCAT | PRDX2 | 0.57 |
| SPP2 | NA | 0.57 |
| APOC3 | GPX3 | 0.57 |
| HGFAC | TGFBI | 0.57 |
| GP5 | MAN1A1 | 0.57 |
| PRG4 | SHBG | 0.57 |
| GP1BA | VASN | 0.57 |
| APOC3 | BCHE | 0.57 |
| CPB2 | PEPD | 0.57 |
| CKM | PDLIM1 | 0.57 |
| DBH | PRG4 | 0.57 |
| CKM | MAN1A1 | 0.57 |
| MINPP1 | TGFBI | 0.57 |
| GP5 | NID1 | 0.57 |
| BCHE | HGFAC | 0.57 |
| IGF2 | NID1 | 0.57 |
| DBH | GPX3 | 0.57 |
| CPB2 | GP5 | 0.57 |
| LGALS3BP | PRDX2 | 0.57 |
| GPX3 | TLN1 | 0.57 |
| CA2 | SEPP1 | 0.57 |
| CNTN1 | PROS1 | 0.57 |
| COMP | PDLIM1 | 0.57 |
| VASN | NA | 0.57 |
| CLEC3B | TGFBI | 0.57 |
| MAN1A1 | SEPP1 | 0.57 |
| FCN3 | LGALS3BP | 0.57 |
| LCAT | NA | 0.57 |
| CPB2 | SEPP1 | 0.57 |
| APOC1 | LPA | 0.57 |
| BCHE | PEPD | 0.57 |
| GP1BA | MST1 | 0.57 |

TABLE 2-continued

Panel Combinations of Two Candidate Latent TB Biomarkers

| protein.1 | protein.2 | AUC |
|---|---|---|
| APOC3 | QSOX1 | 0.57 |
| APOC3 | MINPP1 | 0.57 |
| GPLD1 | SHBG | 0.57 |
| GPLD1 | TLN1 | 0.57 |
| LGALS3BP | VCAM1 | 0.57 |
| CKM | CPB2 | 0.57 |
| APOC1 | MAN1A1 | 0.57 |
| MAN1A1 | SHBG | 0.57 |
| CNTN1 | GPLD1 | 0.57 |
| GPLD1 | MST1 | 0.57 |
| GPLD1 | PRDX2 | 0.57 |
| PEPD | PRG4 | 0.57 |
| MAN1A1 | TLN1 | 0.57 |
| BCHE | MASP2 | 0.57 |
| MAN1A1 | MASP2 | 0.57 |
| DBH | TGFBI | 0.57 |
| APOE | TLN1 | 0.57 |
| CLEC3B | LGALS3BP | 0.57 |
| QSOX1 | SHBG | 0.57 |
| LGALS3BP | PCSK9 | 0.57 |
| GPX3 | LCAT | 0.57 |
| LCAT | PRG4 | 0.57 |
| GPLD1 | TGFBI | 0.57 |
| GP1BA | LCAT | 0.57 |
| MST1 | TGFBI | 0.57 |
| LCAT | LGALS3BP | 0.57 |
| APOC3 | NA | 0.57 |
| CA1 | PRG4 | 0.57 |
| CPB2 | TAGLN2 | 0.57 |
| LCAT | QSOX1 | 0.57 |
| CLEC3B | GPLD1 | 0.57 |
| APOC3 | NID1 | 0.57 |
| APOE | MST1 | 0.57 |
| CKM | MINPP1 | 0.57 |
| GPX3 | SHBG | 0.57 |
| CKM | GPLD1 | 0.57 |
| MAN1A1 | PEPD | 0.57 |
| PRG4 | TAGLN2 | 0.57 |
| APOE | VCAM1 | 0.57 |
| CNDP1 | NID1 | 0.57 |
| CACNA2D1 | CPB2 | 0.57 |
| CACNA2D1 | THBS1 | 0.57 |
| MINPP1 | PEPD | 0.57 |
| APOE | GP5 | 0.57 |
| CNDP1 | THBS1 | 0.57 |
| NID1 | TAGLN2 | 0.57 |
| BCHE | SHBG | 0.57 |
| QSOX1 | TLN1 | 0.57 |
| CNDP1 | GPLD1 | 0.57 |
| LCAT | MINPP1 | 0.57 |
| GP1BA | GP5 | 0.57 |
| CPB2 | PFN1 | 0.57 |
| APOA1 | CNTN1 | 0.57 |
| CA1 | SEPP1 | 0.57 |
| QSOX1 | VCAM1 | 0.57 |
| CACNA2D1 | NID1 | 0.57 |
| APOE | PEPD | 0.57 |
| BCHE | DBH | 0.57 |
| GP5 | QSOX1 | 0.57 |
| DBH | QSOX1 | 0.57 |
| FCN3 | PEPD | 0.57 |
| PFN1 | PRG4 | 0.57 |
| CNTN1 | PDLIM1 | 0.57 |
| GPX3 | MASP2 | 0.57 |
| MINPP1 | PFN1 | 0.57 |
| COMP | LCAT | 0.57 |
| PEPD | VCAM1 | 0.57 |
| CA2 | PEPD | 0.57 |
| GP5 | GPLD1 | 0.57 |
| MASP2 | PRG4 | 0.57 |
| TGFBI | VASN | 0.57 |
| CLEC3B | QSOX1 | 0.57 |
| GP1BA | VCAM1 | 0.57 |
| BCHE | CKM | 0.57 |
| COMP | VASN | 0.57 |
| GPX3 | TAGLN2 | 0.57 |
| GP1BA | SPP2 | 0.57 |
| CPB2 | LCAT | 0.57 |
| APOE | HGFAC | 0.57 |
| APOC3 | GP1BA | 0.56 |
| GP5 | TGFBI | 0.56 |
| MINPP1 | TAGLN2 | 0.56 |
| APOE | MASP2 | 0.56 |
| MINPP1 | SHBG | 0.56 |
| PCSK9 | SEPP1 | 0.56 |
| THBS1 | TLN1 | 0.56 |
| CLEC3B | SEPP1 | 0.56 |
| GP1BA | TLN1 | 0.56 |
| DBH | MINPP1 | 0.56 |
| MASP2 | NID1 | 0.56 |
| APOE | CNTN1 | 0.56 |
| COMP | NID1 | 0.56 |
| LGALS3BP | SHBG | 0.56 |
| CPB2 | DBH | 0.56 |
| GP1BA | PRDX2 | 0.56 |
| GPLD1 | HGFAC | 0.56 |
| CKM | GPX3 | 0.56 |
| LCAT | MAN1A1 | 0.56 |
| GPLD1 | TAGLN2 | 0.56 |
| BCHE | IGF2 | 0.56 |
| GP1BA | PCSK9 | 0.56 |
| HGFAC | PRDX2 | 0.56 |
| GP1BA | IGF2 | 0.56 |
| CNDP1 | SEPP1 | 0.56 |
| CLEC3B | PEPD | 0.56 |
| CNTN1 | CPB2 | 0.56 |
| CNTN1 | QSOX1 | 0.56 |
| GPX3 | TGFBI | 0.56 |
| APOC3 | SEPP1 | 0.56 |
| APOA1 | CACNA2D1 | 0.56 |
| PCSK9 | THBS1 | 0.56 |
| CLEC3B | GP1BA | 0.56 |
| CACNA2D1 | PDLIM1 | 0.56 |
| APOC3 | TGFBI | 0.56 |
| GPX3 | PFN1 | 0.56 |
| IGF2 | MINPP1 | 0.56 |
| APOC1 | QSOX1 | 0.56 |
| CKM | GP1BA | 0.56 |
| NID1 | PFN1 | 0.56 |
| LCAT | NID1 | 0.56 |
| BCHE | LCAT | 0.56 |
| MAN1A1 | TGFBI | 0.56 |
| CKM | THBS1 | 0.56 |
| CA1 | PEPD | 0.56 |
| APOE | DBH | 0.56 |
| APOC3 | SPP2 | 0.56 |
| APOE | LCAT | 0.56 |
| NID1 | TLN1 | 0.56 |
| CA2 | GPLD1 | 0.56 |
| PFN1 | QSOX1 | 0.56 |
| CNTN1 | NID1 | 0.56 |
| GPLD1 | MASP2 | 0.56 |
| QSOX1 | TAGLN2 | 0.56 |
| GPLD1 | IGF2 | 0.56 |
| LGALS3BP | TLN1 | 0.56 |
| MST1 | SEPP1 | 0.56 |
| BCHE | TAGLN2 | 0.56 |
| SPP2 | VCAM1 | 0.56 |
| LGALS3BP | TAGLN2 | 0.56 |
| APOE | SHBG | 0.56 |
| GP5 | LGALS3BP | 0.56 |
| NID1 | SHBG | 0.56 |
| APOE | CLEC3B | 0.56 |
| GP1BA | MASP2 | 0.56 |
| CA2 | LGALS3BP | 0.56 |
| MAN1A1 | VCAM1 | 0.56 |
| SEPP1 | TGFBI | 0.56 |
| APOC3 | APOE | 0.56 |
| GPLD1 | PEPD | 0.56 |
| CNDP1 | LGALS3BP | 0.56 |

TABLE 2-continued

Panel Combinations of Two Candidate Latent TB Biomarkers

| protein.1 | protein.2 | AUC |
| --- | --- | --- |
| PCSK9 | PEPD | 0.56 |
| APOC3 | GPLD1 | 0.56 |
| SEPP1 | SPP2 | 0.56 |
| MINPP1 | VCAM1 | 0.56 |
| APOC1 | GPLD1 | 0.56 |
| TGFBI | VCAM1 | 0.56 |
| PEPD | VASN | 0.56 |
| APOC1 | THBS1 | 0.56 |
| CA1 | LGALS3BP | 0.56 |
| GPLD1 | PFN1 | 0.56 |
| ATRN | CACNA2D1 | 0.56 |
| APOE | IGF2 | 0.56 |
| MAN1A1 | TAGLN2 | 0.56 |
| SEPP1 | TLN1 | 0.56 |
| CKM | NID1 | 0.56 |
| GP5 | SEPP1 | 0.56 |
| APOC3 | VASN | 0.56 |
| PEPD | TGFBI | 0.56 |
| FCN3 | VASN | 0.56 |
| HGFAC | NA | 0.56 |
| APOE | CKM | 0.56 |
| TGFBI | TLN1 | 0.56 |
| IGF2 | SEPP1 | 0.56 |
| APOC1 | LGALS3BP | 0.56 |
| SHBG | TGFBI | 0.56 |
| IGF2 | QSOX1 | 0.55 |
| BCHE | PFN1 | 0.55 |
| CNTN1 | GPX3 | 0.55 |
| IGF2 | TGFBI | 0.55 |
| PEPD | SEPP1 | 0.55 |
| PRDX2 | SPP2 | 0.55 |
| GP1BA | TAGLN2 | 0.55 |
| SHBG | VASN | 0.55 |
| MAN1A1 | PFN1 | 0.55 |
| CKM | TGFBI | 0.55 |
| HGFAC | VASN | 0.55 |
| DBH | GPLD1 | 0.55 |
| DBH | NID1 | 0.55 |
| LGALS3BP | PFN1 | 0.55 |
| SEPP1 | VCAM1 | 0.55 |
| LGALS3BP | MST1 | 0.55 |
| VCAM1 | NA | 0.55 |
| APOC1 | PRG4 | 0.55 |
| PRDX2 | VCAM1 | 0.55 |
| CA2 | GP1BA | 0.55 |
| CA2 | THBS1 | 0.55 |
| PEPD | SPP2 | 0.55 |
| HGFAC | SEPP1 | 0.55 |
| DBH | GP1BA | 0.55 |
| MASP2 | TGFBI | 0.55 |
| HGFAC | SPP2 | 0.55 |
| CA1 | GP1BA | 0.55 |
| APOC1 | APOE | 0.55 |
| MST1 | SPP2 | 0.55 |
| LGALS3BP | MASP2 | 0.55 |
| LCAT | VASN | 0.55 |
| GP1BA | PFN1 | 0.55 |
| PEPD | TLN1 | 0.55 |
| CACNA2D1 | GPX3 | 0.55 |
| TAGLN2 | TGFBI | 0.55 |
| PFN1 | TGFBI | 0.55 |
| CNDP1 | LCAT | 0.55 |
| HGFAC | VCAM1 | 0.55 |
| PRDX2 | THBS1 | 0.55 |
| CACNA2D1 | MAN1A1 | 0.55 |
| CA1 | GPLD1 | 0.55 |
| APOC1 | TGFBI | 0.55 |
| DBH | LGALS3BP | 0.55 |
| LCAT | TGFBI | 0.55 |
| FCN3 | LCAT | 0.55 |
| NID1 | VCAM1 | 0.55 |
| DBH | SEPP1 | 0.55 |
| COMP | LGALS3BP | 0.55 |
| COMP | VCAM1 | 0.55 |
| PRDX2 | VASN | 0.55 |
| CA2 | LCAT | 0.55 |
| CACNA2D1 | LPA | 0.55 |
| CKM | SEPP1 | 0.55 |
| APOC1 | GP1BA | 0.55 |
| CNTN1 | GP1BA | 0.54 |
| CNDP1 | PEPD | 0.54 |
| APOE | PFN1 | 0.54 |
| FCN3 | SPP2 | 0.54 |
| GP1BA | SHBG | 0.54 |
| CACNA2D1 | PRG4 | 0.54 |
| HGFAC | PEPD | 0.54 |
| APOC1 | SEPP1 | 0.54 |
| APOE | TAGLN2 | 0.54 |
| LCAT | PCSK9 | 0.54 |
| GP5 | VASN | 0.54 |
| BCHE | CNTN1 | 0.54 |
| CNTN1 | MAN1A1 | 0.54 |
| MASP2 | PEPD | 0.54 |
| LCAT | SPP2 | 0.54 |
| APOC3 | PEPD | 0.54 |
| CA2 | HGFAC | 0.54 |
| CA1 | THBS1 | 0.54 |
| PCSK9 | VASN | 0.54 |
| CA1 | LCAT | 0.54 |
| LCAT | MST1 | 0.54 |
| IGF2 | SPP2 | 0.54 |
| CNDP1 | GP1BA | 0.54 |
| LCAT | SEPP1 | 0.54 |
| GP5 | PEPD | 0.54 |
| CLEC3B | VCAM1 | 0.54 |
| APOC3 | FCN3 | 0.54 |
| MASP2 | VASN | 0.54 |
| FCN3 | HGFAC | 0.54 |
| APOC1 | NID1 | 0.54 |
| MASP2 | SPP2 | 0.54 |
| CNTN1 | TGFBI | 0.54 |
| CA1 | HGFAC | 0.54 |
| CACNA2D1 | MINPP1 | 0.54 |
| APOC1 | PEPD | 0.54 |
| MST1 | PEPD | 0.54 |
| SEPP1 | SHBG | 0.54 |
| MASP2 | SEPP1 | 0.54 |
| HGFAC | IGF2 | 0.54 |
| PCSK9 | VCAM1 | 0.54 |
| CKM | PEPD | 0.54 |
| IGF2 | VASN | 0.54 |
| APOC3 | VCAM1 | 0.54 |
| APOC3 | PRDX2 | 0.54 |
| MST1 | NA | 0.54 |
| CNTN1 | MINPP1 | 0.54 |
| LCAT | TAGLN2 | 0.54 |
| SEPP1 | TAGLN2 | 0.54 |
| CACNA2D1 | QSOX1 | 0.54 |
| DBH | THBS1 | 0.54 |
| HGFAC | LCAT | 0.54 |
| HGFAC | PCSK9 | 0.54 |
| BCHE | CACNA2D1 | 0.54 |
| LCAT | PEPD | 0.54 |
| IGF2 | LCAT | 0.54 |
| PFN1 | SEPP1 | 0.54 |
| TAGLN2 | VASN | 0.54 |
| APOC3 | LCAT | 0.54 |
| MST1 | VASN | 0.54 |
| PEPD | TAGLN2 | 0.53 |
| COMP | MST1 | 0.53 |
| GP5 | LCAT | 0.53 |
| FCN3 | MST1 | 0.53 |
| CKM | LCAT | 0.53 |
| PEPD | PFN1 | 0.53 |
| CA2 | VCAM1 | 0.53 |
| CACNA2D1 | SEPP1 | 0.53 |
| APOE | CACNA2D1 | 0.53 |
| COMP | SPP2 | 0.53 |
| APOC3 | MST1 | 0.53 |
| APOC3 | COMP | 0.53 |

TABLE 2-continued

Panel Combinations of Two Candidate Latent TB Biomarkers

| protein.1 | protein.2 | AUC |
|---|---|---|
| CNTN1 | VCAM1 | 0.53 |
| APOC1 | VASN | 0.53 |
| CA1 | VASN | 0.53 |
| CA1 | VCAM1 | 0.53 |
| FCN3 | VCAM1 | 0.53 |
| CLEC3B | VASN | 0.53 |
| DBH | PEPD | 0.53 |
| CNTN1 | SEPP1 | 0.53 |
| APOC3 | CA1 | 0.53 |
| MST1 | VCAM1 | 0.53 |
| PFN1 | VASN | 0.53 |
| CNDP1 | VASN | 0.53 |
| APOC3 | HGFAC | 0.53 |
| IGF2 | PEPD | 0.53 |
| CLEC3B | LCAT | 0.53 |
| CNTN1 | PRDX2 | 0.53 |
| PEPD | SHBG | 0.53 |
| DBH | LCAT | 0.53 |
| COMP | THBS1 | 0.53 |
| LCAT | VCAM1 | 0.53 |
| CACNA2D1 | LGALS3BP | 0.53 |
| LCAT | TLN1 | 0.53 |
| DBH | VASN | 0.53 |
| TAGLN2 | VCAM1 | 0.53 |
| CNTN1 | VASN | 0.53 |
| LCAT | MASP2 | 0.53 |
| CA2 | SPP2 | 0.53 |
| SPP2 | TAGLN2 | 0.53 |
| CNTN1 | PEPD | 0.53 |
| VASN | VCAM1 | 0.52 |
| APOC3 | PCSK9 | 0.52 |
| MST1 | PRDX2 | 0.52 |
| CLEC3B | FCN3 | 0.52 |
| APOC3 | CNTN1 | 0.52 |
| GP5 | HGFAC | 0.52 |
| LCAT | PFN1 | 0.52 |
| HGFAC | MASP2 | 0.52 |
| CA2 | VASN | 0.52 |
| IGF2 | VCAM1 | 0.52 |
| CNDP1 | SPP2 | 0.52 |
| TAGLN2 | TLN1 | 0.52 |
| CACNA2D1 | VCAM1 | 0.52 |
| PCSK9 | SPP2 | 0.52 |
| TLN1 | VASN | 0.52 |
| HGFAC | MST1 | 0.52 |
| APOC1 | SPP2 | 0.52 |
| CKM | SPP2 | 0.52 |
| CKM | VASN | 0.52 |
| CACNA2D1 | GPLD1 | 0.52 |
| PFN1 | SPP2 | 0.52 |
| CA1 | SPP2 | 0.52 |
| GP5 | VCAM1 | 0.52 |
| SPP2 | TLN1 | 0.52 |
| CLEC3B | MST1 | 0.52 |
| GP5 | SPP2 | 0.52 |
| CNDP1 | HGFAC | 0.52 |
| CACNA2D1 | TGFBI | 0.52 |
| CA1 | CNTN1 | 0.52 |
| APOC3 | MASP2 | 0.52 |
| CLEC3B | NA | 0.52 |
| MASP2 | VCAM1 | 0.52 |
| CLEC3B | COMP | 0.52 |
| CLEC3B | SPP2 | 0.52 |
| CLEC3B | HGFAC | 0.52 |
| CLEC3B | PRDX2 | 0.52 |
| APOC3 | CA2 | 0.52 |
| CNTN1 | NA | 0.52 |
| PFN1 | VCAM1 | 0.52 |
| COMP | MASP2 | 0.52 |
| CNTN1 | LCAT | 0.52 |
| MASP2 | NA | 0.51 |
| CLEC3B | MASP2 | 0.51 |
| CKM | VCAM1 | 0.51 |
| MST1 | PCSK9 | 0.51 |
| APOC3 | CLEC3B | 0.51 |
| LCAT | SHBG | 0.51 |
| CNTN1 | HGFAC | 0.51 |
| CNTN1 | SPP2 | 0.51 |
| APOC1 | HGFAC | 0.51 |
| SHBG | SPP2 | 0.51 |
| CKM | MASP2 | 0.51 |
| HGFAC | SHBG | 0.51 |
| APOC3 | TLN1 | 0.51 |
| CNTN1 | TAGLN2 | 0.51 |
| APOC3 | IGF2 | 0.51 |
| APOC3 | CKM | 0.51 |
| CNTN1 | FCN3 | 0.51 |
| PFN1 | TLN1 | 0.51 |
| CKM | FCN3 | 0.51 |
| CNDP1 | VCAM1 | 0.51 |
| SHBG | VCAM1 | 0.51 |
| APOC3 | GP5 | 0.51 |
| IGF2 | MST1 | 0.51 |
| DBH | SPP2 | 0.51 |
| CKM | MST1 | 0.51 |
| CNTN1 | MST1 | 0.51 |
| GP5 | MST1 | 0.51 |
| APOC1 | LCAT | 0.51 |
| CACNA2D1 | GP1BA | 0.51 |
| HGFAC | TAGLN2 | 0.50 |
| CKM | HGFAC | 0.50 |
| TLN1 | VCAM1 | 0.50 |
| APOC3 | DBH | 0.50 |
| DBH | VCAM1 | 0.50 |
| CA2 | CNTN1 | 0.50 |
| APOC3 | CNDP1 | 0.50 |
| HGFAC | TLN1 | 0.50 |
| COMP | HGFAC | 0.50 |
| CKM | PRDX2 | 0.50 |
| CNTN1 | PCSK9 | 0.50 |
| APOC3 | TAGLN2 | 0.50 |
| DBH | HGFAC | 0.50 |
| HGFAC | PFN1 | 0.50 |
| APOC3 | SHBG | 0.50 |
| CNTN1 | IGF2 | 0.50 |
| APOC1 | APOC3 | 0.50 |
| MASP2 | PRDX2 | 0.50 |
| CNTN1 | MASP2 | 0.50 |
| CNTN1 | PFN1 | 0.50 |
| APOC3 | PFN1 | 0.50 |
| CA1 | MST1 | 0.50 |
| APOC1 | VCAM1 | 0.50 |
| CACNA2D1 | VASN | 0.50 |
| CA2 | MST1 | 0.50 |
| CLEC3B | PCSK9 | 0.50 |
| IGF2 | NA | 0.49 |
| CACNA2D1 | PEPD | 0.49 |
| CNDP1 | CNTN1 | 0.49 |
| MST1 | SHBG | 0.49 |
| FCN3 | MASP2 | 0.49 |
| DBH | MST1 | 0.49 |
| CACNA2D1 | LCAT | 0.49 |
| CNTN1 | GP5 | 0.49 |
| MASP2 | MST1 | 0.49 |
| APOC1 | CNTN1 | 0.49 |
| CKM | NA | 0.49 |
| CNDP1 | MST1 | 0.49 |
| TAGLN2 | NA | 0.49 |
| PFN1 | NA | 0.49 |
| IGF2 | MASP2 | 0.49 |
| CNTN1 | DBH | 0.49 |
| MST1 | TAGLN2 | 0.49 |
| PFN1 | PRDX2 | 0.49 |
| FCN3 | NA | 0.49 |
| CA1 | MASP2 | 0.49 |
| CKM | CNTN1 | 0.49 |
| GP5 | MASP2 | 0.49 |
| MST1 | PFN1 | 0.49 |
| MASP2 | TAGLN2 | 0.49 |
| MST1 | TLN1 | 0.49 |

TABLE 2-continued

Panel Combinations of Two Candidate Latent TB Biomarkers

| protein.1 | protein.2 | AUC |
|---|---|---|
| CLEC3B | CNTN1 | 0.49 |
| CNTN1 | COMP | 0.48 |
| FCN3 | IGF2 | 0.48 |
| CA1 | CLEC3B | 0.48 |
| PRDX2 | TAGLN2 | 0.48 |
| APOC1 | MST1 | 0.48 |
| CNTN1 | SHBG | 0.48 |
| CACNA2D1 | SPP2 | 0.48 |
| IGF2 | PCSK9 | 0.48 |
| CKM | TAGLN2 | 0.48 |
| MASP2 | PFN1 | 0.48 |
| FCN3 | GP5 | 0.48 |
| CACNA2D1 | CNTN1 | 0.48 |
| MASP2 | PCSK9 | 0.48 |
| CA2 | CLEC3B | 0.48 |
| CA2 | MASP2 | 0.48 |
| CACNA2D1 | MASP2 | 0.48 |
| CKM | CLEC3B | 0.48 |
| MASP2 | TLN1 | 0.48 |
| APOC3 | CACNA2D1 | 0.48 |
| GP5 | PRDX2 | 0.48 |
| CKM | PCSK9 | 0.48 |
| CLEC3B | SHBG | 0.48 |
| CLEC3B | TAGLN2 | 0.48 |
| PCSK9 | TAGLN2 | 0.48 |
| PRDX2 | NA | 0.48 |
| CLEC3B | PFN1 | 0.48 |
| IGF2 | PRDX2 | 0.48 |
| PCSK9 | PFN1 | 0.47 |
| CKM | PFN1 | 0.47 |
| GP5 | NA | 0.47 |
| SHBG | NA | 0.47 |
| CLEC3B | GP5 | 0.47 |
| GP5 | TAGLN2 | 0.47 |
| CKM | GP5 | 0.47 |
| FCN3 | PRDX2 | 0.47 |
| CA2 | PFN1 | 0.47 |
| CNTN1 | TLN1 | 0.47 |
| CA2 | PRDX2 | 0.47 |
| SHBG | TAGLN2 | 0.47 |
| CKM | COMP | 0.47 |
| IGF2 | SHBG | 0.47 |
| FCN3 | TAGLN2 | 0.47 |
| CA1 | CKM | 0.47 |
| APOC1 | CLEC3B | 0.47 |
| CLEC3B | CNDP1 | 0.47 |
| DBH | MASP2 | 0.47 |
| CA1 | PFN1 | 0.47 |
| CKM | SHBG | 0.47 |
| FCN3 | SHBG | 0.47 |
| MASP2 | SHBG | 0.47 |
| IGF2 | TAGLN2 | 0.47 |
| CLEC3B | TLN1 | 0.47 |
| CNDP1 | MASP2 | 0.47 |
| CA2 | TAGLN2 | 0.47 |
| GP5 | PFN1 | 0.47 |
| FCN3 | PCSK9 | 0.47 |
| IGF2 | PFN1 | 0.47 |
| FCN3 | PFN1 | 0.47 |
| PFN1 | SHBG | 0.46 |
| CA1 | TAGLN2 | 0.46 |
| CACNA2D1 | MST1 | 0.46 |
| CLEC3B | IGF2 | 0.46 |
| GP5 | IGF2 | 0.46 |
| CACNA2D1 | HGFAC | 0.46 |
| COMP | IGF2 | 0.46 |
| COMP | GP5 | 0.46 |
| GP5 | SHBG | 0.46 |
| CA1 | NA | 0.46 |
| CA2 | CKM | 0.46 |
| PRDX2 | SHBG | 0.46 |
| CKM | CNDP1 | 0.46 |
| CNDP1 | FCN3 | 0.46 |
| CLEC3B | DBH | 0.46 |
| CNDP1 | IGF2 | 0.46 |
| DBH | TAGLN2 | 0.46 |
| CA1 | IGF2 | 0.46 |
| CKM | IGF2 | 0.46 |
| APOC1 | MASP2 | 0.46 |
| CA1 | FCN3 | 0.46 |
| CA1 | GP5 | 0.46 |
| APOC1 | FCN3 | 0.46 |
| CA2 | FCN3 | 0.46 |
| COMP | PFN1 | 0.46 |
| CA2 | IGF2 | 0.46 |
| COMP | TAGLN2 | 0.45 |
| CNDP1 | TAGLN2 | 0.45 |
| DBH | PFN1 | 0.45 |
| CNDP1 | PFN1 | 0.45 |
| GP5 | TLN1 | 0.45 |
| CACNA2D1 | PRDX2 | 0.45 |
| CA2 | GP5 | 0.45 |
| GP5 | PCSK9 | 0.45 |
| APOC1 | TAGLN2 | 0.45 |
| APOC1 | CKM | 0.45 |
| DBH | FCN3 | 0.45 |
| CA1 | SHBG | 0.45 |
| PCSK9 | PRDX2 | 0.45 |
| COMP | FCN3 | 0.45 |
| COMP | SHBG | 0.45 |
| PCSK9 | SHBG | 0.45 |
| CKM | DBH | 0.45 |
| DBH | IGF2 | 0.45 |
| APOC1 | IGF2 | 0.45 |
| FCN3 | TLN1 | 0.45 |
| PCSK9 | NA | 0.45 |
| CNDP1 | PRDX2 | 0.45 |
| CA2 | NA | 0.45 |
| TLN1 | NA | 0.44 |
| CKM | TLN1 | 0.44 |
| APOC1 | PRDX2 | 0.44 |
| CNDP1 | GP5 | 0.44 |
| CA2 | SHBG | 0.44 |
| APOC1 | PFN1 | 0.44 |
| IGF2 | TLN1 | 0.44 |
| CA1 | CACNA2D1 | 0.44 |
| CACNA2D1 | FCN3 | 0.44 |
| CA1 | PCSK9 | 0.44 |
| DBH | NA | 0.44 |
| CA1 | PRDX2 | 0.44 |
| CNDP1 | NA | 0.44 |
| COMP | NA | 0.44 |
| DBH | PRDX2 | 0.44 |
| PFN1 | TAGLN2 | 0.44 |
| PRDX2 | TLN1 | 0.44 |
| SHBG | TLN1 | 0.44 |
| DBH | SHBG | 0.44 |
| CNDP1 | SHBG | 0.44 |
| CA2 | PCSK9 | 0.43 |
| APOC1 | NA | 0.43 |
| CACNA2D1 | CLEC3B | 0.43 |
| CACNA2D1 | IGF2 | 0.43 |
| APOC1 | GP5 | 0.43 |
| PCSK9 | TLN1 | 0.43 |
| CACNA2D1 | SHBG | 0.43 |
| CACNA2D1 | CKM | 0.43 |
| APOC1 | CA1 | 0.43 |
| CA1 | CNDP1 | 0.43 |
| CA1 | TLN1 | 0.43 |
| CA1 | CA2 | 0.43 |
| DBH | GP5 | 0.43 |
| COMP | PRDX2 | 0.43 |
| CNDP1 | PCSK9 | 0.43 |
| DBH | PCSK9 | 0.43 |
| APOC1 | PCSK9 | 0.43 |
| CACNA2D1 | NA | 0.43 |
| CA2 | CNDP1 | 0.43 |
| APOC1 | COMP | 0.42 |
| CNDP1 | COMP | 0.42 |
| CNDP1 | DBH | 0.42 |

TABLE 2-continued

Panel Combinations of Two Candidate Latent TB Biomarkers

| protein.1 | protein.2 | AUC |
|---|---|---|
| CA1 | COMP | 0.42 |
| COMP | PCSK9 | 0.42 |
| APOC1 | SHBG | 0.42 |
| CA2 | CACNA2D1 | 0.42 |
| CA2 | COMP | 0.42 |
| CA1 | DBH | 0.42 |
| COMP | TLN1 | 0.42 |
| CA2 | DBH | 0.42 |
| CNDP1 | TLN1 | 0.42 |
| DBH | TLN1 | 0.42 |
| APOC1 | CA2 | 0.42 |
| CACNA2D1 | TAGLN2 | 0.42 |
| APOC1 | TLN1 | 0.41 |
| CACNA2D1 | PFN1 | 0.41 |
| CA2 | TLN1 | 0.41 |
| APOC1 | CNDP1 | 0.41 |
| CACNA2D1 | GP5 | 0.41 |
| CACNA2D1 | TLN1 | 0.41 |
| CACNA2D1 | COMP | 0.41 |
| CACNA2D1 | PCSK9 | 0.41 |
| APOC1 | DBH | 0.41 |
| COMP | DBH | 0.40 |
| APOC1 | CACNA2D1 | 0.40 |
| CACNA2D1 | CNDP1 | 0.40 |
| CACNA2D1 | DBH | 0.40 |

TABLE 3

Panel Combinations of Three Candidate Latent TB Biomarkers

| protein.1 | protein.2 | protein.3 | AUC |
|---|---|---|---|
| CLEC3B | ECM1 | PON1 | 0.87 |
| CLEC3B | ECM1 | VTN | 0.85 |
| CLEC3B | ECM1 | VWF | 0.84 |
| CLEC3B | CPN2 | ECM1 | 0.83 |
| CLEC3B | ECM1 | TAGLN2 | 0.83 |
| CLEC3B | ECM1 | SELL | 0.83 |
| CLEC3B | CLU | ECM1 | 0.83 |
| CLEC3B | ECM1 | IGFALS | 0.83 |
| CLEC3B | CPN1 | ECM1 | 0.82 |
| CLEC3B | ECM1 | PFN1 | 0.82 |
| CLEC3B | ECM1 | LCP1 | 0.82 |
| CLEC3B | COMP | ECM1 | 0.82 |
| CLEC3B | ECM1 | SPP2 | 0.82 |
| CLEC3B | ECM1 | PEPD | 0.81 |
| CLEC3B | ECM1 | LPA | 0.81 |
| BTD | CLEC3B | ECM1 | 0.81 |
| CLEC3B | ECM1 | LRG1 | 0.81 |
| APOA4 | CLEC3B | ECM1 | 0.81 |
| ATRN | CLEC3B | ECM1 | 0.81 |
| CLEC3B | ECM1 | MST1 | 0.81 |
| CLEC3B | ECM1 | HYOU1 | 0.81 |
| CKM | CLEC3B | ECM1 | 0.81 |
| CLEC3B | ECM1 | NCAM1 | 0.80 |
| CLEC3B | ECM1 | LGALS3BP | 0.80 |
| CLEC3B | ECM1 | THBS1 | 0.80 |
| CLEC3B | ECM1 | SHBG | 0.80 |
| BCHE | CLEC3B | ECM1 | 0.80 |
| CLEC3B | ECM1 | LCAT | 0.80 |
| CD14 | CLEC3B | ECM1 | 0.80 |
| CDH5 | CLEC3B | ECM1 | 0.80 |
| CLEC3B | ECM1 | PRG4 | 0.80 |
| CLEC3B | ECM1 | PTGDS | 0.80 |
| CLEC3B | ECM1 | GPLD1 | 0.80 |
| CLEC3B | ECM1 | PDLIM1 | 0.80 |
| CLEC3B | ECM1 | PRDX2 | 0.80 |
| CLEC3B | ECM1 | HABP2 | 0.80 |
| CLEC3B | ECM1 | TNXB | 0.80 |
| CLEC3B | ECM1 | TGFBI | 0.80 |
| APOE | CLEC3B | ECM1 | 0.80 |
| CLEC3B | ECM1 | TLN1 | 0.80 |

TABLE 3-continued

Panel Combinations of Three Candidate Latent TB Biomarkers

| protein.1 | protein.2 | protein.3 | AUC |
|---|---|---|---|
| CLEC3B | ECM1 | GP1BA | 0.80 |
| APOA1 | CLEC3B | ECM1 | 0.80 |
| CLEC3B | ECM1 | GP5 | 0.80 |
| CLEC3B | ECM1 | FCN3 | 0.80 |
| CLEC3B | ECM1 | PROS1 | 0.80 |
| CLEC3B | ECM1 | QSOX1 | 0.80 |
| CA2 | CLEC3B | ECM1 | 0.80 |
| CLEC3B | ECM1 | MAN1A1 | 0.80 |
| CLEC3B | ECM1 | VCAM1 | 0.80 |
| CLEC3B | ECM1 | IGFBP3 | 0.80 |
| CLEC3B | ECM1 | MASP2 | 0.80 |
| CLEC3B | CNDP1 | ECM1 | 0.80 |
| CLEC3B | ECM1 | ORM1 | 0.80 |
| APOC3 | CLEC3B | ECM1 | 0.79 |
| APOC1 | CLEC3B | ECM1 | 0.79 |
| CA1 | CLEC3B | ECM1 | 0.79 |
| CLEC3B | ECM1 | NID1 | 0.79 |
| CLEC3B | ECM1 | GPX3 | 0.79 |
| CD163 | CLEC3B | ECM1 | 0.79 |
| CLEC3B | ECM1 | HGFAC | 0.79 |
| CLEC3B | ECM1 | MINPP1 | 0.79 |
| CLEC3B | ECM1 | PGLYRP2 | 0.79 |
| CLEC3B | ECM1 | S100A8 | 0.79 |
| CLEC3B | ECM1 | VASN | 0.79 |
| CLEC3B | DBH | ECM1 | 0.79 |
| CLEC3B | ECM1 | IGF2 | 0.79 |
| CLEC3B | CPB2 | ECM1 | 0.79 |
| CLEC3B | ECM1 | MASP1 | 0.79 |
| CLEC3B | ECM1 | PCSK9 | 0.79 |
| CLEC3B | ECM1 | LUM | 0.79 |
| CLEC3B | ECM1 | SEPP1 | 0.79 |
| CACNA2D1 | CLEC3B | ECM1 | 0.79 |
| CLEC3B | ECM1 | S100A9 | 0.79 |
| CLEC3B | CNTN1 | ECM1 | 0.76 |

TABLE 4

Panel Combinations of Four Candidate Latent TB Biomarkers

| protein.1 | protein.2 | protein.3 | protein.4 | AUC |
|---|---|---|---|---|
| CLEC3B | ECM1 | IGFALS | PON1 | 1.00 |
| CLEC3B | ECM1 | LPA | PON1 | 0.93 |
| CLEC3B | ECM1 | PON1 | TAGLN2 | 0.92 |
| CLEC3B | ECM1 | PFN1 | PON1 | 0.90 |
| CLEC3B | ECM1 | PON1 | VCAM1 | 0.90 |
| CLEC3B | ECM1 | NCAM1 | PON1 | 0.90 |
| APOA4 | CLEC3B | ECM1 | PON1 | 0.90 |
| CLEC3B | ECM1 | PON1 | SELL | 0.89 |
| CLEC3B | ECM1 | PON1 | VTN | 0.89 |
| APOC1 | CLEC3B | ECM1 | PON1 | 0.89 |
| CLEC3B | CNDP1 | ECM1 | PON1 | 0.89 |
| CLEC3B | CPN2 | ECM1 | PON1 | 0.89 |
| CLEC3B | ECM1 | MINPP1 | PON1 | 0.88 |
| ATRN | CLEC3B | ECM1 | PON1 | 0.88 |
| CLEC3B | ECM1 | NID1 | PON1 | 0.88 |
| CLEC3B | COMP | ECM1 | PON1 | 0.88 |
| CLEC3B | ECM1 | HABP2 | PON1 | 0.88 |
| CACNA2D1 | CLEC3B | ECM1 | PON1 | 0.88 |
| CD163 | CLEC3B | ECM1 | PON1 | 0.88 |
| CLEC3B | ECM1 | LCAT | PON1 | 0.88 |
| CLEC3B | ECM1 | PGLYRP2 | PON1 | 0.88 |
| CLEC3B | ECM1 | PON1 | PRG4 | 0.88 |
| CLEC3B | ECM1 | PON1 | TLN1 | 0.87 |
| CLEC3B | CPN1 | ECM1 | PON1 | 0.87 |
| CDH5 | CLEC3B | ECM1 | PON1 | 0.87 |
| CLEC3B | ECM1 | PEPD | PON1 | 0.87 |
| APOA1 | CLEC3B | ECM1 | PON1 | 0.87 |
| CLEC3B | ECM1 | PON1 | TGFBI | 0.87 |
| CLEC3B | ECM1 | PON1 | QSOX1 | 0.87 |
| CLEC3B | ECM1 | GP1BA | PON1 | 0.87 |
| CLEC3B | ECM1 | MST1 | PON1 | 0.87 |
| CLEC3B | CLU | ECM1 | PON1 | 0.87 |

TABLE 4-continued

Panel Combinations of Four Candidate Latent TB Biomarkers

| protein.1 | protein.2 | protein.3 | protein.4 | AUC |
|---|---|---|---|---|
| CLEC3B | ECM1 | MAN1A1 | PON1 | 0.87 |
| BTD | CLEC3B | ECM1 | PON1 | 0.87 |
| CLEC3B | ECM1 | HYOU1 | PON1 | 0.87 |
| CLEC3B | ECM1 | IGFBP3 | PON1 | 0.87 |
| CA2 | CLEC3B | ECM1 | PON1 | 0.87 |
| CLEC3B | ECM1 | GPX3 | PON1 | 0.87 |
| CLEC3B | ECM1 | MASP1 | PON1 | 0.87 |
| CLEC3B | ECM1 | HGFAC | PON1 | 0.87 |
| CLEC3B | ECM1 | PCSK9 | PON1 | 0.87 |
| CLEC3B | ECM1 | GP5 | PON1 | 0.87 |
| BCHE | CLEC3B | ECM1 | PON1 | 0.87 |
| CLEC3B | ECM1 | GPLD1 | PON1 | 0.87 |
| CLEC3B | ECM1 | PON1 | SPP2 | 0.87 |
| CLEC3B | ECM1 | PON1 | VASN | 0.86 |
| CLEC3B | ECM1 | PON1 | PTGDS | 0.86 |
| CLEC3B | ECM1 | PON1 | THBS1 | 0.86 |
| CLEC3B | ECM1 | PON1 | TNXB | 0.86 |
| CLEC3B | ECM1 | LCP1 | PON1 | 0.86 |
| CLEC3B | ECM1 | PON1 | PRDX2 | 0.86 |
| APOE | CLEC3B | ECM1 | PON1 | 0.86 |
| APOC3 | CLEC3B | ECM1 | PON1 | 0.86 |
| CLEC3B | ECM1 | MASP2 | PON1 | 0.86 |
| CLEC3B | ECM1 | LGALS3BP | PON1 | 0.86 |
| CLEC3B | ECM1 | PON1 | SHBG | 0.86 |
| CLEC3B | ECM1 | PON1 | S100A9 | 0.86 |
| CLEC3B | ECM1 | PON1 | SEPP1 | 0.86 |
| CLEC3B | ECM1 | LUM | PON1 | 0.86 |
| CKM | CLEC3B | ECM1 | PON1 | 0.86 |
| CLEC3B | ECM1 | PON1 | S100A8 | 0.86 |
| CLEC3B | ECM1 | PDLIM1 | PON1 | 0.86 |
| CLEC3B | ECM1 | PON1 | VWF | 0.86 |
| CA1 | CLEC3B | ECM1 | PON1 | 0.86 |
| CLEC3B | ECM1 | PON1 | PROS1 | 0.86 |
| CLEC3B | ECM1 | IGF2 | PON1 | 0.86 |
| CLEC3B | ECM1 | FCN3 | PON1 | 0.86 |
| CD14 | CLEC3B | ECM1 | PON1 | 0.85 |
| CLEC3B | DBH | ECM1 | PON1 | 0.85 |
| CLEC3B | CPB2 | ECM1 | PON1 | 0.85 |
| CLEC3B | ECM1 | ORM1 | PON1 | 0.85 |
| CLEC3B | ECM1 | LRG1 | PON1 | 0.85 |
| CLEC3B | CNTN1 | ECM1 | PON1 | 0.84 |

TABLE 5

Panel Combinations of Four Candidate Latent TB Biomarkers

| protein.1 | protein.2 | protein.3 | protein.4 | AUC |
|---|---|---|---|---|
| CLEC3B | ECM1 | PON1 | VTN | 0.89 |
| CLEC3B | CNDP1 | ECM1 | VTN | 0.88 |
| CLEC3B | ECM1 | IGFBP3 | VTN | 0.88 |
| CLEC3B | ECM1 | LPA | VTN | 0.88 |
| CLEC3B | ECM1 | IGFALS | VTN | 0.87 |
| CLEC3B | CPN2 | ECM1 | VTN | 0.87 |
| CLEC3B | ECM1 | VASN | VTN | 0.87 |
| CLEC3B | ECM1 | PEPD | VTN | 0.86 |
| CLEC3B | ECM1 | SPP2 | VTN | 0.86 |
| CLEC3B | CPN1 | ECM1 | VTN | 0.86 |
| CLEC3B | CLU | ECM1 | VTN | 0.86 |
| CACNA2D1 | CLEC3B | ECM1 | VTN | 0.86 |
| CLEC3B | ECM1 | TAGLN2 | VTN | 0.86 |
| CLEC3B | ECM1 | QSOX1 | VTN | 0.86 |
| CLEC3B | ECM1 | PFN1 | VTN | 0.86 |
| CLEC3B | ECM1 | PRG4 | VTN | 0.86 |
| CLEC3B | ECM1 | LUM | VTN | 0.86 |
| CLEC3B | ECM1 | VTN | VWF | 0.86 |
| CLEC3B | ECM1 | GPX3 | VTN | 0.85 |
| CA1 | CLEC3B | ECM1 | VTN | 0.85 |
| CLEC3B | ECM1 | NCAM1 | VTN | 0.85 |
| CLEC3B | COMP | ECM1 | VTN | 0.85 |
| CLEC3B | ECM1 | PRDX2 | VTN | 0.85 |
| ATRN | CLEC3B | ECM1 | VTN | 0.85 |
| CLEC3B | ECM1 | MST1 | VTN | 0.85 |

TABLE 5-continued

Panel Combinations of Four Candidate Latent TB Biomarkers

| protein.1 | protein.2 | protein.3 | protein.4 | AUC |
|---|---|---|---|---|
| CA2 | CLEC3B | ECM1 | VTN | 0.85 |
| CLEC3B | ECM1 | SELL | VTN | 0.85 |
| APOA4 | CLEC3B | ECM1 | VTN | 0.84 |
| CLEC3B | ECM1 | GPLD1 | VTN | 0.84 |
| APOC1 | CLEC3B | ECM1 | VTN | 0.84 |
| CLEC3B | ECM1 | GP1BA | VTN | 0.84 |
| APOE | CLEC3B | ECM1 | VTN | 0.84 |
| CLEC3B | ECM1 | HABP2 | VTN | 0.84 |
| CLEC3B | ECM1 | PTGDS | VTN | 0.84 |
| BCHE | CLEC3B | ECM1 | VTN | 0.84 |
| CLEC3B | ECM1 | TLN1 | VTN | 0.84 |
| CLEC3B | ECM1 | LRG1 | VTN | 0.83 |
| CD163 | CLEC3B | ECM1 | VTN | 0.83 |
| CLEC3B | ECM1 | MASP1 | VTN | 0.83 |
| CLEC3B | ECM1 | TNXB | VTN | 0.83 |
| CLEC3B | ECM1 | PCSK9 | VTN | 0.83 |
| CLEC3B | ECM1 | MASP2 | VTN | 0.83 |
| CLEC3B | ECM1 | THBS1 | VTN | 0.83 |
| CLEC3B | ECM1 | SHBG | VTN | 0.83 |
| CKM | CLEC3B | ECM1 | VTN | 0.83 |
| CLEC3B | ECM1 | TGFBI | VTN | 0.83 |
| APOC3 | CLEC3B | ECM1 | VTN | 0.83 |
| CLEC3B | ECM1 | PDLIM1 | VTN | 0.83 |
| CLEC3B | ECM1 | LGALS3BP | VTN | 0.83 |
| BTD | CLEC3B | ECM1 | VTN | 0.83 |
| CLEC3B | ECM1 | NID1 | VTN | 0.83 |
| APOA1 | CLEC3B | ECM1 | VTN | 0.83 |
| CLEC3B | ECM1 | VCAM1 | VTN | 0.83 |
| CLEC3B | ECM1 | LCP1 | VTN | 0.83 |
| CLEC3B | CPB2 | ECM1 | VTN | 0.83 |
| CDH5 | CLEC3B | ECM1 | VTN | 0.83 |
| CLEC3B | ECM1 | LCAT | VTN | 0.83 |
| CLEC3B | ECM1 | MINPP1 | VTN | 0.83 |
| CLEC3B | ECM1 | MAN1A1 | VTN | 0.83 |
| CLEC3B | ECM1 | ORM1 | VTN | 0.83 |
| CLEC3B | ECM1 | HYOU1 | VTN | 0.83 |
| CLEC3B | ECM1 | PGLYRP2 | VTN | 0.83 |
| CLEC3B | ECM1 | FCN3 | VTN | 0.82 |
| CD14 | CLEC3B | ECM1 | VTN | 0.82 |
| CLEC3B | ECM1 | IGF2 | VTN | 0.82 |
| CLEC3B | ECM1 | HGFAC | VTN | 0.82 |
| CLEC3B | ECM1 | SEPP1 | VTN | 0.82 |
| CLEC3B | ECM1 | GP5 | VTN | 0.82 |
| CLEC3B | ECM1 | PROS1 | VTN | 0.82 |
| CLEC3B | ECM1 | S100A8 | VTN | 0.82 |
| CLEC3B | ECM1 | S100A9 | VTN | 0.82 |
| CLEC3B | DBH | ECM1 | VTN | 0.82 |
| CLEC3B | CNTN1 | ECM1 | VTN | 0.82 |

TABLE 6

Panel Combinations of Two or Three Active TB Biomarkers

| protein.1 | protein.2 | protein.3 | AUC |
|---|---|---|---|
| CD14 | QSOX1 | SELL | 0.76 |
| CD14 | SELL | NA | 0.75 |
| CPN2 | SELL | NA | 0.74 |
| SELL | SEPP1 | NA | 0.73 |
| PEPD | SELL | NA | 0.73 |
| LGALS3BP | SELL | NA | 0.73 |
| CPN2 | QSOX1 | SELL | 0.73 |
| PGLYRP2 | SELL | NA | 0.73 |
| LGALS3BP | QSOX1 | SELL | 0.72 |
| QSOX1 | SELL | SEPP1 | 0.72 |
| PGLYRP2 | QSOX1 | SELL | 0.72 |
| CD14 | PEPD | SELL | 0.72 |
| CD14 | SELL | SEPP1 | 0.72 |
| SELL | TAGLN2 | NA | 0.72 |
| PFN1 | SELL | NA | 0.72 |
| PEPD | QSOX1 | SELL | 0.72 |
| SELL | VASN | NA | 0.72 |
| CPN2 | PEPD | SELL | 0.72 |

TABLE 6-continued

Panel Combinations of Two or Three Active TB Biomarkers

| protein.1 | protein.2 | protein.3 | AUC |
|---|---|---|---|
| QSOX1 | SELL | TAGLN2 | 0.71 |
| LGALS3BP | SELL | SEPP1 | 0.71 |
| QSOX1 | SELL | VASN | 0.71 |
| CPN2 | SELL | SEPP1 | 0.71 |
| CD14 | LGALS3BP | SELL | 0.71 |
| LGALS3BP | PEPD | SELL | 0.71 |
| PEPD | SELL | SEPP1 | 0.71 |
| PFN1 | QSOX1 | SELL | 0.71 |
| CD14 | SELL | VASN | 0.70 |
| CD14 | CPN2 | SELL | 0.70 |
| CD14 | PFN1 | SELL | 0.70 |
| PGLYRP2 | SELL | SEPP1 | 0.70 |
| PEPD | PGLYRP2 | SELL | 0.70 |
| CD14 | SELL | TAGLN2 | 0.70 |
| LGALS3BP | PGLYRP2 | SELL | 0.70 |
| CPN2 | LGALS3BP | SELL | 0.70 |
| LGALS3BP | SELL | TAGLN2 | 0.70 |
| LGALS3BP | PFN1 | SELL | 0.70 |
| CD14 | PGLYRP2 | SELL | 0.69 |
| PEPD | SELL | TAGLN2 | 0.69 |
| PGLYRP2 | SELL | TAGLN2 | 0.69 |
| PFN1 | PGLYRP2 | SELL | 0.69 |
| CPN2 | PFN1 | SELL | 0.69 |
| PEPD | PFN1 | SELL | 0.69 |
| CPN2 | SELL | TAGLN2 | 0.69 |
| SELL | SEPP1 | VASN | 0.69 |
| CD14 | CPN2 | NA | 0.69 |
| CPN2 | SELL | VASN | 0.69 |
| SELL | SEPP1 | TAGLN2 | 0.69 |
| PEPD | SELL | VASN | 0.69 |
| PFN1 | SELL | SEPP1 | 0.69 |
| CPN2 | PGLYRP2 | SELL | 0.69 |
| LGALS3BP | SELL | VASN | 0.69 |
| CD14 | LGALS3BP | NA | 0.69 |
| SELL | TAGLN2 | VASN | 0.69 |
| PGLYRP2 | SELL | VASN | 0.69 |
| PFN1 | SELL | VASN | 0.68 |
| PFN1 | SELL | TAGLN2 | 0.68 |
| CD14 | TAGLN2 | NA | 0.68 |
| CD14 | SEPP1 | NA | 0.68 |
| CD14 | PEPD | NA | 0.68 |
| CD14 | PFN1 | NA | 0.68 |
| CD14 | CPN2 | QSOX1 | 0.68 |
| CD14 | LGALS3BP | QSOX1 | 0.67 |
| CD14 | PGLYRP2 | NA | 0.67 |
| CD14 | VASN | NA | 0.67 |
| CD14 | QSOX1 | SEPP1 | 0.67 |
| CD14 | QSOX1 | VASN | 0.67 |
| CD14 | QSOX1 | TAGLN2 | 0.67 |
| CD14 | PGLYRP2 | QSOX1 | 0.67 |
| CD14 | PEPD | QSOX1 | 0.66 |
| CD14 | PFN1 | QSOX1 | 0.66 |
| CD14 | CPN2 | PEPD | 0.65 |
| CD14 | CPN2 | SEPP1 | 0.65 |
| CPN2 | PGLYRP2 | NA | 0.65 |
| CD14 | LGALS3BP | PEPD | 0.65 |
| CD14 | LGALS3BP | TAGLN2 | 0.65 |
| CD14 | PGLYRP2 | TAGLN2 | 0.65 |
| CD14 | PFN1 | TAGLN2 | 0.65 |
| CD14 | SEPP1 | TAGLN2 | 0.65 |
| CD14 | CPN2 | LGALS3BP | 0.65 |
| CD14 | PGLYRP2 | SEPP1 | 0.64 |
| CD14 | LGALS3BP | SEPP1 | 0.64 |
| CD14 | PFN1 | PGLYRP2 | 0.64 |
| CD14 | PEPD | SEPP1 | 0.64 |
| CD14 | LGALS3BP | PGLYRP2 | 0.64 |
| CD14 | CPN2 | TAGLN2 | 0.64 |
| CD14 | LGALS3BP | PFN1 | 0.64 |
| CD14 | CPN2 | PFN1 | 0.64 |
| CD14 | LGALS3BP | VASN | 0.64 |
| CPN2 | VASN | NA | 0.64 |
| LGALS3BP | PGLYRP2 | NA | 0.64 |
| CD14 | PEPD | TAGLN2 | 0.64 |
| CD14 | CPN2 | PGLYRP2 | 0.64 |
| CD14 | PEPD | VASN | 0.64 |
| CD14 | CPN2 | VASN | 0.64 |
| CD14 | PEPD | PFN1 | 0.64 |
| CD14 | PEPD | PGLYRP2 | 0.64 |
| CD14 | TAGLN2 | VASN | 0.63 |
| CD14 | PFN1 | SEPP1 | 0.63 |
| CD14 | SEPP1 | VASN | 0.63 |
| PGLYRP2 | SEPP1 | NA | 0.63 |
| CD14 | PFN1 | VASN | 0.63 |
| CPN2 | LGALS3BP | NA | 0.63 |
| CD14 | PGLYRP2 | VASN | 0.63 |
| CPN2 | PGLYRP2 | SEPP1 | 0.63 |
| CPN2 | PGLYRP2 | QSOX1 | 0.63 |
| CPN2 | PEPD | NA | 0.62 |
| CPN2 | SEPP1 | NA | 0.62 |
| PGLYRP2 | VASN | NA | 0.62 |
| CPN2 | PFN1 | NA | 0.62 |
| CPN2 | TAGLN2 | NA | 0.62 |
| CPN2 | PEPD | PGLYRP2 | 0.61 |
| CPN2 | PGLYRP2 | TAGLN2 | 0.61 |
| CPN2 | PFN1 | PGLYRP2 | 0.61 |
| CPN2 | LGALS3BP | PGLYRP2 | 0.61 |
| PGLYRP2 | TAGLN2 | NA | 0.61 |
| CPN2 | QSOX1 | VASN | 0.61 |
| CPN2 | LGALS3BP | QSOX1 | 0.61 |
| LGALS3BP | PGLYRP2 | SEPP1 | 0.61 |
| LGALS3BP | PGLYRP2 | QSOX1 | 0.61 |
| PFN1 | PGLYRP2 | NA | 0.61 |
| LGALS3BP | PGLYRP2 | VASN | 0.61 |
| CPN2 | PGLYRP2 | VASN | 0.61 |
| LGALS3BP | VASN | NA | 0.61 |
| CPN2 | QSOX1 | SEPP1 | 0.60 |
| LGALS3BP | PGLYRP2 | TAGLN2 | 0.60 |
| CPN2 | PEPD | QSOX1 | 0.60 |
| CPN2 | PEPD | VASN | 0.60 |
| CPN2 | LGALS3BP | VASN | 0.60 |
| LGALS3BP | PFN1 | PGLYRP2 | 0.60 |
| PGLYRP2 | QSOX1 | SEPP1 | 0.60 |
| PGLYRP2 | QSOX1 | VASN | 0.60 |
| CPN2 | PFN1 | QSOX1 | 0.60 |
| PEPD | PGLYRP2 | NA | 0.59 |
| CPN2 | SEPP1 | VASN | 0.59 |
| PGLYRP2 | QSOX1 | TAGLN2 | 0.59 |
| CPN2 | QSOX1 | TAGLN2 | 0.59 |
| PGLYRP2 | SEPP1 | VASN | 0.59 |
| CPN2 | TAGLN2 | VASN | 0.59 |
| LGALS3BP | QSOX1 | VASN | 0.59 |
| CPN2 | LGALS3BP | PEPD | 0.59 |
| CPN2 | PFN1 | VASN | 0.59 |
| PGLYRP2 | SEPP1 | TAGLN2 | 0.59 |
| PFN1 | PGLYRP2 | QSOX1 | 0.59 |
| LGALS3BP | QSOX1 | SEPP1 | 0.58 |
| LGALS3BP | PEPD | PGLYRP2 | 0.58 |
| CPN2 | LGALS3BP | PFN1 | 0.58 |
| PFN1 | PGLYRP2 | SEPP1 | 0.58 |
| PGLYRP2 | TAGLN2 | VASN | 0.58 |
| CPN2 | LGALS3BP | TAGLN2 | 0.58 |
| LGALS3BP | SEPP1 | NA | 0.58 |
| PFN1 | PGLYRP2 | VASN | 0.58 |
| LGALS3BP | PEPD | QSOX1 | 0.58 |
| CPN2 | LGALS3BP | SEPP1 | 0.58 |
| PEPD | PGLYRP2 | QSOX1 | 0.58 |
| QSOX1 | VASN | NA | 0.58 |
| CPN2 | PFN1 | TAGLN2 | 0.57 |
| PEPD | QSOX1 | NA | 0.57 |
| LGALS3BP | PEPD | NA | 0.57 |
| LGALS3BP | QSOX1 | TAGLN2 | 0.57 |
| SEPP1 | VASN | NA | 0.57 |
| CPN2 | SEPP1 | TAGLN2 | 0.57 |
| LGALS3BP | SEPP1 | VASN | 0.57 |
| LGALS3BP | PFN1 | QSOX1 | 0.57 |
| CPN2 | PEPD | SEPP1 | 0.57 |
| PFN1 | PGLYRP2 | TAGLN2 | 0.57 |
| PEPD | PGLYRP2 | SEPP1 | 0.57 |
| CPN2 | PFN1 | SEPP1 | 0.57 |
| PEPD | PGLYRP2 | VASN | 0.57 |
| CPN2 | PEPD | TAGLN2 | 0.57 |
| PEPD | PGLYRP2 | TAGLN2 | 0.57 |

TABLE 6-continued

Panel Combinations of Two or Three Active TB Biomarkers

| protein.1 | protein.2 | protein.3 | AUC |
|---|---|---|---|
| LGALS3BP | PEPD | VASN | 0.57 |
| QSOX1 | SEPP1 | VASN | 0.56 |
| PEPD | PFN1 | PGLYRP2 | 0.56 |
| LGALS3BP | TAGLN2 | VASN | 0.56 |
| PFN1 | QSOX1 | NA | 0.56 |
| QSOX1 | TAGLN2 | NA | 0.56 |
| LGALS3BP | TAGLN2 | NA | 0.56 |
| PEPD | VASN | NA | 0.56 |
| LGALS3BP | PFN1 | VASN | 0.55 |
| PEPD | SEPP1 | NA | 0.55 |
| LGALS3BP | PFN1 | NA | 0.55 |
| PEPD | QSOX1 | SEPP1 | 0.55 |
| LGALS3BP | PEPD | SEPP1 | 0.55 |
| LGALS3BP | SEPP1 | TAGLN2 | 0.55 |
| PEPD | QSOX1 | VASN | 0.54 |
| QSOX1 | SEPP1 | TAGLN2 | 0.54 |
| PFN1 | QSOX1 | SEPP1 | 0.54 |
| LGALS3BP | PFN1 | SEPP1 | 0.54 |
| LGALS3BP | PEPD | TAGLN2 | 0.54 |
| SEPP1 | TAGLN2 | NA | 0.54 |
| PFN1 | SEPP1 | NA | 0.54 |
| TAGLN2 | VASN | NA | 0.54 |
| PEPD | TAGLN2 | NA | 0.53 |
| PEPD | PFN1 | NA | 0.53 |
| QSOX1 | TAGLN2 | VASN | 0.53 |
| PEPD | QSOX1 | TAGLN2 | 0.53 |
| PEPD | SEPP1 | VASN | 0.53 |
| PEPD | PFN1 | QSOX1 | 0.53 |
| SEPP1 | TAGLN2 | VASN | 0.53 |
| LGALS3BP | PFN1 | TAGLN2 | 0.53 |
| PFN1 | QSOX1 | VASN | 0.53 |
| PFN1 | VASN | NA | 0.53 |
| PFN1 | SEPP1 | VASN | 0.53 |
| PEPD | TAGLN2 | VASN | 0.53 |
| PEPD | PFN1 | VASN | 0.52 |
| PFN1 | QSOX1 | TAGLN2 | 0.52 |
| PEPD | SEPP1 | TAGLN2 | 0.52 |
| PEPD | PFN1 | SEPP1 | 0.51 |
| PEPD | PFN1 | TAGLN2 | 0.50 |
| PFN1 | SEPP1 | TAGLN2 | 0.50 |
| PFN1 | TAGLN2 | VASN | 0.50 |
| PFN1 | TAGLN2 | NA | 0.44 |

TABLE 7

Panel Combinations of Active TB and Latent TB Biomarkers

| protein.1 | protein.2 | protein.3 | AUC |
|---|---|---|---|
| CLEC3B | CPN2 | ECM1 | 0.83 |
| CLEC3B | ECM1 | TAGLN2 | 0.83 |
| CLEC3B | ECM1 | SELL | 0.83 |
| CLEC3B | ECM1 | PFN1 | 0.82 |
| CLEC3B | ECM1 | PEPD | 0.81 |
| CLEC3B | ECM1 | LGALS3BP | 0.80 |
| CD14 | CLEC3B | ECM1 | 0.80 |
| CLEC3B | ECM1 | QSOX1 | 0.80 |
| CLEC3B | ECM1 | PGLYRP2 | 0.79 |
| CLEC3B | ECM1 | VASN | 0.79 |
| CLEC3B | ECM1 | SEPP1 | 0.79 |

TABLE 8

Cross-Sectional Comparison of Differential Intensity (DI) Ratios for Select Latent TB Biomarkers

| Gene | CO v NI | LTBI v NI | ATB v NI | ATB v LTBI |
|---|---|---|---|---|
| CLEC3B | 1.00 | 1.06 | 0.55 | 0.52 |
| ECM1 | 0.84 | 0.81 | 0.92 | 1.13 |
| PON1 | 1.20 | 1.43 | 0.73 | 0.51 |
| VTN | 1.10 | 1.16 | 0.75 | 0.65 |
| IGFALS | 1.00 | 0.99 | 0.77 | 0.78 |
| IGFBP3 | 0.81 | 0.84 | 0.41 | 0.49 |
| CLU | 1.13 | 1.19 | 0.92 | 0.77 |
| VWF | 1.34 | 1.08 | 1.06 | 0.98 |
| SPP2 | 1.05 | 1.05 | 0.53 | 0.50 |
| SELL | 1.07 | 1.00 | 1.00 | 0.99 |
| LUM | 0.88 | 0.90 | 0.57 | 0.63 |
| NCAM1 | 0.99 | 0.95 | 0.53 | 0.56 |
| TLN1 | 1.22 | 1.08 | 0.55 | 0.51 |

TABLE 9

Longitudinal Comparison of Differential Intensity (DI) Ratios for Select Latent TB Biomarkers

| Gene | Becomes TST+ | Remains TST− |
|---|---|---|
| CLEC3B | 1.29 | 1.22 |
| ECM1 | 1.43 | 1.34 |
| PON1 | 1.28 | 1.00 |
| VTN | 1.06 | 1.01 |
| IGFALS | 1.24 | 1.16 |
| IGFBP3 | 1.24 | 1.16 |
| CLU | 1.15 | 1.13 |
| VWF | 1.42 | 1.35 |
| SPP2 | 1.11 | 1.09 |
| SELL | 1.15 | 1.25 |
| LUM | 1.25 | 1.22 |
| NCAM1 | 1.17 | 1.18 |
| TLN1 | 1.01 | 0.96 |

EQUIVALENTS

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by $\frac{1}{20}$th, $\frac{1}{10}$th, $\frac{1}{5}$th, $\frac{1}{3}$rd, $\frac{1}{2}$, etc., or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

INCORPORATION BY REFERENCE

The contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

We claim:

1. A method for detecting the level of CLEC3B, ECM1, PON1, and IGFLAS in a human subject exposed to *Mycobacterium tuberculosis* (TB), the method comprising
    obtaining a fluid sample(s) from the human subject exposed to TB; and
    detecting CLEC3B, ECM1, PON1, and IGFALS in the subject sample(s), thereby detecting CLEC3B, ECM1, PON1, and IGFLAS in the fluid sample(s) obtained from the human subject exposed to TB.

2. The method of claim 1, further comprising detecting VTN and one or more additional markers selected from the group consisting of IGFBP3, CLU, VWF, SPP2, SELL, LUM, NCAM1, and TLN1 in the fluid sample(s) obtained from the subject.

3. The method of claim 1, wherein detecting CLEC3B, ECM1, PON1, and IGFALS in the fluid sample(s) comprises ionizing the fluid sample(s) and detecting charged particles corresponding to CLEC3B, ECM1, PON1, and IGFALS.

4. The method of claim 1, wherein detecting CLEC3B, ECM1, PON1, and IGFALS in the fluid sample(s) comprises contacting the fluid sample(s) with an antibody, or antigen-binding fragment thereof, that specifically binds to CLEC3B, ECM1, PON1, or VTN.

5. The method of claim 1, wherein the subject is HIV negative.

6. The method of claim 1, wherein the fluid sample(s) is a blood sample(s) or a saliva sample(s).

7. The method of claim 1, further comprising detecting one or more markers selected from the group consisting of VTN, IGFBP3, CLU, VWF, SPP2, SELL, LUM, NCAM1, and TLN1 in the fluid sample(s) obtained from the subject.

8. The method of claim 1, further comprising detecting VTN in the fluid sample(s) obtained from the subject.

9. The method of claim 1, further comprising administering to the subject an effective amount of a therapeutic agent for treating TB.

* * * * *

UNITED STATES PATENT AND TRADEMARK OFFICE
CERTIFICATE OF CORRECTION

PATENT NO. : 10,935,549 B2
APPLICATION NO. : 16/246592
DATED : March 2, 2021
INVENTOR(S) : Eustache Paramithiotis et al.

Page 1 of 1

It is certified that error appears in the above-identified patent and that said Letters Patent is hereby corrected as shown below:

On the Title Page

Item (71) Applicants:
Please delete the first Applicant, "Caprion Biosciences Inc.", and replace it with --Caprion Proteomics Inc.--; and Item (73) Assignees:
Please delete the first Assignee, "Caption Biosciences Inc.", and replace it with --Caprion Proteomics Inc.--.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*